United States Patent
Handique et al.

(10) Patent No.: US 12,410,427 B2
(45) Date of Patent: Sep. 9, 2025

(54) SYSTEM AND METHOD FOR AUTOMATED SINGLE CELL PROCESSING

(71) Applicant: Bio-Rad Laboratories, Inc., Hercules, CA (US)

(72) Inventors: Kalyan Handique, Hercules, CA (US); Austin Payne, Hercules, CA (US); Sida Wang, Hercules, CA (US); Patrick Michael Tegels, Hercules, CA (US); William T. Koederitz, Hercules, CA (US); Daniel Genord, Hercules, CA (US); Grey Parker, Hercules, CA (US); Brian Boniface, Hercules, CA (US); Katlyn Curtin Mehne, Hercules, CA (US); Alec William Hitchiner, Hercules, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 1 day.

(21) Appl. No.: 18/094,278

(22) Filed: Jan. 6, 2023

(65) Prior Publication Data
US 2023/0159917 A1 May 25, 2023

Related U.S. Application Data

(63) Continuation of application No. 16/867,256, filed on May 5, 2020, now Pat. No. 11,578,322.
(Continued)

(51) Int. Cl.
*B01L 3/00* (2006.01)
*B01L 7/00* (2006.01)
(Continued)

(52) U.S. Cl.
CPC .......... *C12N 15/1096* (2013.01); *B01L 3/502* (2013.01); *B01L 3/502715* (2013.01);
(Continued)

(58) Field of Classification Search
None
See application file for complete search history.

(56) References Cited

U.S. PATENT DOCUMENTS

| 4,475,411 A | 10/1984 | Wellerfors |
| 4,551,435 A | 11/1985 | Liberti et al. |

(Continued)

FOREIGN PATENT DOCUMENTS

| CN | 202011883 U | 10/2011 |
| CN | 103894248 A | 7/2014 |

(Continued)

OTHER PUBLICATIONS

Yuan, Jinzhou, et al., "SCOPE-Seq: a scalable technology for linking live cell imaging and single-cell RNA sequencing", vol. 19, No. 227, Dec. 24, 2018, XP055680743, DOI: 10.1186/s13059-018-1607-x *Fig. 1; p. 3, left col. "in SCOPE-Seg, we load . . . ".
(Continued)

*Primary Examiner* — Aaron A Priest
(74) *Attorney, Agent, or Firm* — Thomas C. Meyers; Sullivan & Worcester

(57) ABSTRACT

A system and method for automated single cell capture and processing is described, where the system includes a deck supporting and positioning a set of sample processing elements; a gantry for actuating tools for interactions with the set of sample processing elements supported by the deck; and a base supporting various processing subsystems and a control subsystems in communication with the processing subsystems. The system can automatically execute workflows associated with single cell processing, including
(Continued)

mRNA capture, cDNA synthesis, protein-associated assays, and library preparation, for next generation sequencing.

20 Claims, 51 Drawing Sheets

Related U.S. Application Data

(60) Provisional application No. 62/844,470, filed on May 7, 2019, provisional application No. 62/866,726, filed on Jun. 26, 2019.

(51) Int. Cl.
  *B01L 9/02* (2006.01)
  *C12N 1/06* (2006.01)
  *C12N 15/10* (2006.01)
  *C12Q 1/6844* (2018.01)
  *G01F 23/292* (2006.01)
  *G01N 35/00* (2006.01)

(52) U.S. Cl.
  CPC ... *B01L 3/502738* (2013.01); *B01L 3/502761* (2013.01); *B01L 3/52* (2013.01); *B01L 7/52* (2013.01); *B01L 9/02* (2013.01); *C12N 1/06* (2013.01); *C12N 15/1093* (2013.01); *C12Q 1/6844* (2013.01); *G01F 23/292* (2013.01); *G01N 35/00* (2013.01); *B01L 2200/0647* (2013.01); *B01L 2200/16* (2013.01); *B01L 2300/041* (2013.01); *B01L 2300/042* (2013.01); *B01L 2300/047* (2013.01); *B01L 2300/06* (2013.01); *B01L 2300/0627* (2013.01); *B01L 2300/0819* (2013.01); *B01L 2300/0829* (2013.01); *B01L 2300/0893* (2013.01); *B01L 2300/123* (2013.01); *B01L 2300/16* (2013.01); *B01L 2300/1805* (2013.01); *B01L 2300/1894* (2013.01); *B01L 2400/043* (2013.01); *B01L 2400/06* (2013.01); *B01L 2400/0633* (2013.01)

(56) References Cited

U.S. PATENT DOCUMENTS

| | | | |
|---|---|---|---|
| 4,710,635 A | 12/1987 | Chupp |
| 5,266,269 A | 11/1993 | Niiyama et al. |
| 5,281,540 A | 1/1994 | Merkh et al. |
| 5,491,343 A | 2/1996 | Brooker |
| 5,541,064 A | 7/1996 | Bacus et al. |
| 5,547,849 A | 8/1996 | Baer et al. |
| 5,785,044 A | 7/1998 | Meador et al. |
| 5,851,488 A | 12/1998 | Saul et al. |
| 5,883,370 A | 3/1999 | Walker et al. |
| 5,888,370 A | 3/1999 | Becker et al. |
| 5,993,630 A | 11/1999 | Becker et al. |
| 5,993,632 A | 11/1999 | Becker et al. |
| 6,016,712 A | 1/2000 | Warden et al. |
| 6,127,177 A | 10/2000 | Toner et al. |
| 6,133,030 A | 10/2000 | Bhatia et al. |
| 6,150,180 A | 11/2000 | Parce et al. |
| 6,174,683 B1 | 1/2001 | Hahn |
| 6,221,663 B1 | 4/2001 | Bhatia et al. |
| 6,228,624 B1 | 5/2001 | Terstappen |
| 6,281,008 B1 | 8/2001 | Komai et al. |
| 6,287,832 B1 | 9/2001 | Becker et al. |
| 6,365,362 B1 | 4/2002 | Terstappen et al. |
| 6,410,724 B1 | 6/2002 | Dejean et al. |
| 6,433,134 B1 | 8/2002 | Patron et al. |
| 6,468,810 B1 | 10/2002 | Korpela |
| 6,525,997 B1 | 2/2003 | Narayanaswami et al. |
| 6,551,841 B1 | 4/2003 | Wilding et al. |
| 6,563,634 B2 | 5/2003 | Shimada et al. |
| 6,613,525 B2 | 9/2003 | Nelson et al. |
| 6,623,983 B1 | 9/2003 | Terstappen et al. |
| 6,641,708 B1 | 11/2003 | Becker et al. |
| 6,645,731 B2 | 11/2003 | Terstappen et al. |
| 6,692,952 B1 | 2/2004 | Braff et al. |
| 6,790,330 B2 | 9/2004 | Gascoyne et al. |
| 6,821,484 B1 | 11/2004 | Gregersen |
| 6,861,259 B2 | 3/2005 | Columbus |
| 6,866,823 B2 | 3/2005 | Wardlaw |
| 6,960,449 B2 | 11/2005 | Wang et al. |
| 7,008,789 B2 | 3/2006 | Gambini et al. |
| 7,035,170 B2 | 4/2006 | Narayanaswami et al. |
| 7,046,357 B2 | 5/2006 | Weinberger et al. |
| 7,148,492 B2 | 12/2006 | Loney et al. |
| 7,172,866 B2 | 2/2007 | Hahn et al. |
| 7,198,901 B1 | 4/2007 | Rachlin |
| 7,217,520 B2 | 5/2007 | Tsinberg et al. |
| 7,238,521 B2 | 7/2007 | Hahn et al. |
| 7,248,352 B2 | 7/2007 | Hamamatsu et al. |
| 7,258,990 B2 | 8/2007 | Falcovitz-Gerassi et al. |
| 7,266,777 B2 | 9/2007 | Scott et al. |
| 7,294,468 B2 | 11/2007 | Bell et al. |
| 7,316,897 B2 | 1/2008 | Bisconte et al. |
| 7,332,288 B2 | 2/2008 | Terstappen et al. |
| 7,338,760 B2 | 3/2008 | Gong et al. |
| 7,354,389 B2 | 4/2008 | Kureshy et al. |
| 7,439,062 B2 | 10/2008 | Bhatt et al. |
| 7,449,558 B2 | 11/2008 | Yao et al. |
| 7,449,778 B2 | 11/2008 | Sander |
| 7,501,283 B2 | 3/2009 | Hersch et al. |
| 7,507,528 B2 | 3/2009 | Albert et al. |
| 7,588,672 B2 | 9/2009 | Unger et al. |
| 7,595,157 B2 | 9/2009 | Tsinberg |
| 7,597,528 B2 | 10/2009 | Rodi |
| 7,604,777 B2 | 10/2009 | Columbus |
| 7,638,464 B2 | 12/2009 | Fagnani et al. |
| 7,695,956 B2 | 4/2010 | Tsinberg et al. |
| 7,704,322 B2 | 4/2010 | Hansen et al. |
| 7,710,563 B2 | 5/2010 | Betzig et al. |
| 7,738,320 B2 | 6/2010 | Taha |
| 7,763,704 B2 | 7/2010 | Ding et al. |
| 7,767,152 B2 | 8/2010 | Stead et al. |
| 7,815,863 B2 | 10/2010 | Kagan et al. |
| 7,858,757 B2 | 12/2010 | Hollmann et al. |
| 7,863,012 B2 | 1/2011 | Rao et al. |
| 7,901,950 B2 | 3/2011 | Connelly et al. |
| 7,964,349 B2 | 6/2011 | Bell et al. |
| 8,008,032 B2 | 8/2011 | Forsyth et al. |
| 8,013,298 B2 | 9/2011 | Khursheed |
| 8,021,614 B2 | 9/2011 | Huang et al. |
| 8,062,883 B2 | 11/2011 | Woudenberg et al. |
| 8,103,080 B2 | 1/2012 | George et al. |
| 8,105,769 B2 | 1/2012 | Bell et al. |
| 8,105,780 B2 | 1/2012 | Su et al. |
| 8,131,053 B2 | 3/2012 | Ortyn et al. |
| 8,158,410 B2 | 4/2012 | Tang et al. |
| 8,174,698 B2 | 5/2012 | Peter et al. |
| 8,175,371 B2 | 5/2012 | George et al. |
| 8,186,913 B2 | 5/2012 | Toner et al. |
| 8,211,301 B2 | 7/2012 | Safar et al. |
| 8,232,112 B2 | 7/2012 | Willson et al. |
| 8,252,517 B2 | 8/2012 | Thomas et al. |
| 8,293,524 B2 | 10/2012 | Ionescu-Zanetti et al. |
| 8,304,230 B2 | 11/2012 | Toner et al. |
| 8,329,422 B2 | 12/2012 | Rao et al. |
| 8,372,579 B2 | 2/2013 | Toner et al. |
| 8,372,584 B2 | 2/2013 | Shoemaker et al. |
| 8,406,498 B2 | 3/2013 | Ortyn et al. |
| 8,465,916 B2 | 6/2013 | Bell et al. |
| 8,628,923 B2 | 1/2014 | Hamilton et al. |
| 8,658,418 B2 | 2/2014 | Daridon |
| 8,680,025 B2 | 3/2014 | Cooney |
| 8,730,479 B2 | 5/2014 | Ness et al. |
| 8,765,454 B2 | 7/2014 | Zhou et al. |
| 8,771,609 B2 | 7/2014 | Ehben et al. |
| 8,802,367 B2 | 8/2014 | Taniguchi et al. |
| 8,936,945 B2 | 1/2015 | Handique et al. |
| 8,986,988 B2 | 3/2015 | Karnik et al. |
| 9,103,754 B2 | 8/2015 | Handique et al. |

(56) References Cited

U.S. PATENT DOCUMENTS

| | | |
|---|---|---|
| 9,110,026 B2 | 8/2015 | Collins |
| 9,133,499 B2 | 9/2015 | Di Carlo et al. |
| 9,145,540 B1 | 9/2015 | Deutsch et al. |
| 9,174,216 B2 | 11/2015 | Handique et al. |
| 9,188,586 B2 | 11/2015 | Fan et al. |
| 9,194,001 B2 | 11/2015 | Brenner |
| 9,200,245 B2 | 12/2015 | Deutsch et al. |
| 9,201,060 B2 | 12/2015 | Voldman et al. |
| 9,249,459 B2 | 2/2016 | Hamilton et al. |
| 9,260,753 B2 | 2/2016 | Xie et al. |
| 9,278,355 B2 | 3/2016 | Kajiyama et al. |
| 9,290,808 B2 | 3/2016 | Fodor et al. |
| 9,290,809 B2 | 3/2016 | Fodor et al. |
| 9,304,065 B2 | 4/2016 | Fowler et al. |
| 9,315,768 B2 | 4/2016 | Vrouwe et al. |
| 9,315,857 B2 | 4/2016 | Fu et al. |
| 9,329,170 B2 | 5/2016 | Clarke et al. |
| 9,364,829 B2 | 6/2016 | Heid et al. |
| 9,404,864 B2 | 8/2016 | Handique et al. |
| 9,410,201 B2 | 8/2016 | Hindson et al. |
| 9,429,500 B2 | 8/2016 | Fowler et al. |
| 9,506,845 B2 | 11/2016 | Fowler et al. |
| 9,507,609 B2 | 11/2016 | Glazer et al. |
| 9,513,195 B2 | 12/2016 | Handique et al. |
| 9,567,645 B2 | 2/2017 | Fan et al. |
| 9,567,646 B2 | 2/2017 | Fan et al. |
| 9,598,736 B2 | 3/2017 | Fan et al. |
| 9,606,102 B2 | 3/2017 | Handique et al. |
| 9,610,581 B2 | 4/2017 | Handique et al. |
| 9,637,799 B2 | 5/2017 | Fan et al. |
| 9,701,998 B2 | 7/2017 | Hindson et al. |
| 9,707,562 B2 | 7/2017 | Handique et al. |
| 9,708,659 B2 | 7/2017 | Fodor et al. |
| 9,746,413 B2 | 8/2017 | Handique et al. |
| 9,752,181 B2 | 9/2017 | Handique et al. |
| 9,757,707 B2 | 9/2017 | Husain et al. |
| 9,802,193 B2 | 10/2017 | Handique et al. |
| 9,840,732 B2 | 12/2017 | Anderson et al. |
| 9,845,502 B2 | 12/2017 | Fodor et al. |
| 9,850,483 B2 | 12/2017 | Clarke et al. |
| 9,952,126 B2 | 4/2018 | Fowler et al. |
| 9,995,662 B2 | 6/2018 | Husain et al. |
| 10,376,889 B1 | 8/2019 | Masquelier et al. |
| 10,391,490 B2 | 8/2019 | Handique et al. |
| 10,391,492 B2 | 8/2019 | Handique et al. |
| 10,391,493 B2 | 8/2019 | Handique et al. |
| 10,401,373 B1 | 9/2019 | Holmes et al. |
| 10,408,736 B1 | 9/2019 | Handique |
| 10,466,160 B2 | 11/2019 | Handique et al. |
| 10,533,152 B1 | 1/2020 | Belgrader et al. |
| 10,718,007 B2 | 7/2020 | Handique et al. |
| 10,900,032 B2 | 1/2021 | Handique et al. |
| 11,504,719 B2 | 11/2022 | Handique et al. |
| 11,724,256 B2 | 8/2023 | Handique |
| 11,788,120 B2 | 10/2023 | Sims et al. |
| 2002/0009759 A1 | 1/2002 | Terstappen et al. |
| 2002/0028431 A1 | 3/2002 | Julien |
| 2002/0036142 A1 | 3/2002 | Gascoyne et al. |
| 2002/0036823 A1 | 3/2002 | Shimada et al. |
| 2002/0098535 A1 | 7/2002 | Wang et al. |
| 2002/0109838 A1 | 8/2002 | Columbus |
| 2002/0119482 A1 | 8/2002 | Nelson et al. |
| 2002/0192808 A1 | 12/2002 | Gambini et al. |
| 2003/0096277 A1 | 5/2003 | Chen |
| 2003/0103662 A1 | 6/2003 | Finkbeiner |
| 2003/0129676 A1 | 7/2003 | Terstappen et al. |
| 2003/0138941 A1 | 7/2003 | Gong et al. |
| 2004/0029241 A1 | 2/2004 | Hahn et al. |
| 2004/0106130 A1 | 6/2004 | Besemer et al. |
| 2004/0109793 A1 | 6/2004 | McNeely et al. |
| 2004/0160599 A1 | 8/2004 | Hamamatsu et al. |
| 2004/0191891 A1 | 9/2004 | Tsinberg et al. |
| 2004/0218472 A1 | 11/2004 | Narayanaswami et al. |
| 2004/0229349 A1 | 11/2004 | Daridon |
| 2004/0239922 A1 | 12/2004 | Modlin et al. |
| 2004/0248318 A1 | 12/2004 | Weinberger et al. |
| 2005/0001176 A1 | 1/2005 | Loney et al. |
| 2005/0014201 A1 | 1/2005 | Deuthsch |
| 2005/0037343 A1 | 2/2005 | Fagnani et al. |
| 2005/0042685 A1 | 2/2005 | Albert et al. |
| 2005/0063863 A1 | 3/2005 | Columbus |
| 2005/0095582 A1 | 5/2005 | Gillim-Ross et al. |
| 2005/0105172 A1 | 5/2005 | Hasegawa et al. |
| 2005/0112589 A1 | 5/2005 | Hahn et al. |
| 2005/0118640 A1 | 6/2005 | Kureshy et al. |
| 2005/0123445 A1 | 6/2005 | Blecka et al. |
| 2005/0158804 A1 | 7/2005 | Yao et al. |
| 2005/0164236 A1 | 7/2005 | Su et al. |
| 2005/0181463 A1 | 8/2005 | Rao et al. |
| 2005/0214173 A1 | 9/2005 | Facer et al. |
| 2005/0265815 A1 | 12/2005 | Rodi |
| 2005/0277125 A1 | 12/2005 | Benn et al. |
| 2006/0037915 A1 | 2/2006 | Strand et al. |
| 2006/0040274 A1 | 2/2006 | Tsinberg |
| 2006/0040407 A1 | 2/2006 | Falcovitz-Gerassi et al. |
| 2006/0050142 A1 | 3/2006 | Scott et al. |
| 2006/0115380 A1 | 6/2006 | Kagan et al. |
| 2006/0128006 A1 | 6/2006 | Gerhardt et al. |
| 2006/0141045 A1 | 6/2006 | Bhatt et al. |
| 2006/0147959 A1 | 7/2006 | Bell et al. |
| 2006/0153736 A1* | 7/2006 | Kalra ................ B01L 3/508 422/400 |
| 2006/0160243 A1 | 7/2006 | Tang et al. |
| 2006/0257992 A1 | 11/2006 | McDevitt et al. |
| 2006/0263250 A1 | 11/2006 | Blouin et al. |
| 2007/0025882 A1 | 2/2007 | Zuppiger et al. |
| 2007/0026381 A1 | 2/2007 | Huang et al. |
| 2007/0053800 A1 | 3/2007 | Lehto |
| 2007/0111302 A1 | 5/2007 | Handique et al. |
| 2007/0154960 A1 | 7/2007 | Connelly et al. |
| 2007/0161051 A1 | 7/2007 | Tsinberg et al. |
| 2007/0172903 A1 | 7/2007 | Toner et al. |
| 2007/0238089 A1 | 10/2007 | Rosenthal et al. |
| 2007/0243523 A1 | 10/2007 | Ionescu-Zanetti et al. |
| 2007/0252265 A1 | 11/2007 | Sander |
| 2007/0264675 A1 | 11/2007 | Toner et al. |
| 2007/0264705 A1 | 11/2007 | Dodgson |
| 2007/0275418 A1 | 11/2007 | Hollmann et al. |
| 2008/0003224 A1 | 1/2008 | Fong et al. |
| 2008/0014589 A1 | 1/2008 | Link et al. |
| 2008/0020453 A1 | 1/2008 | Ehben et al. |
| 2008/0038231 A1 | 2/2008 | Rodgerson et al. |
| 2008/0068588 A1 | 3/2008 | Hess et al. |
| 2008/0090239 A1 | 4/2008 | Shoemaker et al. |
| 2008/0096212 A1 | 4/2008 | Bell et al. |
| 2008/0113358 A1 | 5/2008 | Kapur et al. |
| 2008/0113906 A1 | 5/2008 | Ding et al. |
| 2008/0124726 A1 | 5/2008 | Monforte |
| 2008/0182273 A1 | 7/2008 | Hansen et al. |
| 2008/0206751 A1 | 8/2008 | Squirrell et al. |
| 2008/0207615 A1 | 8/2008 | Bell et al. |
| 2008/0220422 A1 | 9/2008 | Shoemaker et al. |
| 2008/0234264 A1 | 9/2008 | Bell et al. |
| 2008/0240539 A1 | 10/2008 | George et al. |
| 2008/0248043 A1 | 10/2008 | Babcook et al. |
| 2008/0257735 A1 | 10/2008 | Jeon et al. |
| 2008/0317325 A1 | 12/2008 | Ortyn et al. |
| 2009/0014360 A1 | 1/2009 | Toner et al. |
| 2009/0061450 A1 | 3/2009 | Hunter |
| 2009/0075361 A1 | 3/2009 | Delouise et al. |
| 2009/0081773 A1 | 3/2009 | Kaufman |
| 2009/0139311 A1* | 6/2009 | Lehto ................ B01L 7/00 73/864.91 |
| 2009/0141593 A1 | 6/2009 | Taha |
| 2009/0153844 A1 | 6/2009 | Peter et al. |
| 2009/0158823 A1 | 6/2009 | Kaduchak et al. |
| 2009/0162853 A1 | 6/2009 | Clark et al. |
| 2009/0215088 A1 | 8/2009 | Forsyth et al. |
| 2009/0220979 A1* | 9/2009 | Davis ................ B03C 1/286 435/308.1 |
| 2009/0221059 A1 | 9/2009 | Williams et al. |
| 2009/0258383 A1 | 10/2009 | Kovac et al. |
| 2009/0275115 A1 | 11/2009 | Jury et al. |
| 2009/0317836 A1 | 12/2009 | Kuhn et al. |

(56) References Cited

U.S. PATENT DOCUMENTS

| | | |
|---|---|---|
| 2010/0003666 A1 | 1/2010 | Lee et al. |
| 2010/0087325 A1 | 4/2010 | Buermann |
| 2010/0120077 A1 | 5/2010 | Daridon |
| 2010/0127168 A1 | 5/2010 | Khursheed |
| 2010/0173394 A1 | 7/2010 | Colston et al. |
| 2010/0210009 A1 | 8/2010 | Willson et al. |
| 2010/0227387 A1 | 9/2010 | Safar et al. |
| 2010/0232675 A1 | 9/2010 | Ortyn et al. |
| 2010/0233693 A1 | 9/2010 | Kopf-Sill et al. |
| 2010/0255471 A1 | 10/2010 | Clarke et al. |
| 2010/0261179 A1 | 10/2010 | Betley et al. |
| 2010/0291584 A1 | 11/2010 | Tseng et al. |
| 2010/0304485 A1 | 12/2010 | Karnik et al. |
| 2010/0304978 A1 | 12/2010 | Robbins et al. |
| 2010/0328652 A1* | 12/2010 | Forrer .................. G01N 21/41 356/128 |
| 2011/0003380 A1 | 1/2011 | Miltenyi et al. |
| 2011/0005932 A1 | 1/2011 | Jovanovich et al. |
| 2011/0030808 A1 | 2/2011 | Chiou et al. |
| 2011/0045994 A1 | 2/2011 | Voldman et al. |
| 2011/0053151 A1 | 3/2011 | Hansen et al. |
| 2011/0053152 A1 | 3/2011 | Goldkorn et al. |
| 2011/0104718 A1 | 5/2011 | Rao et al. |
| 2011/0117634 A1 | 5/2011 | Halamish et al. |
| 2011/0143964 A1 | 6/2011 | Zhou et al. |
| 2011/0220567 A1 | 9/2011 | Kreuwel et al. |
| 2011/0227558 A1 | 9/2011 | Mannion et al. |
| 2011/0236904 A1 | 9/2011 | Hauch et al. |
| 2011/0280467 A1 | 11/2011 | George et al. |
| 2012/0021456 A1 | 1/2012 | Levine et al. |
| 2012/0071355 A9 | 3/2012 | Cooney |
| 2012/0071643 A1 | 3/2012 | Helfer et al. |
| 2012/0129190 A1 | 5/2012 | Chiu et al. |
| 2012/0152369 A1 | 6/2012 | Hiddessen et al. |
| 2012/0156675 A1 | 6/2012 | Lueerssen et al. |
| 2012/0164679 A1 | 6/2012 | Vrouwe et al. |
| 2012/0194805 A1 | 8/2012 | Ness et al. |
| 2012/0270310 A1 | 10/2012 | Spence et al. |
| 2012/0309104 A1 | 12/2012 | Uematsu et al. |
| 2012/0316074 A1 | 12/2012 | Saxonov |
| 2013/0011832 A1 | 1/2013 | Moreno et al. |
| 2013/0090778 A1 | 4/2013 | Brill |
| 2013/0116102 A1 | 5/2013 | Hansen |
| 2013/0130376 A1 | 5/2013 | Serobyan et al. |
| 2013/0136670 A1 | 5/2013 | Wiltsie |
| 2013/0140183 A1 | 6/2013 | Tajima |
| 2013/0142711 A1 | 6/2013 | Wilson et al. |
| 2013/0171628 A1 | 7/2013 | Di et al. |
| 2013/0171728 A1 | 7/2013 | Simard |
| 2013/0183660 A1 | 7/2013 | Yu et al. |
| 2013/0190212 A1 | 7/2013 | Handique et al. |
| 2013/0203634 A1 | 8/2013 | Jovanovich et al. |
| 2013/0210126 A1 | 8/2013 | Williams et al. |
| 2013/0210127 A1* | 8/2013 | Williams ................ C12Q 1/68 435/287.2 |
| 2013/0230860 A1 | 9/2013 | Park et al. |
| 2013/0244906 A1 | 9/2013 | Collins |
| 2013/0259635 A1 | 10/2013 | Maslana et al. |
| 2013/0287645 A1 | 10/2013 | Shaikh et al. |
| 2013/0309778 A1 | 11/2013 | Lowe et al. |
| 2014/0030717 A1 | 1/2014 | Zhong et al. |
| 2014/0051595 A1 | 2/2014 | So |
| 2014/0087370 A1 | 3/2014 | Maeshima |
| 2014/0155295 A1 | 6/2014 | Hindson et al. |
| 2014/0161686 A1 | 6/2014 | Bort et al. |
| 2014/0173443 A1 | 6/2014 | Hawkins et al. |
| 2014/0212881 A1 | 7/2014 | Handique et al. |
| 2014/0213487 A1 | 7/2014 | Freudenthal et al. |
| 2014/0220617 A1 | 8/2014 | Yung et al. |
| 2014/0272965 A1 | 9/2014 | Handique et al. |
| 2014/0276216 A1 | 9/2014 | Lipinsky et al. |
| 2014/0315237 A1 | 10/2014 | Masujima et al. |
| 2014/0329301 A1 | 11/2014 | Handique |
| 2014/0357511 A1 | 12/2014 | Handique et al. |
| 2014/0370612 A1 | 12/2014 | Bassler et al. |
| 2015/0011432 A1 | 1/2015 | Saxonov |
| 2015/0056663 A1 | 2/2015 | Tajima et al. |
| 2015/0089359 A1 | 3/2015 | Brisebois |
| 2015/0093306 A1 | 4/2015 | Thorne et al. |
| 2015/0133319 A1 | 5/2015 | Fu et al. |
| 2015/0160135 A1 | 6/2015 | Tibbe et al. |
| 2015/0160931 A1 | 6/2015 | Glazer et al. |
| 2015/0204864 A1 | 7/2015 | Fan et al. |
| 2015/0225714 A1 | 8/2015 | Takahashi et al. |
| 2015/0253251 A1 | 9/2015 | McKee et al. |
| 2015/0299784 A1 | 10/2015 | Fan et al. |
| 2015/0376609 A1 | 12/2015 | Hindson et al. |
| 2016/0008814 A1 | 1/2016 | Handique et al. |
| 2016/0023213 A1 | 1/2016 | Richardson |
| 2016/0024572 A1 | 1/2016 | Shishkin et al. |
| 2016/0024761 A1 | 1/2016 | Korb |
| 2016/0053253 A1 | 2/2016 | Salathia et al. |
| 2016/0060621 A1 | 3/2016 | Agresti et al. |
| 2016/0108464 A1 | 4/2016 | Saxonov et al. |
| 2016/0130649 A1 | 5/2016 | Xie et al. |
| 2016/0199838 A1 | 7/2016 | Handique et al. |
| 2016/0202157 A1 | 7/2016 | Fawcett et al. |
| 2016/0209319 A1 | 7/2016 | Adalsteinsson et al. |
| 2016/0251714 A1 | 9/2016 | Conant et al. |
| 2016/0289669 A1 | 10/2016 | Fan et al. |
| 2016/0314242 A1 | 10/2016 | Schnall-Levin et al. |
| 2016/0367991 A1 | 12/2016 | Petersen et al. |
| 2017/0044525 A1 | 2/2017 | Kaper et al. |
| 2017/0052205 A1 | 2/2017 | Silbert |
| 2017/0073405 A1 | 3/2017 | Fuh et al. |
| 2017/0153219 A1 | 6/2017 | Handique et al. |
| 2017/0276682 A1 | 9/2017 | Park |
| 2017/0307502 A1 | 10/2017 | Mason et al. |
| 2017/0320038 A1 | 11/2017 | Husain et al. |
| 2017/0321252 A1 | 11/2017 | Hindson et al. |
| 2017/0335385 A1 | 11/2017 | Hindson et al. |
| 2017/0356027 A1 | 12/2017 | Hindson et al. |
| 2017/0370951 A1 | 12/2017 | Buffiere et al. |
| 2018/0030515 A1 | 2/2018 | Regev et al. |
| 2018/0036731 A1 | 2/2018 | Handique et al. |
| 2018/0037942 A1 | 2/2018 | Fu |
| 2018/0051321 A1 | 2/2018 | Hindson et al. |
| 2018/0080075 A1 | 3/2018 | Brenner et al. |
| 2018/0088112 A1 | 3/2018 | Fan et al. |
| 2018/0094298 A1 | 4/2018 | Hindson et al. |
| 2018/0094312 A1 | 4/2018 | Hindson et al. |
| 2018/0105808 A1 | 4/2018 | Mikkelsen et al. |
| 2018/0112266 A1 | 4/2018 | Hindson et al. |
| 2018/0127744 A1 | 5/2018 | Hu et al. |
| 2018/0127823 A1 | 5/2018 | Shekhar et al. |
| 2018/0272296 A1 | 9/2018 | Link et al. |
| 2018/0274027 A1 | 9/2018 | Hindson et al. |
| 2018/0282804 A1 | 10/2018 | Hindson et al. |
| 2018/0311636 A1 | 11/2018 | Jacobson et al. |
| 2018/0372741 A1 | 12/2018 | Matsumoto et al. |
| 2019/0002814 A1* | 1/2019 | Masquelier ............ C12M 23/44 |
| 2019/0060902 A1 | 2/2019 | Handique et al. |
| 2019/0064168 A1 | 2/2019 | Handique et al. |
| 2019/0076847 A1* | 3/2019 | Donovan ................ B01L 9/52 |
| 2019/0106739 A1 | 4/2019 | Terbrueggen |
| 2019/0153532 A1 | 5/2019 | Bharadwaj et al. |
| 2019/0241944 A1 | 8/2019 | Cater et al. |
| 2019/0285644 A1 | 9/2019 | Regev et al. |
| 2019/0338353 A1 | 11/2019 | Belgrader et al. |
| 2020/0209229 A1 | 7/2020 | Strong et al. |
| 2021/0171939 A1 | 6/2021 | McCoy et al. |
| 2021/0252509 A1 | 8/2021 | Szita et al. |
| 2025/0033046 A1* | 1/2025 | Williamson ....... G01N 35/1011 |

FOREIGN PATENT DOCUMENTS

| | | |
|---|---|---|
| CN | 103998394 A | 8/2014 |
| CN | 104508492 A | 4/2015 |
| CN | 104789468 A | 7/2015 |
| EP | 2414548 A2 | 2/2012 |
| EP | 2414548 B1 | 10/2015 |
| JP | 2006098696 A | 4/2006 |
| JP | 2008136415 A | 6/2008 |
| JP | 2009195160 A | 9/2009 |

(56) References Cited

FOREIGN PATENT DOCUMENTS

| | | | |
|---|---|---|---|
| JP | 2010085343 A | 4/2010 | |
| JP | 2011127965 A | 6/2011 | |
| JP | 2011234671 A | 11/2011 | |
| JP | 2013500496 A | 1/2013 | |
| JP | 2013541959 A | 11/2013 | |
| JP | 2015527588 A | 9/2015 | |
| JP | 5998218 B2 | 9/2016 | |
| JP | 2017063716 A | 4/2017 | |
| JP | 2018508187 A | 3/2018 | |
| JP | 2019516099 A | 6/2019 | |
| KR | 20170137655 A | 12/2017 | |
| WO | 9942832 A1 | 8/1999 | |
| WO | 2003035909 A2 | 5/2003 | |
| WO | 2006098696 A1 | 9/2006 | |
| WO | 2007044917 A2 | 4/2007 | |
| WO | WO-2008004695 A1 * | 1/2008 | ........... B01L 3/5082 |
| WO | 2008061165 A2 | 5/2008 | |
| WO | 2009076560 A2 | 6/2009 | |
| WO | 2010120818 A2 | 10/2010 | |
| WO | 2010142954 A1 | 12/2010 | |
| WO | 2011017094 A2 | 2/2011 | |
| WO | 2011162290 A1 | 12/2011 | |
| WO | 2012057548 A2 | 5/2012 | |
| WO | WO-2013176767 A1 * | 11/2013 | ........ B01L 3/502715 |
| WO | 2014007074 A1 | 1/2014 | |
| WO | 2015133337 A1 | 9/2015 | |
| WO | 2015150278 A1 | 10/2015 | |
| WO | 2016115025 A1 | 7/2016 | |
| WO | 2016149639 A1 | 9/2016 | |
| WO | 2016151719 A1 | 9/2016 | |
| WO | 2016162997 A1 | 10/2016 | |
| WO | 2016191533 A1 | 12/2016 | |
| WO | 2017095917 A1 | 6/2017 | |
| WO | 2017184242 A2 | 10/2017 | |
| WO | 2018013723 A1 | 1/2018 | |
| WO | 2018058073 A2 | 3/2018 | |
| WO | 2019006436 A1 | 1/2019 | |
| WO | 2019046307 A1 | 3/2019 | |
| WO | 2019104337 A1 | 5/2019 | |
| WO | 2019165318 A1 | 8/2019 | |

OTHER PUBLICATIONS

Weisstein, Eric W., "Circle Packing", From MathWorld—A Wolfram Web Resource, https://mathworld.wolfram.com/CirclePacking.html, 4 pages, Aug. 25, 2012.

"High-throughput imaging of a unique continuous flow microfluidics plate", Scikon Innovation, Application Note, May 2016, https://www.moleculardevices.com/en/assets/app-note/dd/img/high-throughput-imaging-of-a-unique-continuous-flow-microfluidics-plate#gref.

Chen, H. , et al., "High-throughput, deterministic single cell trapping and long-term clonal cell culture in microfluidic devices", Lab Chip. Feb. 21, 2015;15(4):1072-83. doi: 10.1039/c4lc01176g. PMID: 25519528.

Dura, Burak , et al., "scFTD-seq: freeze-thaw lysis based, portable approach toward highly distributed single-cell 3' mRNA profiling", Nucleic Acids Research, 2019, vol. 47, No. 3, published online Nov. 20, 2018.

Guo, P. , et al., "Microfluidic capture and release of bacteria in a conical nanopore array", Lab Chip. vol. 12, p. 558-561, 2012, published online Nov. 2011.

Lindstrom, Sara , "Microwell devices for single-analyses", Royal Institute of Technology, Stockholm, Sweden, 2009, pp. 1-80., Feb. 12, 2018 00:00:00.0.

Murphy, Travis W., et al., "Recent advances in the use of microfluidic technologies for signs;e cell analysis", Analyst, Oct. 26, 2017, vol. 143, pp. 60-80.

Sarkar, S. , et al., "Phenotypic drug profiling in droplet microfluidics for better targeting of drug-resistant tumors", Lab on a chip., vol. 15, 23 (2015): 4441-50. doi:10.1039/c5lc00923e.

Seale, K. T. , et al., "Mirrored pyramidal wells for simultaneous multiple vantage point microscop", Journal of Microscopy (2008) 232 1-6. (Year: 2008).

Shaminie, Jairaman , et al., "Improvement in the detection rate of t(14;18) translocation on paraffin-embedded issue: combination approach using PCR and FISH", Pathology, Oct. 2003, 35(5), pp. 414-421.

Stahl, Patrik L., et al., "Visualization and analysis of gene expression in tissue sections by spatial transcriptomics", sciencemag.org, Jul. 2016, vol. 353, Issue 6294, pp. 78-82.

Sugio, Yoshihiro , "An agar-based on-chip neural-cell-cultivation system for stepwise control of network pattern generation during cultivation", Sensors and Actuators B 99 2004 156-162., Apr. 4, 2017 00:00:00.0.

Tan, Wei-Heang , et al., "A trap-and-release integrated microfluidic system for dynamic microarray applications", PNAS (2007) 104 1146-1151. (Year: 2007).

Tan, Wei-Heang , et al., "A trap-and-release integrated microfluidic system for dynamic microarray applications", Supplemental information from Tan et al. PNAS (2007) 104. (Year: 2007).

Yeh, EC , et al., "Self-powered integrated microfluidic point-of-care low-cost enabling (SIMPLE) chip", Sci Adv. Mar. 22, 2017;3(3):e1501645. doi:10.1126/sciadv.1501645. PMID: 28345028; PMCID: PM 5362183.

Yuan, J. , et al., "An Automated Microwell Platform for Large-Scale Single Cell RNA-Seq.", Sci Rep. Sep. 27, 2016;6:33883. doi: 10.1038/srep33883. PMID: 27670648; PMCID: PMC5037380.

* cited by examiner (ELEVATION VIEW, CROSS-SECTION)

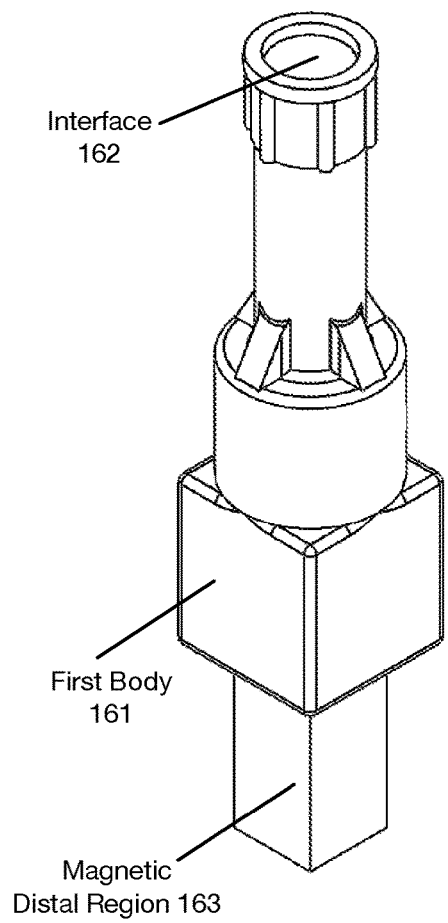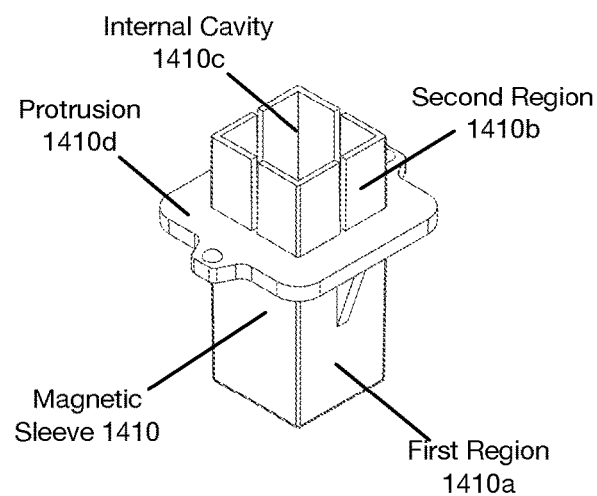
FIGURE 10B
FIGURE 10C (SIDE VIEW)

SYSTEM AND METHOD FOR AUTOMATED SINGLE CELL PROCESSING

CROSS-REFERENCE TO RELATED APPLICATIONS

This application is a continuation of U.S. application Ser. No. 16/867,256, filed 5 May 2020, which claims the benefit of U.S. Provisional Application No. 62/844,470, filed on 7 May 2019 and U.S. Application 62/866,726, filed on 26 Jun. 2019, which are each incorporated in its entirety herein by this reference.

TECHNICAL FIELD

This invention relates generally to the cell capture and cell processing field, and more specifically to a new and useful automated system and method for single cell capture and processing in the cell capture and cell processing field.

BACKGROUND

With an increased interest in cell-specific drug testing, diagnosis, and other assays, systems and methods that allow for individual cell isolation, identification, and retrieval are becoming highly desirable. Single cell capture systems and methods have been shown to be particularly advantageous for these applications. However, associated processes and protocols for single cell capture and subsequent analysis often must be performed in a particular order and with a high precision in order to properly maintain the cells. As such, these processes can be time consuming for the user, as well as result in damage to the cells or otherwise unfavorable results if they are not performed properly (e.g., through mistakes in pipetting, through a mix-up of reagents, etc.). In particular, these novel high throughput single cell cytometry assays have great utility in translational medicine, personalized therapy selections, clinical diagnostics, and/or other applications of use, but lack of automation prevents proper performance by novice users, thereby limiting throughput.

Thus, there is a need in the cell capture and cell processing field to create a new and useful system and method for single cell capture and processing.

BRIEF DESCRIPTION OF THE FIGS.

FIGS. 10A-10C depict variations of a first subset of components used for material separation in a system for automated single cell sample processing;

DESCRIPTION OF THE PREFERRED EMBODIMENTS

Figure 1A:
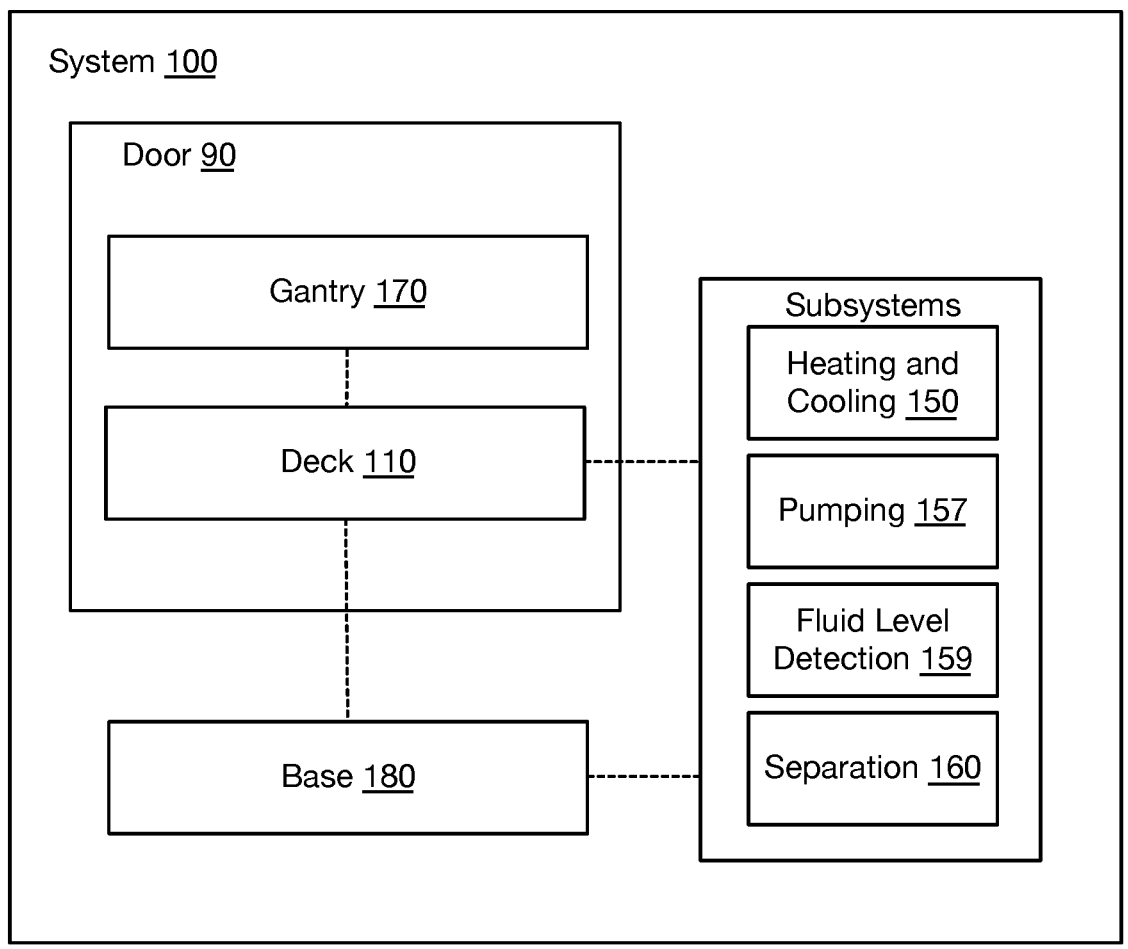
FIGS. 1A-1D depict schematic representations of an embodiment of a system for automated single cell sample processing.

The following description of the preferred embodiments of the invention is not intended to limit the invention to these preferred embodiments, but rather to enable any person skilled in the art to make and use this invention.

1. Benefits

The invention(s) can confer several benefits over conventional systems and methods.

In particular, the invention(s) confer(s) the benefit of enabling at least partial automation of the protocols involved in single cell capture and subsequent processing, thereby optimizing run success and consistency. In more detail, the user can be removed from part or all of the method (e.g. loading samples, capping lids, on-instrument lysis, reverse transcription processes, cDNA amplification, bead or cDNA product retrieval, on-instrument library preparation and cleanup, etc.). Further, the system and/or method can enable better accuracy of a protocol over conventional systems and methods (e.g. better accuracy in the addition of the correct reagents, better temperature control of reagents, rapid processing of critical liquid handling steps, precise incubation times, optimal bead washing and separation, automated bar code reading, etc.). Further, the system and/or method can confer the benefit of preventing accidents (e.g. knocking the system, spills of reagents, contamination of sample or instrument, etc.), which can commonly occur during the manual performance of a protocol.

Additionally, through use of limited-use and/or preloaded and unitized reagent cartridges, the system and/or method can confer the benefit of providing a streamlined user experience with optimized quality control and design architecture to accommodate on-going development of assays and future applications. As such, the system confers the benefit of independent or nearly independent control of reagents or reagent groups. In a specific example of this variation, the system includes a reagent cartridge having any or all of the following dedicated regions: a room temperature region, a cooling region, a heating region, a magnetic region (e.g., overlapping with a heating region), waste capture region, intermediate reagent parking region or any other suitable region. In a related benefit, the system and/or method can confer the benefit of enabling the user to purchase smaller volumes of reagents, such as through the distribution of reagents in protocol-specific types and quantities to be used in accordance with specific automated protocols. This can function to save costs, reduce reagent waste, or have any other suitable outcome.

Additionally, through use of fluid handling and separation elements (e.g., magnetic separation components), the system and/or method can confer the benefit of providing automated sample and library cleanup steps. Relatedly, the system and/or method can confer the benefit of establishing better fluid flow throughout the system. In a first example, this is enabled through an automated pipetting system (e.g., pipettor, gantry, and assorted pipette tips), which can monitor and/or direct fluid flow (e.g., to maintain an optimal flow rate, to establish an optimal volume of reagents, etc.) without user intervention. The fluid handling system components for single cell preparation and/or other assays may involve use of both of (a) liquid pipettor coupled to a gantry for fluidic dispensing and pumping into a fluidic channel or fluidic reservoir (e.g., of a sample processing cartridge) and/or (b) a built-in on-chip pressurizable waste chamber connected and controlled through a valve integrated with the fluidic network, as described in more detail below. Such a combined dual liquid handling system gives unprecedented control of the flow (e.g., microliter per second to tens of milliliters per second), delivery (e.g., 1-100,000 microliters), and residence time (e.g., milliseconds to hours) of reagents through the fluidic system. Additionally or alternatively, the system can monitor and/or direct fluid flow with user intervention (e.g., with minimal user intervention, to encourage optimal user intervention, etc.).

Additionally, through software and workflow improvements, the system and/or method can minimize number of manual operations performed by a user, and provide relevant system status reports to ensure smooth operation and sample processing.

Additionally, in relation to sample processing disposables, the system and/or method can confer the benefit of consolidating multiple components in a manner that is scalable for disposables having a higher number of sample processing chambers. Additionally, the system can confer the benefit of consolidating two or more conventionally separate processing platform components into a single unit, which can reduce an overall size of the system (e.g., enable a benchtop model), reduce an overall footprint of a mechanism of the system (e.g., pipettor gantry), enable a more efficient transfer of materials among the system, or perform any other suitable function. In a specific example of this variation, an inlet, set of microwells, outlet valve, lid mechanism (e.g., lid of the lid mechanism, full lid mechanism, etc.) and waste chamber are all localized to a single piece.

Additionally, the invention(s) address needs in low parameter flow applications, high parameter flow applications, mass cytometry applications, proteogenomic applications, single cell RNA applications, protein detection applications, single cell multi-omic applications and other applications, by allowing standard users with various skill levels (e.g., novices, experts) to operate platform components. Specific workflows implemented by embodiments of the system are described in more detail below.

In relation to performance, the system and/or method can process cells to generate purified libraries within a day, perform next generation sequencing (NGS) preparation, and perform other processes in a streamlined process (e.g., by a set of dedicated consumables including an efficiently loaded reagent cartridge, a sample processing cartridge, and a container of fluid handling disposables).

Additionally, the system confers the benefit of three-dimensional mobility of a component, such as a pipettor. In a specific example of this variation, the system includes a gantry providing X-Y-Z mobility for a pipettor, enabling the pipettor to perform a variety of tasks (e.g., piercing foil coverings of reagent tubes, transferring materials among a set of wells, etc.) in an automated fashion.

Additionally or alternatively, the system and/or method can confer any other suitable benefit.

2. System

As shown in FIGS. 1A-1D, an embodiment of a system 100 for automated single cell capture and processing includes: a deck no supporting and positioning a set of sample processing elements; a gantry 170 for actuating tools for interactions with the set of sample processing elements supported by the deck no; and a base 180 supporting various processing subsystems and a control subsystems in communication with the processing subsystems, wherein the control subsystems control states of the deck 110, the set of sample processing elements, and the gantry 170 in order to transition the system 100 between various operation modes. Embodiments, variations, and examples of operation modes, which provide various workflows, are described in further detail in Section 3 below.

Embodiments of the system 100 function to enable automated single cell capture and any or all of associated processing of the captured cells. In more detail, the user can be removed from part or all of the method (e.g. loading samples, capping lids, on-instrument lysis, reverse transcription processes, cDNA amplification, bead or cDNA product retrieval, on-instrument library preparation and cleanup, etc.). The system can additionally or alternatively function to enhance the accuracy (e.g. by minimizing manual processes) of cell capture and sample processing protocols. Additionally, through use of limited-use and/or pre-loaded reagent cartridges, the system 100 can provide a streamlined user experience with optimized quality control and design architecture to accommodate on-going development of assays and future applications. As such, the system confers the benefit of independent or nearly independent control of reagents or reagent groups. In a specific example of this variation, the system includes a reagent cassette having any or all of the following dedicated regions: a room temperature region, a cooling region, a heating/thermo-cycling region, a magnetic region (e.g., overlapping with a heating region), a region to provide a cell sample input, a region for prepared library output or any other suitable region. In a related benefit, the system and/or method can confer the benefit of enabling the user to purchase smaller volumes of reagents, such as through the distribution of reagents in protocol-specific types and quantities to be used in accordance with specific automated protocols. This can function to save costs, reduce reagent waste, or have any other suitable outcome.

Additionally, through use of fluid handling and separation elements (e.g., magnetic separation components), embodiments of the system 100 can function to provide automated sample and library cleanup steps. Relatedly, the system 100 can confer the benefit of establishing better fluid flow throughout the system. In a first example, this is enabled through an automated pipetting system (e.g., pipettor, gantry, and assorted pipette tips), which can monitor and/or direct fluid flow (e.g., to maintain an optimal flow rate, to establish an optimal volume of reagents, etc.) without or with minimal user intervention.

Additionally, the system 100 can enable low parameter flow applications, high parameter flow applications, mass cytometry applications, proteogenomic applications, single cell RNA applications, protein detection applications, and other applications, by allowing standard users with various skill levels (e.g., novices, experts) to operate platform components. Furthermore, in relation to performance, the system 100 can process cells or other biological material to rapidly generate purified libraries, perform next generation sequencing (NGS) preparation, and perform other processes in a streamlined process (e.g., by a set of dedicated consumables including an efficiently loaded reagent cartridge, a sample processing cartridge, and a container of fluid handling disposables).

In specific embodiments, the system 100 can comply with use requirements including one or more of: providing automated processes for nucleic acid library preparation, ability to provide quality control at desired points of a run, providing complete and single use kits for various assays, providing validated and locked protocols, providing alignment and retention of various system components, providing means for monitoring and controlling system operation (e.g., with a touch display), providing remote monitoring capabilities, providing sample processing within 24 hours, providing visual and/or audible system notifications, providing the ability to be cleaned with standard laboratory cleaners and without disassembly, fitting on a standard laboratory bench, providing easy installation, providing assay materials with stable shelf life, returning reports of maintenance history, providing data storage (e.g., in relation to external storage media, in relation to cloud storage, etc.), providing training, and providing other suitable functions according to various requirements.

As described above, in relation to sample processing, embodiments of the system 100 can include or be configured to process cells, cell-derived material, and/or other biological material (e.g., cell-free nucleic acids). The cells can include any or all of mammalian cells (e.g., human cells, mouse cells, etc.), embryos, stem cells, plant cells, or any other suitable kind of cells. The cells can contain target material (e.g., target lysate, mRNA, RNA, DNA, etc.) which originates within the cells and is optionally captured by the cell capture system for processing. Additionally, the containers containing the cells can be prepared from multiple cell-containing samples (e.g., 12 samples, 24 samples, 48 samples, 96 samples, 384 samples, 1536 samples, other numbers of samples), wherein the various samples are hashed or barcoded prior to mixing them together into a single container (or reduced number of containers). This feature enables automated processing of multiple samples in the same automated run for their respective single cell preparation and library preparation operations. Additionally or alternatively, the system 100 can be configured to interact with particles (e.g., beads, probes, nucleotides, oligonucleotides, polynucleotides, etc.), droplets, encapsulated cells, encapsulated biomarkers, reagents, or any other suitable materials.

The system can further additionally or alternatively include any or all of the system components as described in U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; U.S. application Ser. No. 15/815,532, filed 16 Nov. 2017; U.S. application Ser. No. 16/115,370, filed 28 Aug. 2018, U.S. application Ser. No. 16/564,375, filed 9 Sep. 2019, and U.S. application Ser. No. 16/816,817, filed 12 Mar. 2020, which are each incorporated in their entirety by this reference.

2.1 System: Deck

As shown in FIGS. 1A-1D, the deck 110 functions as a platform to support and position one or more components of the system 100 (e.g., at a top broad surface, at a top and bottom broad surface, at a side surface, etc.) for automated sample processing. Furthermore, the deck 110 can function to position one or more components of the system 100 to align with or otherwise interact with fluid processing subsystems, heating subsystems, separation subsystems (e.g., magnetic separation subsystems), and/or other subsystems coupled to the gantry 170 and/or base 180, as described below. In this regard, the deck 110 can be stationary as a reference platform, while other components are actuated into position for interacting with elements of the deck 110. Alternatively, the deck 110 can be coupled to one or more actuators for positioning elements of the deck 110 for interactions with other subsystems.

In the embodiment shown in FIGS. 1A-1D, the deck 110 provides a platform supporting the set of sample processing elements, where the sample processing elements can include disposable and/or reusable components, where the components include containers for containing sample processing materials and/or tools for processing samples (e.g., in relation to fluid handling, in relation to material separation, in relation to heating and cooling, etc.). In embodiments, the deck 110 can support a set of sample processing elements including one or more units of: a reagent cartridge 120, a sample processing cartridge 130, a tool container 140, a heating and cooling subsystem 150, a pumping subsystem 157, a fluid level detection subsystem 159, and a separation subsystem 160. Additionally or alternatively, the deck 110 can include other suitable components (e.g., fluorescence detection subsystems, confocal microscope subsystems, spectroscopic detection subsystems, Total Internal Reflection Fluorescence (TIRF) subsystems, Nuclear Magnetic Resonance (NMR) subsystems, Raman Spectroscopy (RS) RS subsystems, etc.).

The sample processing elements can be supported in a co-planar manner by the deck 110, or alternatively at different planes. Preferably, discrete elements supported by the deck are non-overlapping, but alternative embodiments of the deck 110 can support the sample processing elements in an overlapping manner (e.g., for conservation of space, etc., for operational efficiency, etc.).

Figure 1B:
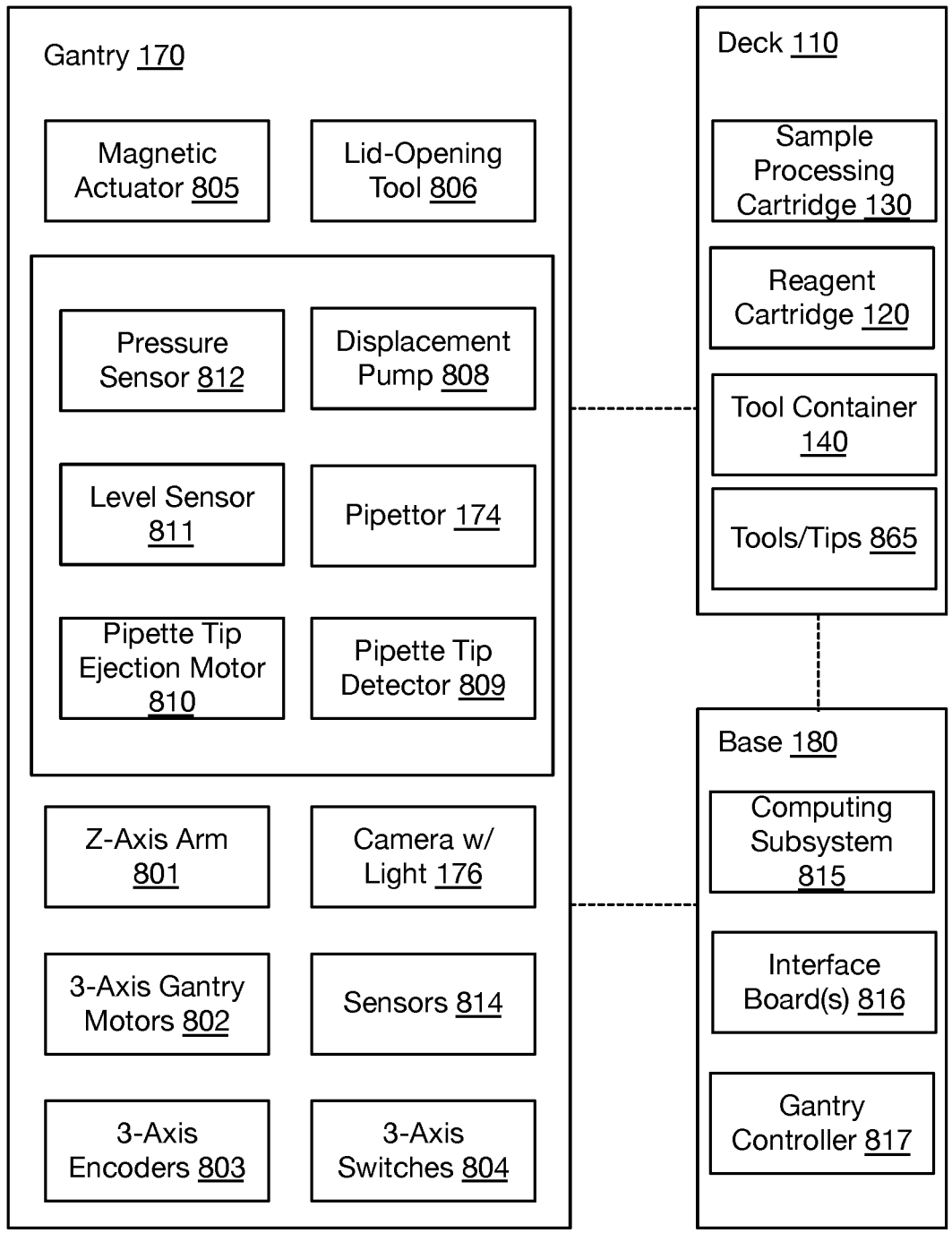
Figure 1C:
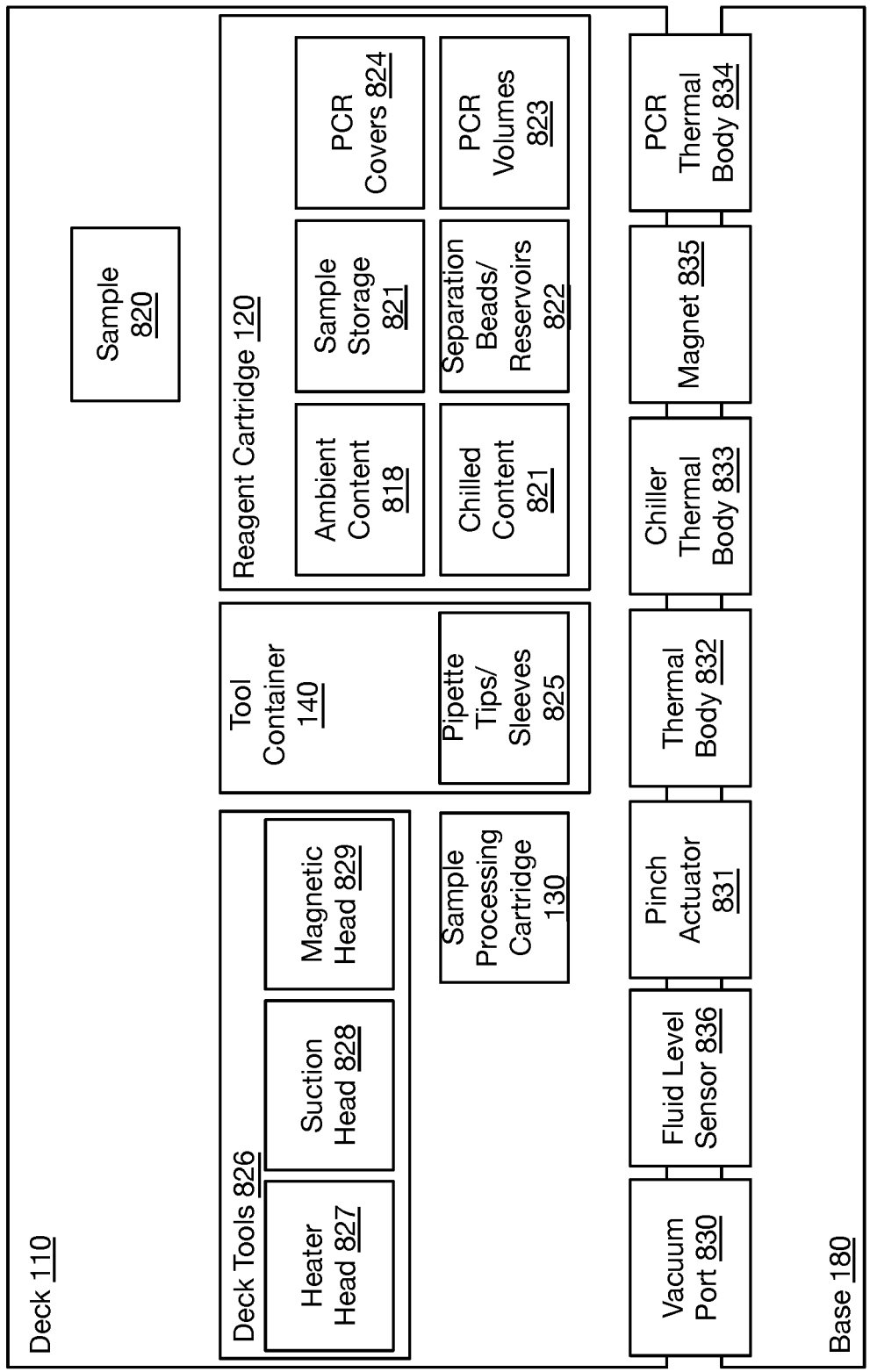
Figure 1D:
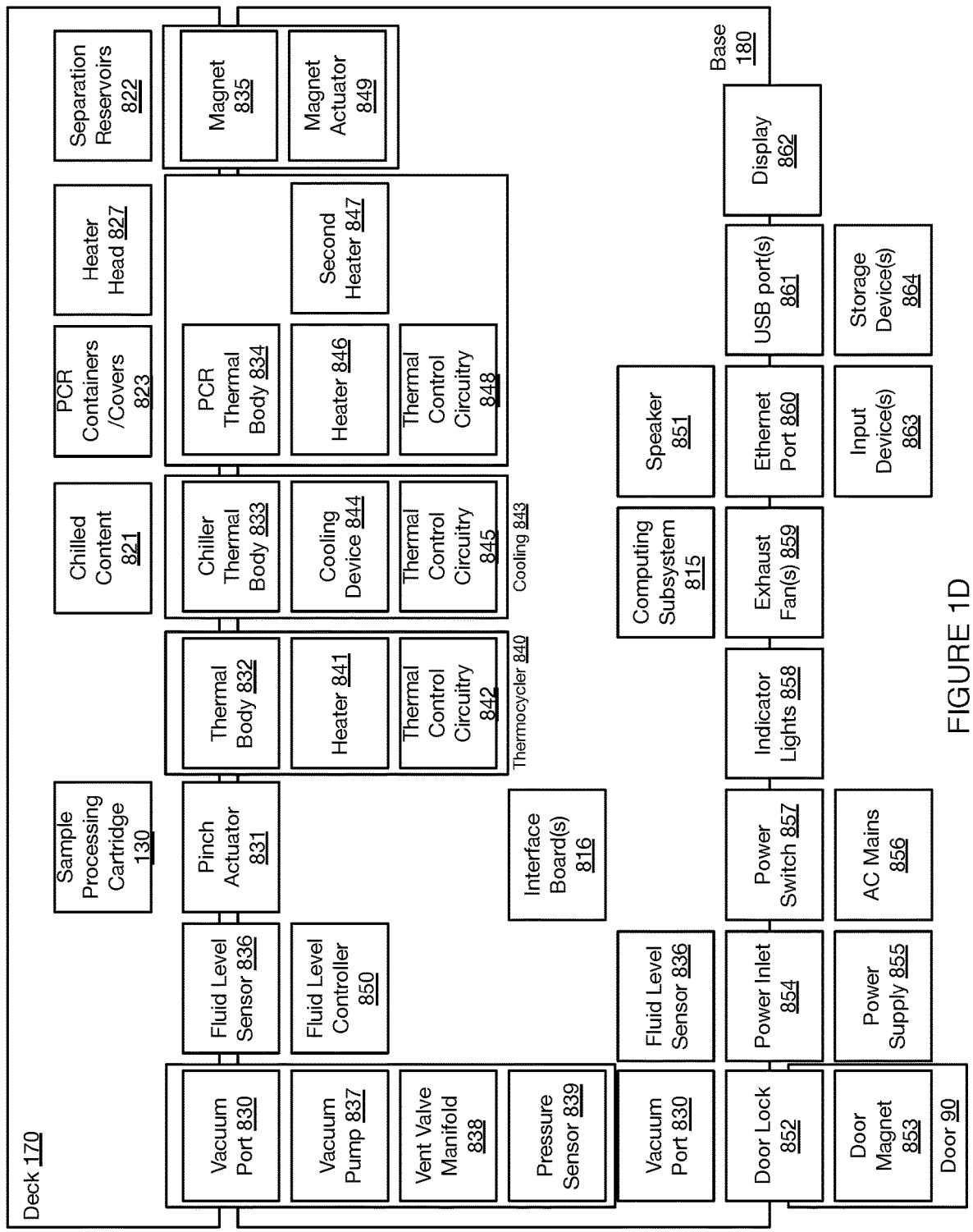

As shown in FIGS. 1A and 1D, the deck 110 can be accessible by door 90, where the door 90 of the system 100 can transition between open and/or closed modes in order to provide access to the deck 110 and elements supported by the deck 110. However, in other variations, the deck 110 may not be accessible by door 90.

Details of embodiments, variations, and examples of elements supported by the deck 110 are further described in Sections 2.1.1 through 2.1.5 below.

2.1.1 Deck-Supported Element: Reagent cartridge

The deck 110 includes at least one region 111 (shown in FIGS. 2A and 2B) for supporting a unit of the reagent cartridge 120, where the region 111 functions to position the reagent cartridge 120 relative to portions of the heating and cooling subsystem 150, and separation subsystem 160 described in more detail below. In this regard, the region 111 can include one or more openings, recesses, and/or protrusions for providing interfaces between complementary portions of the reagent cartridge 120 and associated portions of the heating and cooling subsystem 150 and separation subsystem 160, and additionally to promote and maintain alignment between such portions.

The reagent cartridge 120 functions to contain, in one or more compartments, materials for cell capture and/or processing of samples according to one or more workflows for various applications. As such, the reagent cartridge 120 can define a set of storage volumes distributed across a set of domains, where the set of domains can be configured for providing suitable environments for the material contents of each domain. The set of storage volumes can directly contain sample processing materials, and/or can alternatively be configured to receive and maintain positions of individual containers (e.g., tubes, etc.) that contain sample processing materials. The storage volumes of each domain can be distributed in arrays, or otherwise arranged. Storage volumes can have circular cross sections, rectangular cross sections, or other morphologies (e.g., cross sections, widths, depths, etc.) depending upon application of use (e.g., cold storage, heat transfer, magnetic separation, etc.).

The set of domains can additionally or alternatively be configured to provide modularity, where one or more domains can be pre-packaged with materials that are stable over longer shelf lives, while other domains can be configured to receive materials that have short shelf lives (e.g., immediately prior to use). The set of domains can additionally or alternatively be configured to promote operational efficiency (e.g., in relation to grouping similar materials, etc.) for apparatuses that interact with materials of the reagent cartridge 120. The set of domains can additionally or alternatively define regions for receiving and/or processing material (e.g., nucleic acid material) extracted from the sample processing cartridge 130 described in more detail below.

Additionally or alternatively, domains of the set of domains can be separate (e.g. domain for receiving heat is separate from domains that are intended for other storage temperatures or applications requiring different temperatures), overlapping, or otherwise arranged. Domains of the set of domains can additionally or alternatively be distinguished from each other by a morphology (e.g., length of the storage volumes of each domain, depth of storage volumes for accessing or interfacing with other elements of the deck, width or depth of domains configured for efficient heat transfer, etc.). In some variations, the set of domains can further include at least one domain supporting an absorbent or porous material pad that can be used for receiving drips of fluid (e.g., from a tip of a pipettor, described below) during processing. The internal surface properties for certain domains (e.g., for PCR reactions, for magnetic separation, etc.) may be configured with high surface polish to enable low binding or retention of biomolecules (e.g., nucleic acids or proteins). The various domains may also be mixed and matched to provide a large number of available assays to the customers.

Individual storage volumes of the set of storage volumes of the reagent cartridge 120 can further include one or more seals, which function to isolate materials within the reagent cartridge 120, to prevent cross-contamination between materials within individual storage volumes, to prevent contaminants from entering individual storage volumes, and/or to prevent evaporative loss during storage and shipment. The seal(s) can be puncturable seal(s) (e.g., composed of paper, composed of a metal foil, and/or composed of any other suitable material). However, the seal(s) can alternatively be configured to be non-puncturable (e.g., the seal(s) can be configured to peel away from the reagent cartridge 120). In embodiments, certain reagent containers may also be sealed by a hinged lid that can be opened or closed by a tool (e.g., as described in more detail below), as needed for processing at appropriate steps of the protocol.

In variations, the set of domains can include a first domain for storing reagents requiring a chilled environment (e.g., at a temperature from 1C-15C), a second domain for storing materials that can be stored in ambient conditions, a third domain storing tubes with materials for performing polymerase chain reaction (PCR) operations and interfacing with heating elements described below, a fourth domain for storing functionalized particles (e.g., beads with probes having barcoding regions and other functional regions, as described in U.S. application Ser. No. 16/115,370, etc.), and a fifth domain for performing separation operations (e.g., separation of target from non-target material by magnetic force). In variations, domains providing different environments for the storage volumes can be configured differently. For instance, the first domain (i.e., for cold storage) can be composed of a thermally insulating material and/or can include insulating material about storage volumes of the domain (e.g., individually, about the entire domain). Additionally or alternatively, a domain for separation can be include magnetically conductive materials configured to provide proper magnetic field characteristics for separation. Additionally or alternatively, domains for thermocycling or other heat transfer applications can be configured with thermally conductive materials to promote efficient heat transfer to and from the reagent cartridge. In embodiments, various domains can be optimally positioned such that there is minimal cross-talk between certain operations. For example, the domain(s) for chilled reagent storage volumes can be maintained a temperature (e.g., 4C) during a run, whereas the domain(s) for PCR reactions can require heating (e.g., up to 95C during denature). As such, to minimize the effect of PCR thermocycling on chilled reagents, the domain(s) containing the reagents stored at ambient temperature may be configured in between the PCR thermocycling domain(s) and chilled domain(s). In order to further prevent heat cross-talk, additional buffer tubes with just air may be used in between critical domains that need independent temperature control.

In variations, process materials supported by the domains of the reagent cartridge 120 can include one or more of: buffers (e.g. ethanol, priming buffer, lysis buffer, custom lysis buffers, sample wash buffers, saline with RNAase inhibitors, bead wash buffers, RT buffer, buffer, etc.), oils (e.g. perfluorinert oil), PCR master mixtures, cells, beads (e.g. functionalized beads) or any other suitable materials used for cell capture and/or sample processing. Additionally or alternatively, one or more of the set of storage volumes can be empty (e.g. initially empty, empty throughout one or more processes, empty prior to filling by an operator, etc.). Different storage regions in various domains of the reagent cartridge can have initial reagent volumes from a few microliters (e.g., 5 microliters) to 50 milliliters. Additional details of process materials and applications of use are described below in relation to workflows of Section 3.

Figure 3A:
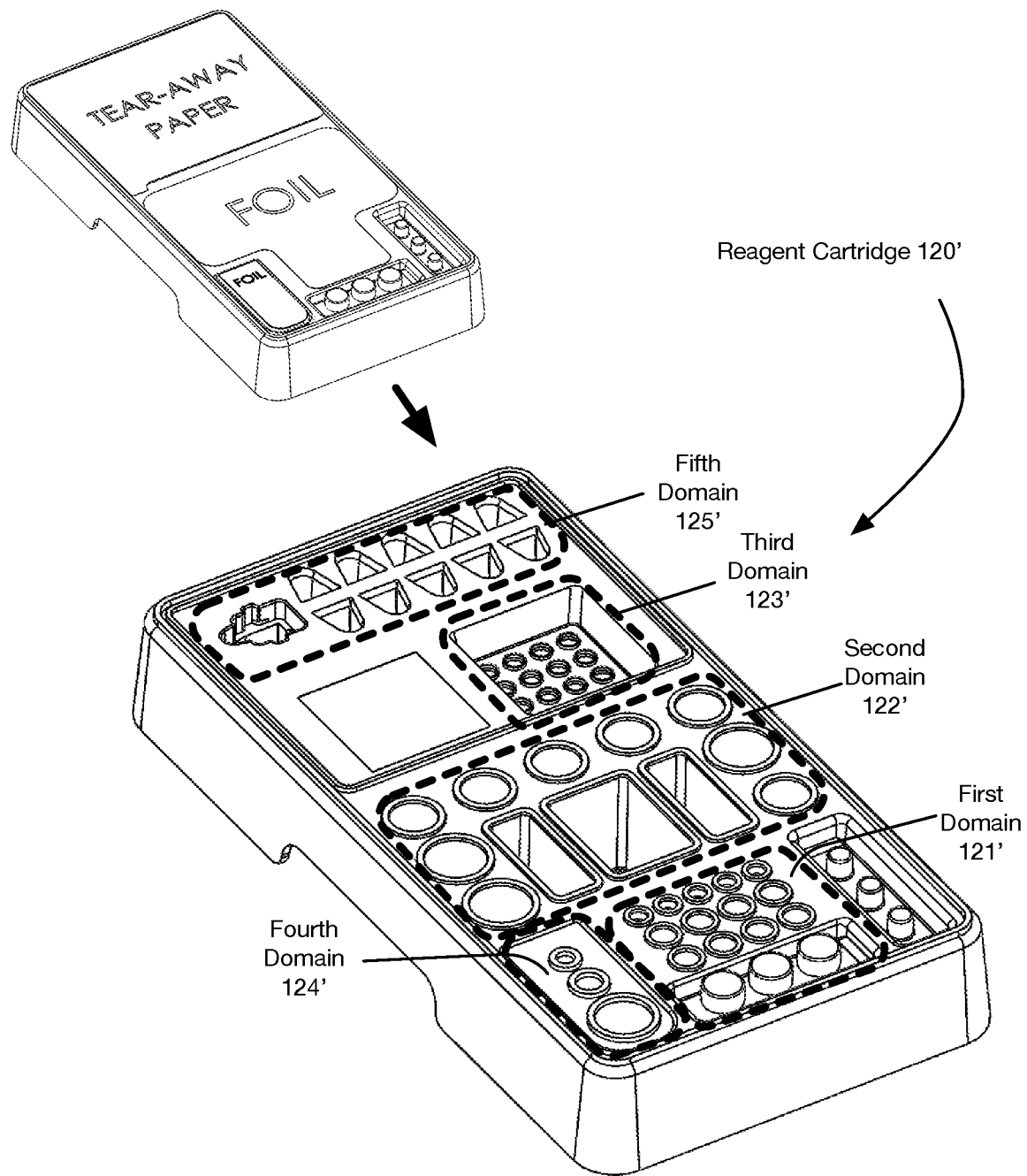
FIGS. 3A-3C depict variations of a reagent cartridge associated with a system for automated single cell sample processing.

In a specific example, as shown in FIG. 3A, the reagent cartridge 120' includes a first domain 121' at a first peripheral region of the reagent cartridge 120' for storing reagents requiring a chilled environment, a second domain 122' at a central region of the reagent cartridge 120' for storing materials that can be stored in ambient conditions, a third domain 123' at a peripheral region of the cartridge, near the second domain 122, for storing tubes with materials for performing polymerase chain reaction (PCR) operations, a fourth domain 124' at a peripheral region of the reagent cartridge 120', for storing functionalized particles (e.g., beads with probes having barcoding regions and other functional regions, as described in U.S. application Ser. No. 16/115,370, etc.), and a fifth domain 125' at a peripheral region of the reagent cartridge 120' for performing separation operations (e.g., separation of target from non-target material by magnetic force). In the specific example, the fourth domain 124' can be a modular element, whereby the fourth domain 124' can be stored separately from the rest of the reagent cartridge 120' until the functionalized particles are ready for use, at which point the fourth domain 124' is set in position and coupled with the reagent cartridge 120'.

In the specific example, the first domain 121' and the second domain 122' are covered by a first seal composed of a metal foil, the third domain 123' and the fifth domain 125' are covered by a second seal composed of a paper, and the fourth domain 124' is covered by a third seal composed of a metal foil. However, variations of the example of the reagent cartridge 120' can be configured in another suitable manner.

Figure 3B:
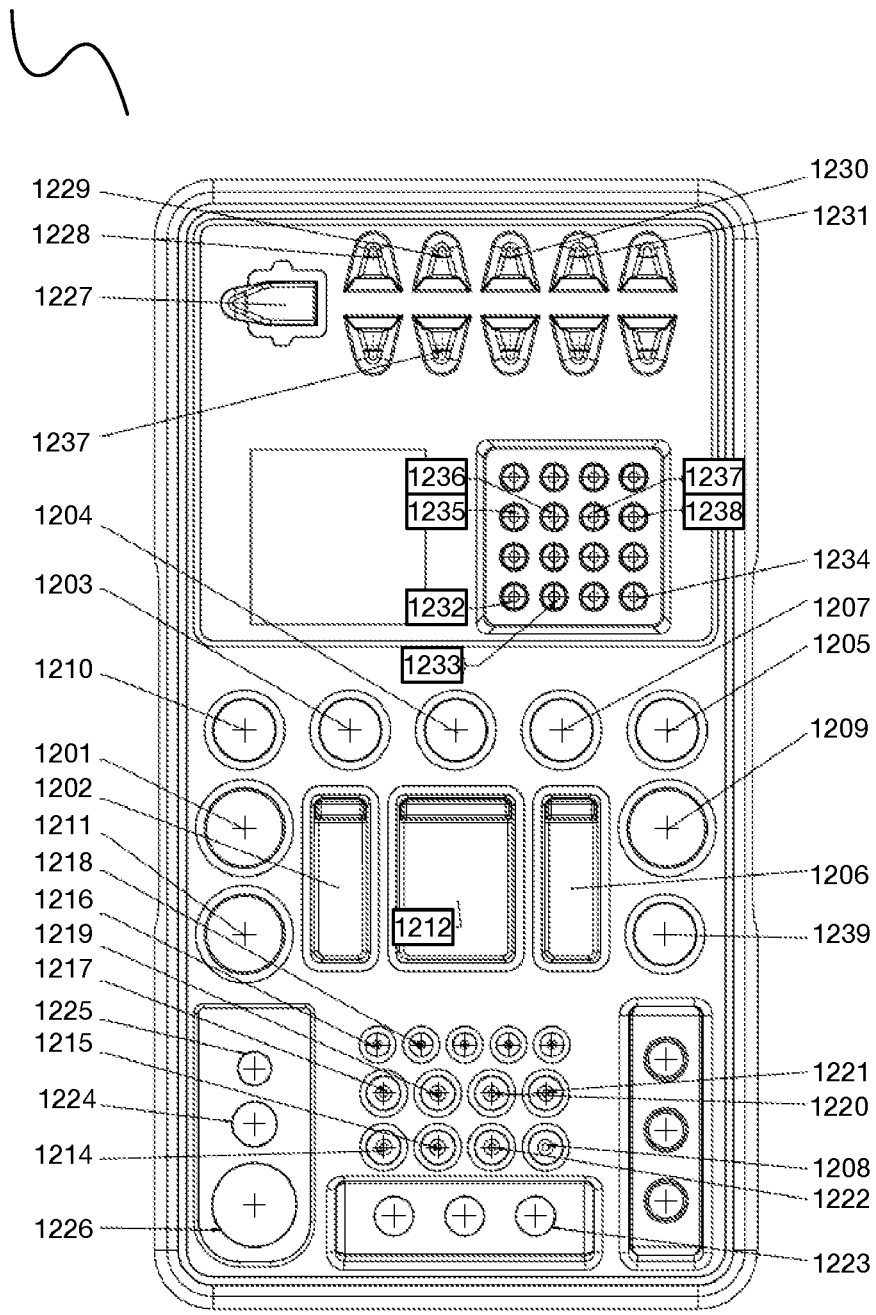

In another specific example for a 3.1. RNA processing protocol (e.g., corresponding to the workflow of Section 3.1. below) shown in FIG. 3B, the reagent cartridge 120" can include: a first storage volume 1201 (e.g., having a volume of 4.46 mL) for 100% molecular grade ethanol; a second storage volume 1202 (e.g., having a volume of 6.6 mL) for a first wash buffer; a third storage volume 1203 (e.g., having a volume of 1.1 mL) for a particle binding buffer; a fourth storage volume 1204 (e.g., having a volume of 1.1 mL) for a lysis buffer; a fifth storage volume 1205 (e.g., having a volume of 1.1 mL) for perfluorinert oil; a sixth storage volume 1206 (e.g., having a volume of 6.63 mL) for a particle binding wash solution; a seventh storage volume 1207 (e.g., having a volume of 1.1 mL) for a pre RT reaction wash buffer; an eighth storage volume 1208 (e.g., having a volume of 1 mL) for a 0.1M sodium hydroxide solution; a ninth storage volume 1209 (e.g., having a volume of 2.5 mL) for a second wash buffer; a tenth storage volume 1210 (e.g., having a volume of 1 mL) for mineral oil; an $11^{th}$ storage volume 1211 (e.g., having a volume of 1.1 mL) for 80% molecular grade ethanol; a $12^{th}$ storage volume 1212 (e.g., having a volume of 2.2 mL) for nuclease-free water; a $13^{th}$ storage volume 1213 (e.g., having a volume of 12.36 mL) for waste; a $14^{th}$ storage volume 1214 (e.g., having a volume of 0.15 mL) for 0.1M DTT; a $15^{th}$ storage volume 1215 for an RT cocktail without superscript IV: a $16^{th}$ storage volume 1216 (e.g., having a volume of 0.011 mL) for superscript IV enzyme; a $17^{th}$ storage volume 1217 (e.g., having a volume of 0.22 mL) for exonuclease buffer; an $18^{th}$ storage volume 1218 (e.g., having a volume of 0.022 mL) for exonuclease enzyme; a $19^{th}$ storage volume 1219 (e.g., having a volume of 0.128 mL) for a second strand synthesis mixture; a $20^{th}$ storage volume 1220 (e.g., having a volume of 0.072 mL) for a second strand synthesis primer; a $21^{st}$ storage volume 1221 (e.g., having a volume of 0.22 mL) for a PCR master mixture for mRNA amplification; a $22^{nd}$ storage volume 1222 (e.g., having a volume of 0.33 mL) for a mixture (e.g., Kapa Biosystems™ HiFi HotStart Ready Mixture (2×); a $23^{rd}$ storage volume 1223 (e.g., having a volume of 0.025 mL) for mRNA product; a $24^{th}$ storage volume 1224 (e.g., having a volume of 0.11 mL) for functionalized particles; a $25^{th}$ storage volume 1225 (e.g., having a volume of 0.03 mL) for magnetic retrieval particles; a $26^{th}$ storage volume 1226 (e.g., having a volume of 0.66 mL) for AMPure XP particles; $27^{th}$ storage volume 1227 for magnetic particle retrieval collection; a $28^{th}$ storage volume 1228 for magnetic particle preparation; a $29^{th}$ storage volume 1229 for magnetic particle second strand synthesis; a $30^{th}$ storage volume 1230 for magnetic particle retrieval post-PCR cDNA amplification; a $31^{st}$ storage volume 1231 for AMPure XP particle purification; a $32^{nd}$ storage volume 1232 for a first exonuclease treatment; a $33^{rd}$ storage volume 1233 for a second exonuclease treatment; a $34^{th}$ storage volume 1234 for second strand synthesis; a $35^{th}$ storage volume 1235 for a first cDNA amplification operation; a $36^{th}$ storage volume 1236 for a second cDNA amplification operation; a $37^{th}$ storage volume 1237 for a third cDNA amplification operation; a $38^{th}$ storage volume 1238 for a fourth cDNA amplification operation; and a $39^{th}$ storage volume 1239 for a cell suspension.

Figure 3C:
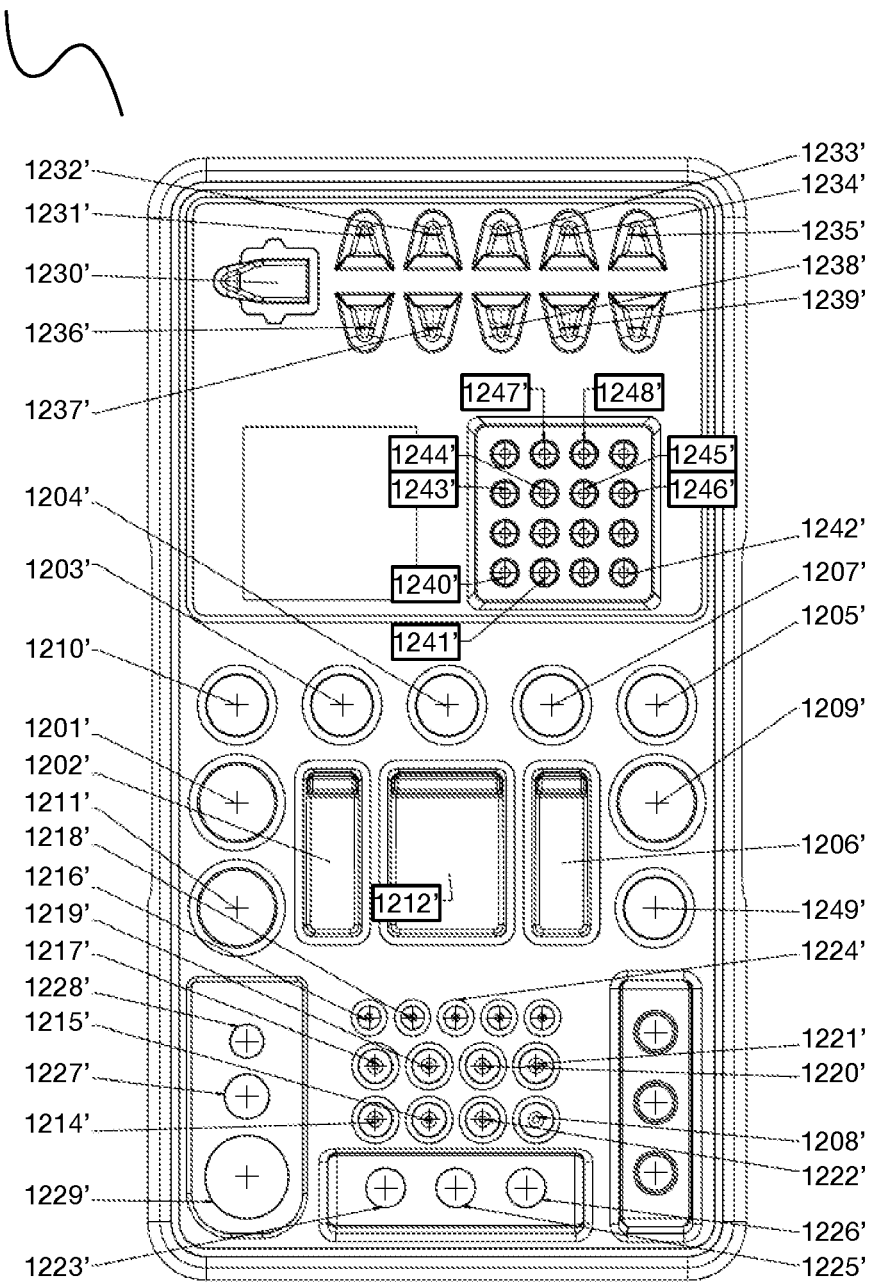

In another specific example for a CITE-Seq processing protocol (e.g., corresponding to workflow in Section 3.3 below) shown in FIG. 3C, the reagent cartridge 120''' can include: a first storage volume 1201' (e.g., having a volume of 4.46 mL) for 100% molecular grade ethanol; a second storage volume 1202' (e.g., having a volume of 6.6 mL) for a first wash buffer; a third storage volume 1203' (e.g., having a volume of 1.1 mL) for a particle binding buffer; a fourth storage volume 1204' (e.g., having a volume of 1.1 mL) for a lysis buffer; a fifth storage volume 1205' (e.g., having a volume of 1.1 mL) for perfluorinert oil; a sixth storage volume 1206' (e.g., having a volume of 6.63 mL) for a particle binding wash solution; a seventh storage volume 1207' (e.g., having a volume of 1.1 mL) for a pre RT reaction wash buffer; an eighth storage volume 1208' (e.g., having a volume of 1 mL) for a 0.1M sodium hydroxide solution; a ninth storage volume 1209' (e.g., having a volume of 2.5 mL) for a second wash buffer; a tenth storage volume 1210' (e.g., having a volume of 1 mL) for mineral oil; an $11^{th}$ storage volume 1211' (e.g., having a volume of 1.1 mL) for 80% molecular grade ethanol; a $12^{th}$ storage volume 1212' (e.g., having a volume of 2.2 mL) for nuclease-free water; a $13^{th}$ storage volume 1213' (e.g., having a volume of 12.36 mL) for waste; a $14^{th}$ storage volume 1214' (e.g., having a volume of 0.15 mL) for 0.1M DTT; a $15^{th}$ storage volume 1215' for an RT cocktail without superscript IV: a $16^{th}$ storage volume 1216' (e.g., having a volume of 0.011 mL) for superscript IV enzyme; a $17^{th}$ storage volume 1217' (e.g., having a volume of 0.22 mL) for exonuclease buffer; an $18^{th}$ storage volume 1218' (e.g., having a volume of 0.022 mL) for exonuclease enzyme; a $19^{th}$ storage volume 1219' (e.g., having a volume of 0.128 mL) for a second strand synthesis mixture; a $20^{th}$ storage volume 1220' (e.g., having a volume of 0.072 mL) for a second strand synthesis primer; a $21^{st}$ storage volume 1221' (e.g., having a volume of 0.22 mL) for a PCR master mixture for cDNA amplification; a $22^{nd}$ storage volume 1222' (e.g., having a volume of 0.33 mL) for a mixture (e.g., Kapa Biosystems™ HiFi HotStart Ready Mixture (2×); a $23^{rd}$ storage volume 1223' for an indexing primer; a $24^{th}$ storage volume 1224' (e.g., having a volume of 0.11 mL) for a PCR master mixture for mRNA amplification; a $25^{th}$ storage volume 1225' (e.g., having a volume of 0.2 mL) for ADT product; a $26^{th}$ storage volume 1226' (e.g., having a volume of 0.025 mL) for mRNA product; a $27^{th}$ storage volume 1227' (e.g., having a volume of 0.11 mL) for functionalized particles; a $28^{th}$ storage volume 1228' (e.g., having a volume of 0.03 mL) for magnetic retrieval particles; a $29^{th}$ storage volume 1229' (e.g., having a volume of 0.66 mL) for AMPure XP particles; $30^{th}$ storage volume 1230' for magnetic particle retrieval collection; a $31^{st}$ storage volume 1231' for magnetic particle preparation; a $32^{nd}$ storage volume 1232' for magnetic particle second strand synthesis; a $33^{rd}$ storage volume 1233' for magnetic particle retrieval post-PCR cDNA amplification; a $34^{th}$ storage volume 1234' for AMPure XP particle purification; a $35^{th}$ storage volume 1235' for a first antibody-derived tag purification operation; a $36^{th}$ storage volume 1236' for a second antibody-derived tag purification operation; a $37^{th}$ storage volume 1237' for AMPure XP particle ADT post-PCR purification; a $38^{th}$ storage volume 1238' for mRNA AMPure XP particle purification; a $39^{th}$ storage volume 1239' for mRNA AMPure XP particles post-PCR purification; a $40^{th}$ storage volume 1240' for a first exonuclease treatment; a $41^{st}$ storage volume 1241' for a second exonuclease treatment; a $42^{nd}$ storage volume 1242' for second strand synthesis; a $43^{rd}$ storage volume 1243' for a first cDNA amplification operation; a $44^{th}$ storage volume 1244' for a second cDNA amplification operation; a $45^{th}$ storage volume 1245' for a third cDNA amplification operation; a $46^{th}$ storage volume 1246' for a fourth cDNA amplification operation; a $47^{th}$ storage volume 1247' for antibody-derived tag fraction amplification; a $48^{th}$ storage volume 1248' for mRNA amplification; and a $49^{th}$ storage volume 1249' for a cell suspension.

2.1.2 Deck-Supported Element: Sample cartridge

Figure 2A:
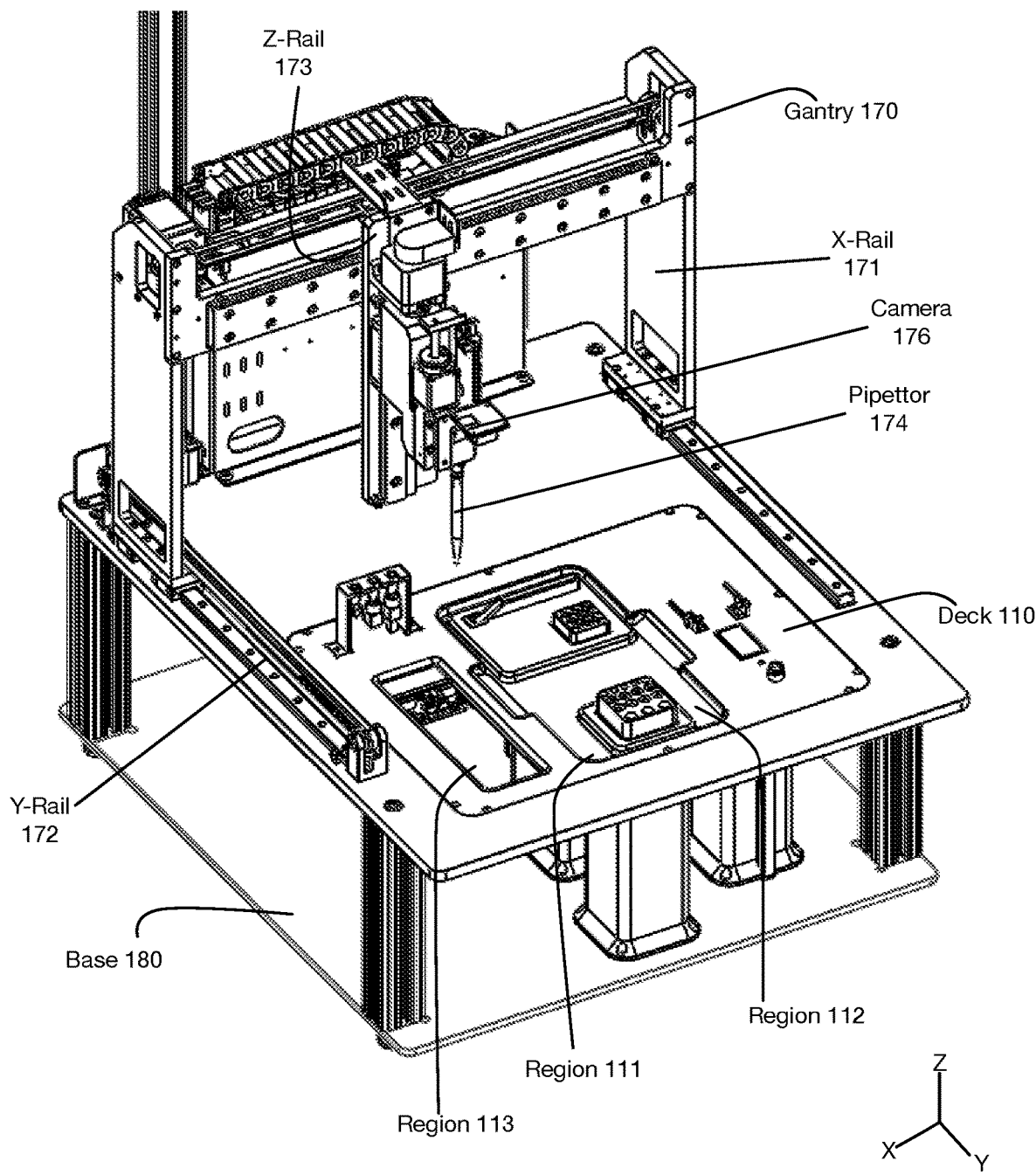
FIGS. 2A-2F depict views of a variation of the system shown in FIGS. 1A-1D.
Figure 2B:
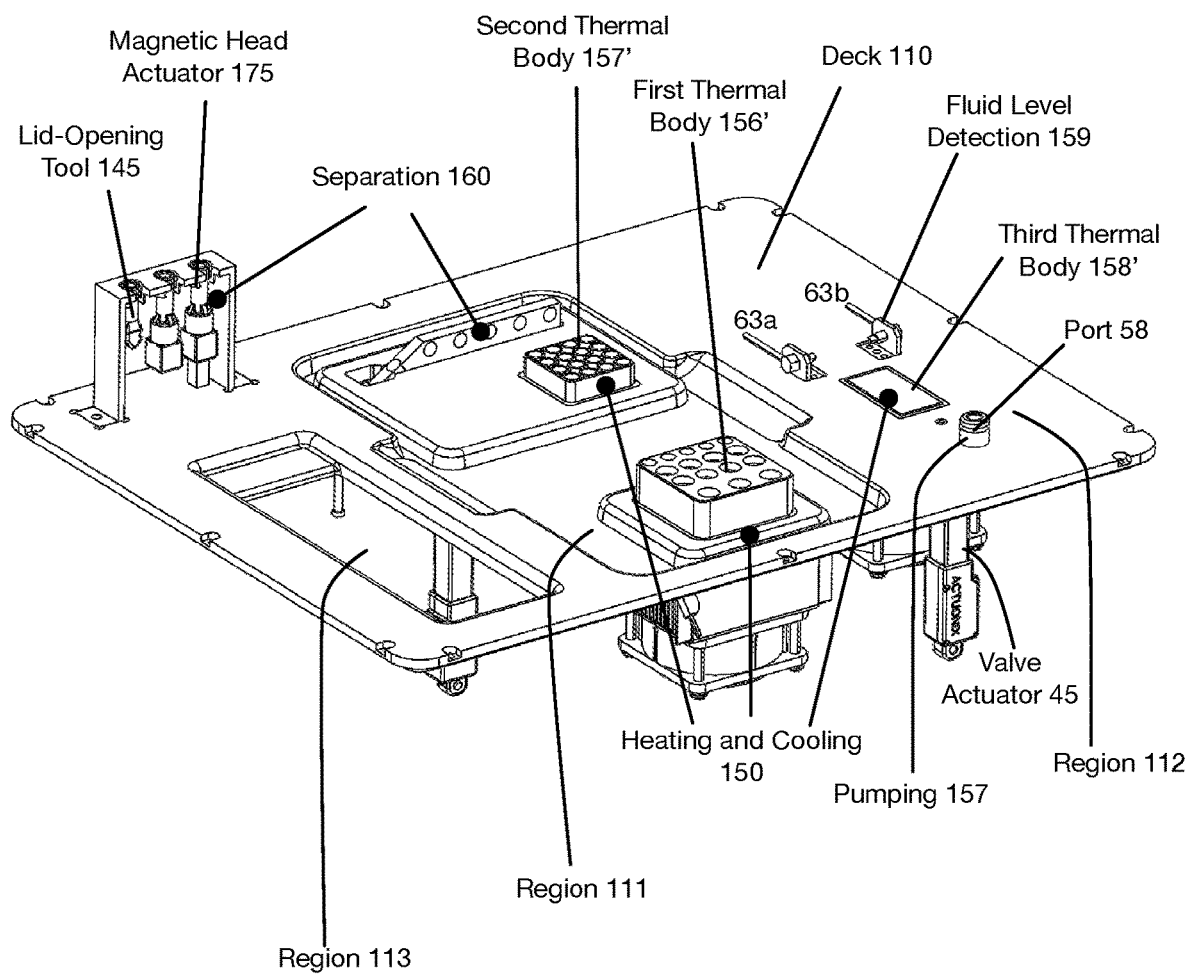
Figure 2C:
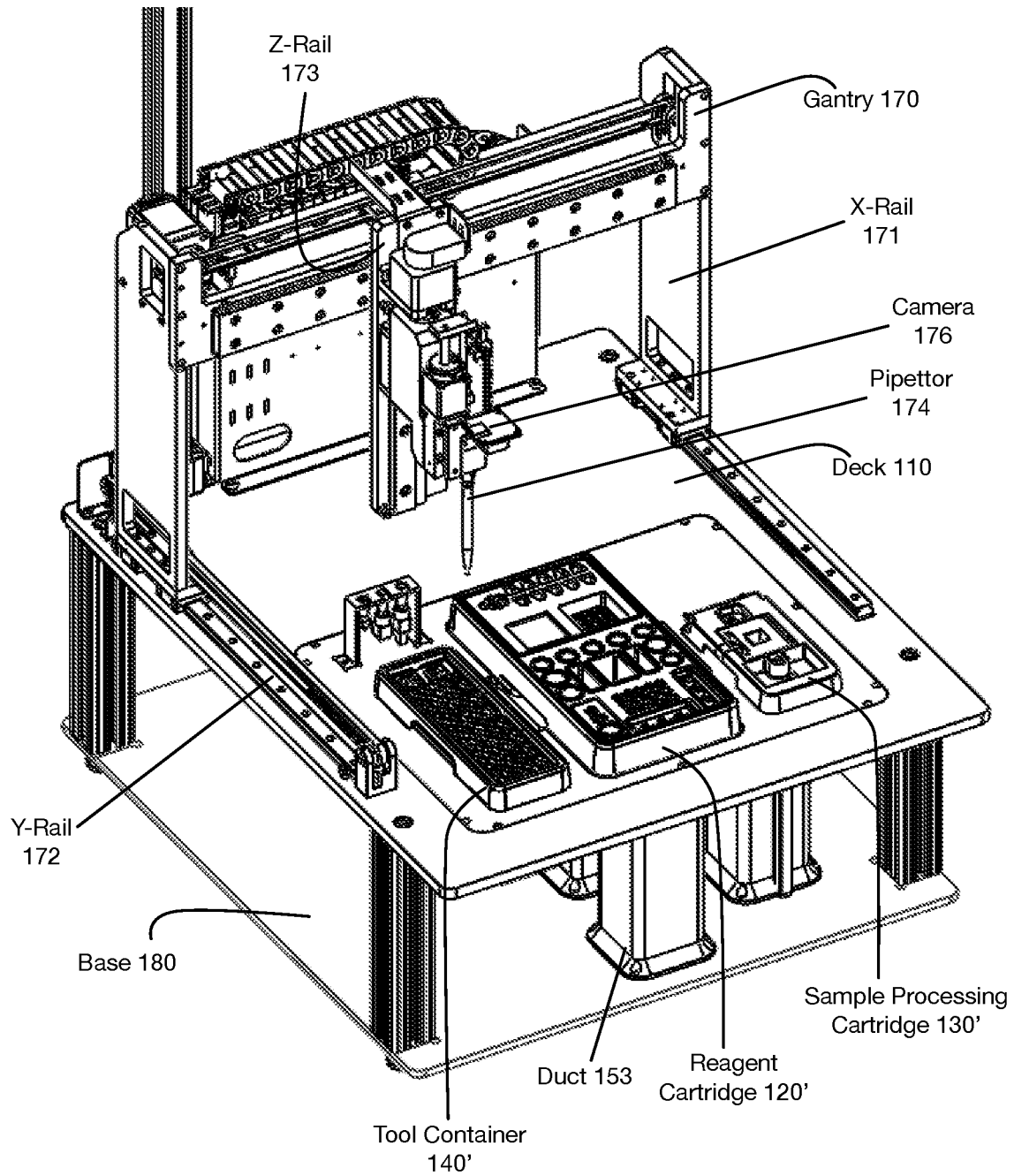

As shown in FIGS. 2A and 2B, the deck 110 also includes at least one region 112 for supporting a unit of the sample processing cartridge 130, where the region 112 functions to position the sample processing cartridge 130 relative to portions of the heating and cooling subsystem 150, the pumping subsystem 157, and the fluid level detection subsystem 159 described in more detail below. In this regard, the region 112 can include one or more openings, recesses, and/or protrusions for providing interfaces between complementary portions of the sample processing cartridge 130 and associated portions of the heating and cooling subsystem 150, the pumping subsystem 157, and the fluid level detection subsystem 159, and additionally to promote and maintain alignment between such portions.

The sample processing cartridge 130 functions to provide one or more sample processing regions in which cells are captured and optionally sorted, processed, or otherwise treated for downstream applications, where the downstream applications can be performed on the sample processing cartridge 130 (e.g., on-chip) and/or away from the sample processing cartridge 130 (e.g., off-chip). Portions of the sample processing cartridge 130 can be configured within a single substrate, but can additionally or alternatively include multiple portions (e.g. connected by fluidic pathways) across multiple substrates.

Figure 4A:
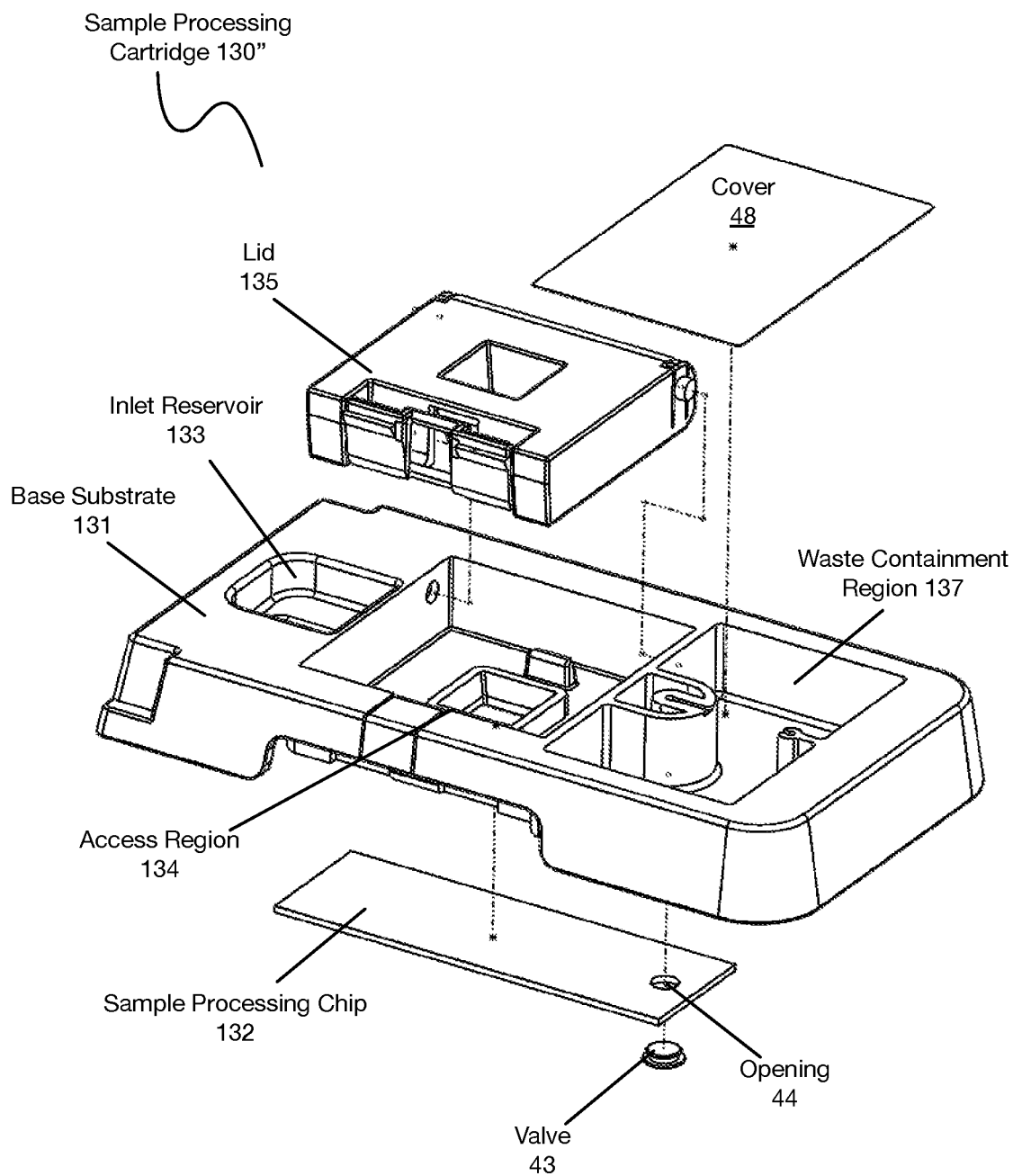
FIGS. 4A-4C depict views of a variation of a sample processing cartridge associated with a system for automated single cell sample processing.
Figure 4B:
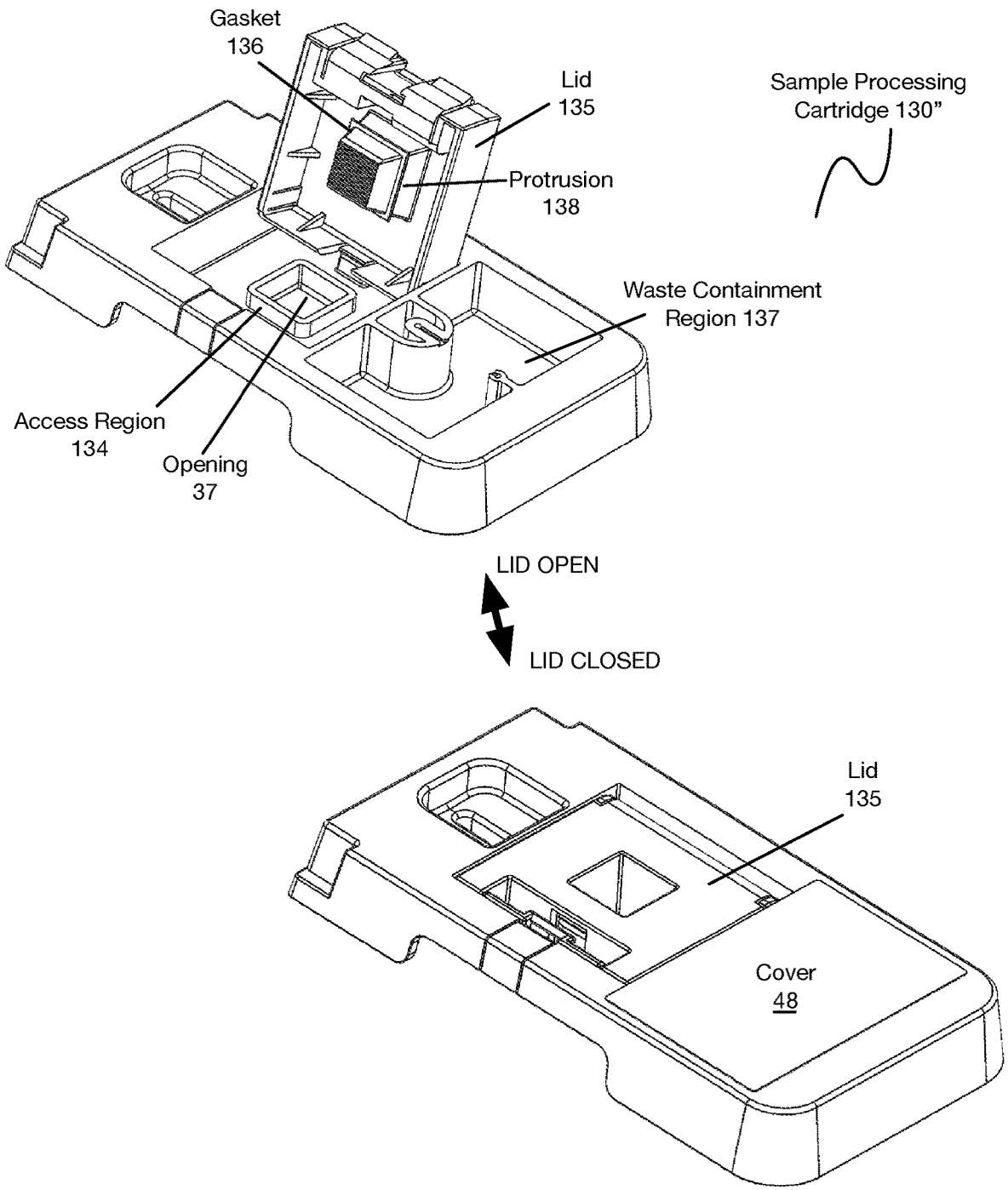
Figure 4C:
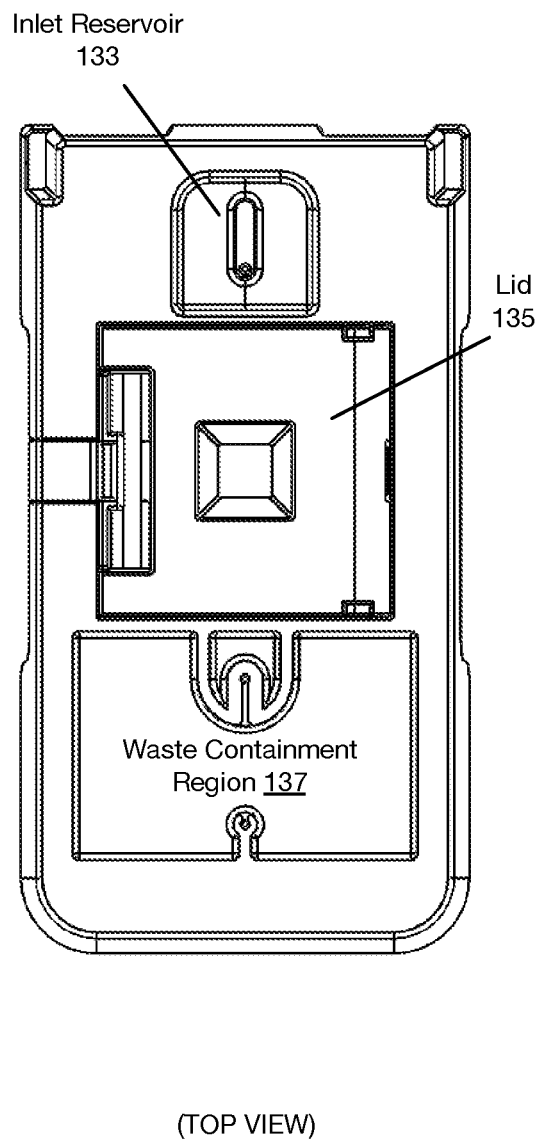
Figure 4C:
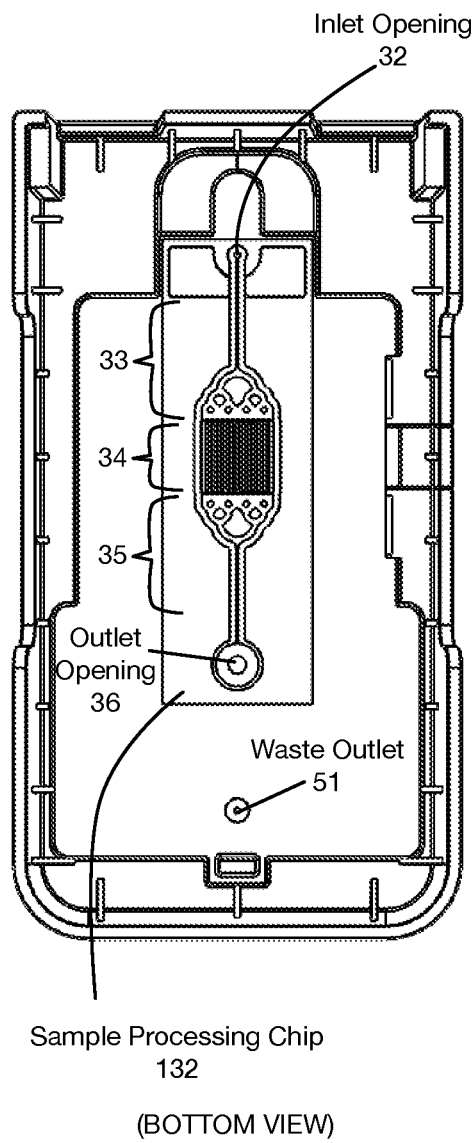

As shown in FIGS. 4A-4C, an example of the sample processing cartridge 130' can include a base substrate 131 to which other elements are coupled and/or in which other elements are defined. Furthermore, in relation to sample processing involving microfluidic elements, the base substrate 131 can function as a manifold for fluid transfer to microfluidic elements, accessing of sample processing volumes at various stages of processing, and transfer of waste materials produced during sample processing. In variations, the base substrate 131 supports one or more of: a sample processing chip 132, an inlet reservoir 133 for receiving sample material (e.g., containing cells, containing particles, etc.) and delivering it into the sample processing chip 132, an access region 134 for accessing one or more regions of the sample processing chip 132, a lid 135 covering the access region and including a gasket 136 providing sealing functions, and a waste containment region 137 for receiving waste material from the sample processing chip 132. The cartridge may have additional gasketed ports to also connect with off-cartridge pumping system present in the instrument. Variations of the base substrate 131 can, however, include other elements. For instance, as described in more detail below, the base substrate can include one or more openings, recesses, and/or protrusions that provide further coupling with the sample processing chip 132, in order to collectively define valve regions for opening and closing flow through the sample processing chip 132.

As shown in FIGS. 4A and 4C (bottom view), the sample processing chip 132, (equivalently referred to herein as a microwell device or a slide) defines a set of wells (e.g. microwells). Each of the set of wells can be configured to capture a single cell and/or one or more particles (e.g., probes, beads, etc.), any suitable reagents, multiple cells, or any other materials. In variations, microwells of the sample processing chip 132 can be configured for co-capture of a single cell with a single functional particle, in order to enable analyses of single cells and/or materials from single cells without contamination across wells. Embodiments, variations, and examples of the sample processing chip 132 are described in one or more of: U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; U.S. application Ser. No. 15/815,532, filed 16 Nov. 2017; U.S. application Ser. No. 16/115,370, filed 28 Aug. 2018, U.S. application Ser. No. 16/564,375, filed 9 Sep. 2019, and U.S. application Ser. No. 16/816,817, filed 12 Mar. 2020, which are each incorporated in their entirety by reference above.

In material composition, the sample processing chip 132 can be composed of microfabricated silicon or glass-fused silica materials, which function to enable higher resolution of the set of wells, enabled, for instance, by defining sharper edges (e.g., thinner well walls, well walls arranged at an angle approaching 90 degrees, etc.) in the set of wells. Materials and fabrication processes described can further enable one or more smaller characteristic dimensions (e.g., length, width, overall footprint, etc.) of the microwell cartridge as compared to conventional chip designs. Additionally or alternatively, the substrate include any other suitable material, such as—but not limited to—a polymer, metal, biological material, or any other material or combination of materials. Sample processing chip 132 may be fabricated by various processes such as precision injection molding, precision embossing, microlithographic etching, LIGA based etching, or by other suitable techniques.

In some variations, one or more surfaces of the set of wells (e.g., bottom surface, side surface, bottom and side surfaces, all surfaces, etc.) can be reacted with oligonucleotide molecules for capture of biomarkers from individual cells into individual microwells. The oligonucleotide molecules present on each and individual microwells may be barcoded to allow biomarkers processed in each microwell to be linked back to a particular well and hence a particular single cell. In one variation, the set of wells includes a set of microwells having hexagonal cross sections taken transverse to longitudinal axes of the wells, as described in one or more of the applications incorporated by reference above.

In one variation, as shown in FIG. 4C, the sample processing chip 132 can include an inlet opening 32, a first fluid distribution network 33 downstream of the inlet opening, for distribution of fluids to a set of microwells 34, a second fluid distribution network 35 downstream of the set of microwells 34, and an outlet opening 36 coupled to a terminal portion of the second fluid distribution network 35, for transfer of waste fluids from the sample processing chip 132. In this variation, the sample processing chip 132 is coupled to a first side (e.g., under-side) of the base substrate 131 (e.g., by laser welding, glue bonding, solvent bonding, ultrasonic welding or another technique). Coupling of the sample processing chip 132 to the side of the base substrate 131 can enable transfer of heat from the heating and cooling subsystem 150 to the set of microwells 34 and/or other regions of the sample processing chip 132, where the heating and cooling subsystem 150 is described in more detail below.

The base substrate 131, as described above, can also include an inlet reservoir 133 (e.g., defined at a second side of the base substrate 131 opposing the first side to which the sample processing chip 132 is coupled). The inlet reservoir functions to receive sample material (e.g., samples containing cells, sample containing barcoded cells, sample containing encapsulated materials, samples containing particles, etc.) and/or sample processing materials from the reagent cartridge 120 described above, for delivery into the inlet opening 32 of the sample processing chip 132. In variations, the inlet reservoir 133 can be defined as a recessed region within a surface of the base substrate 131, wherein the recessed region includes an aperture that aligns with and/or seals with the inlet opening 32 of the sample processing chip 132. The inlet reservoir 133 of the base substrate 131 can interface with upstream fluid containing components and/or bubble mitigating components, as described in one or more of: U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; U.S. application Ser. No. 15/815,532, filed 16 Nov. 2017; U.S. application Ser. No. 16/115,370, filed 28 Aug. 2018, U.S. application Ser. No. 16/564,375, filed 9 Sep. 2019, and U.S. application Ser. No. 16/816,817, filed 12 Mar. 2020, which are each incorporated in their entirety by reference above.

The inlet reservoir 133 can also be configured to interface with a fluid level detection subsystem 159 supported by or otherwise interfacing with the deck 110, as described in more detail below. In particular, portions of the inlet reservoir 133 can be composed of materials that enable sensing of fluid levels within the inlet reservoir 133 (e.g., by optical interrogation, by pressure sensing, by weight sensing, etc.). For instance, the inlet reservoir 133 can be composed of an optically transparent or translucent material to visible spectrum electromagnetic radiation and/or non-visible spectrum electromagnetic radiation (e.g., by fabrication with different materials, by fabrication to produce thin regions of material at the inlet reservoir 133, etc.), where sensing elements of the fluid level detection subsystem 159 can be configured to interrogate a level of fluid within the inlet reservoir 133 accordingly.

In variations, one or more of the inlet reservoir 133 of the base substrate 131 and the inlet 32 of the sample processing chip 132 can include valve components that can be open or closed by one or more components of the system 100. In a first variation, the inlet reservoir 132 includes an aperture that can be accessed by a pipette tip or any other suitable attachment of a fluid handling subsystem coupled to the gantry 170 (described in more detail below). In some embodiments, the aperture can be closed and therefore prevent fluid from traveling from the inlet reservoir 132 to the sample processing chip 132. The inlet reservoir 132 can, however, be configured in another suitable manner. The opening associated with the inlet reservoir 133 may have a conical shape surface open towards the top allowing interfacing and sealing a pipette tip such that fluid (aqueous solutions or oil or air) may be pumped directly into the microchannel defined in 33 in FIG. 4C.

As shown in FIGS. 4A and 4B, the base substrate 131 can also define an access region 134 for accessing one or more regions of the sample processing chip 132, where the access region can allow regions of the sample processing chip 132 to be observed and/or extracted from the sample processing chip 132 at various phases of sample processing. As shown in FIGS. 4A and 4B, the access region 134 can be defined as a recessed region within the base substrate 131, and include an opening 37 aligned with the region of the sample processing chip 132 that includes the set of microwells. The sample processing chip 132 may have as few as 100 microwells to as many as 100 million microwells. As such, in variations wherein the microwell region is open to the environment (e.g., without a covering to seal the wells), the opening 37 of the access region 134 can function as a microwell to provide access to contents of the microwells for observation and/or material extraction (e.g., by magnetic separation, as described in further detail below). The opening 37 can match a morphology and footprint of the microwell region, and in a first variation, as shown in FIG. 4B, can be a square opening. However, in other variations, the opening 37 can have another suitable morphology.

As shown in FIGS. 4A-4C, the base substrate 131 can include or otherwise couple to a lid 135 covering the access region 134, where the lid 135 can include a gasket 136 providing sealing functions, and where the lid 135 functions to transition the access region 134 between open and closed modes, thereby preventing evaporative sample loss and/or contamination of contents of the sample processing chip 132 during operation. The lid 135 can additionally or alternatively function to protect the contents of the microwells or other processing regions of the sample processing chip 132 from debris, enable a processing of the contents of the sample processing chip 132 (e.g. by isolating regions from the ambient environment), initiate the start of a protocol (e.g., by opening to accept reagents from a pipettor), prevent user manipulation of the sample processing chip 132 (e.g., by closing after all necessary reagents have been added), define (e.g., with the lid 135) part or all of a fluid pathway, cavity, or reservoir (e.g. serve as the top surface of a fluidic pathway between the inlet and the set of microwells, serve as a boundary of a fluid pathway adjacent the microwell region, serve as the top surface of a fluidic pathway between the set of wells and the waste chamber, etc.), or perform any other suitable function.

As shown in FIG. 4B, in at least one variation, the lid 135 can be complementary in morphology to features of the access region 134, such that the lid 135 mates with the access region 134, while providing a gap with the sample processing chip 132. Additionally, in variations (shown in FIGS. 4B and 4C), the lid 135 can be substantially flush with the base substrate 131 at a top surface when the lid 135 is in the closed position. However, the lid 135 can be morphologically configured in another suitable manner.

In variations, a protrusion 38 of the lid 135 can interface with the opening 37 of the access region 134, thereby substantially preventing access to the opening 37 when the lid is in the closed position. As shown in FIG. 4B, in some variations, the protrusion 38 can have a base (or other region) surrounded by a gasket 136, which functions to seal the opening 37 of the access region 134 in the closed position of the lid 135. Variations of the lid 135 can, however, omit a gasket and promote sealing of the access region 134 in another suitable manner.

Figure 5A:
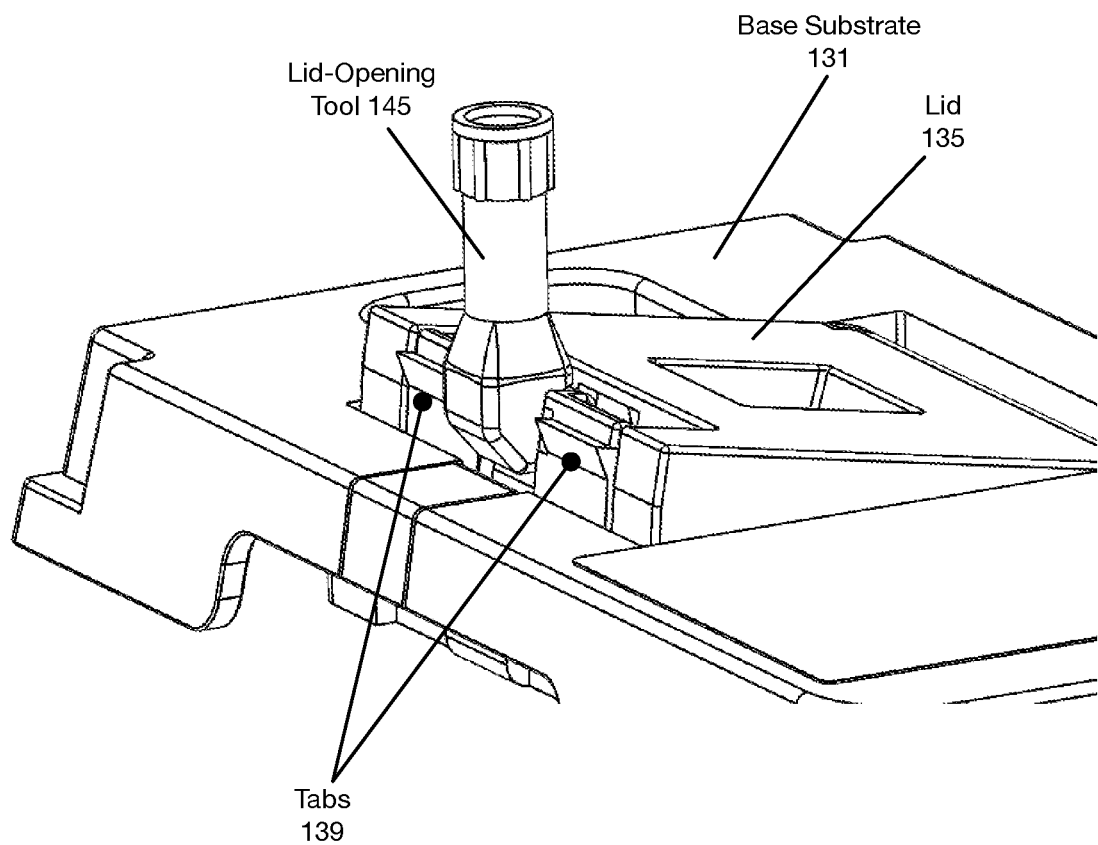
FIGS. 5A-5C depict operation modes of a lid-opening tool associated with the sample processing cartridge shown in FIGS. 4A-4C.
Figure 5B:
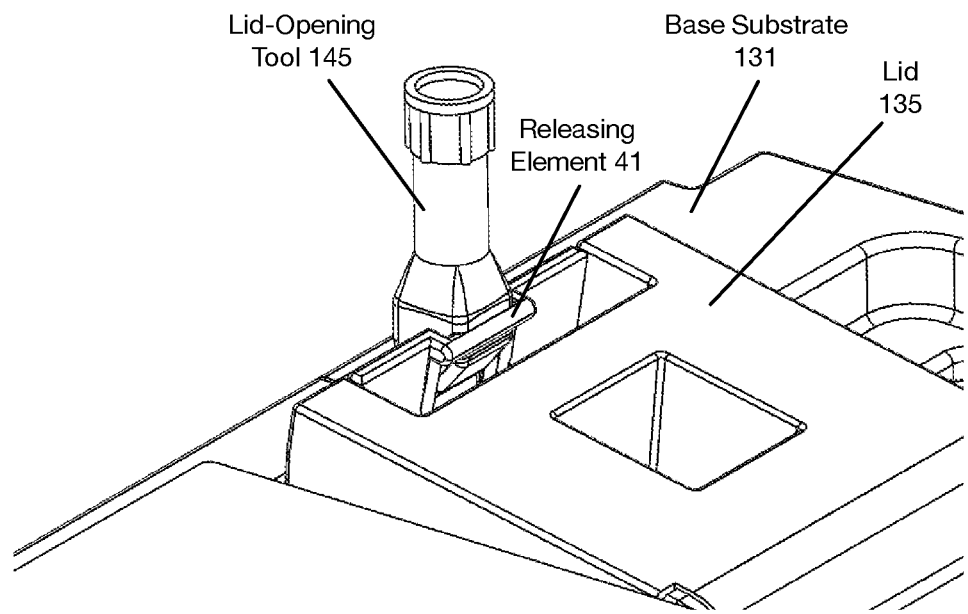
Figure 5C:
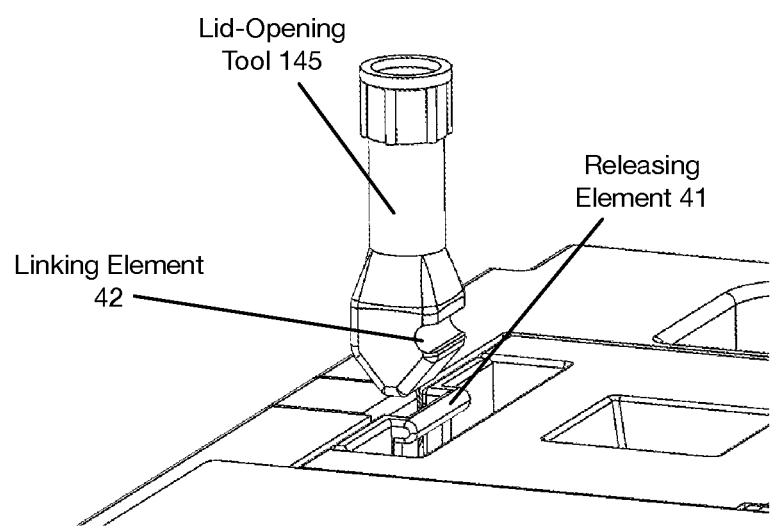

In some variations, the lid 135 can include a locking or latching mechanism that allows the lid 135 to be maintained in the closed position with the base substrate 131 until the locking/latching mechanism is released. In the variation shown in FIGS. 5A-5C, a peripheral portion of the lid 135 can include a one or more tabs 39 that interface with corresponding tab receiving portions of the base substrate 131, where the tabs 39 are configured to flex when pushed into the base substrate 131 until they interface with the tab receiving portions of the base substrate 131 and return from a flexed configuration to a latched state. Additionally or alternatively, in the variation shown in FIGS. 5A-5C, the locking/latching mechanism can include a releasing body 41 (e.g., bar, recess, hook, etc.) that can be interfaced with in order to release the tab(s) 39 from the tab receiving portions, and transition the lid 135 from the closed mode to the open mode in relation to the base substrate 131. As such, the lid 135 provides the lid an open mode in which the access region 134 is uncovered and a closed mode in which the access region 134 is covered. In the variation shown in FIGS. 5A-5C, the releasing element 41 includes a bar that is recessed away from the access region 134 of the base substrate 131, where the bar can be reversibly coupled to a lid-opening tool 145. In variations, the lid-opening tool 145 can include a first region (e.g., first end) that interfaces with a an actuator (e.g., actuating tip, pipettor of a fluid handling subsystem coupled to the gantry 170 described below, etc.), and a second region (e.g., second end) including a linking element 42 configured to interface with the releasing element 41 of the lid 135. Then, with movement of the pipettor/pipette interface, the lid-opening tool 145 can be configured to pull on the releasing element 41 and/or push on the lid 135 in order to transition the lid between open and/or closed modes. As such, in relation to fluid handling elements coupled to the gantry 170 described below, the system Dm can provide operation modes for: coupling a lid-opening tool 145 to an actuator (e.g., coupled to a gantry 170), the lid-opening tool including a linking element 42; moving the lid-opening tool into alignment with a releasing element 41 of the lid 135, reversibly coupling the linking element 42 with the releasing element 41; and applying a force to the releasing element 41, thereby releasing the lid 135 from a latched state and transitioning the lid 135 from a closed mode to an open mode. In order to effectively apply an unlatching force (e.g., by the actuator (e.g., coupled to a gantry 170), the base substrate 131 can be retained in position (e.g., by retention elements described in Section 2.1.4, by retention elements of the heating and cooling subsystems, by retention elements of the fluid level detection subsystem, by retention elements of the deck, etc.) which passively or actively apply counteracting forces against the unlatching forces applied through the lid-opening tool 145.

In variations, however, the locking/latching mechanism can additionally or alternatively include or operate by way of: a lock-and-key mechanism, magnetic elements, or another suitable mechanism. Furthermore, in alternative variations, the lid 135 can include another lid actuator, for instance, including a motor that rotates the lid about an access parallel to a broad surface of the sample processing cartridge 130. The actuator can additionally or alternatively be configured to translate the lid 135 (e.g. slide the lid 135 parallel to a broad surface of the sample processing cartridge 130, translate the lid 135 perpendicular to the broad surface, etc.) or otherwise move the lid 135 to selectively cover and uncover one or more predetermined regions (e.g. the set of microwells). As such, the lid 135 can be configured to operate in an automated or semi-automated fashion, such that the lid 135 automatically closes upon one or more triggers (e.g., cell capture protocol is initiated by a user, cell processing protocol is initiated by a user, all reagents for a selected protocol have been added from the reagent cartridge 120, etc.) and opens upon one or more triggers (e.g., cell capture protocol has been completed, upon user request, it has been determined that the cells are viable, it has been determined that single cells have been captured, etc.). Additionally or alternatively, operation of the lid 135 can be initiated and/or completed by a user, operated according to a schedule or other temporal pattern, or otherwise operated.

As shown in FIGS. 4A-4C, the base substrate 131 can also include a waste containment region 137 for receiving waste material from the sample processing chip 132. The waste containment region 137 can also function to maintain desired pressures (e.g., vacuum pressures, etc.) within the sample processing chip 132, thereby enabling flow of liquid from the inlet reservoir 133 through the sample processing chip 132 and to the waste containment region 137. The waste containment region 137 can be defined as a volume (e.g., recessed into the base substrate 131, extending from the base substrate 132, coupled to an outlet of the base substrate 131, etc.) for receiving waste or other materials from the sample processing chip 132. In the variation shown in FIGS. 4A-4C, the waste containment region 137 is defined at a side of the base substrate 131 opposing the side to which the sample processing chip 132 is coupled, such that waste from the sample processing chip 132 is pushed or pulled upward into the waste containment region 137 by forces of the pumping subsystem 157 described in more detail below. However, the waste containment region 137 can additionally or alternatively be configured in another suitable position relative to the base substrate 131 and the sample processing chip 132, in order to receive waste.

The waste containment region 137 can have a volumetric capacity of 10-100 mL or another suitable volumetric capacity.

As shown in FIGS. 4A-4C, the waste containment region 137 can include a cover 48 (e.g., a cover that is approximately co-planar with the lid 135), which facilitates containment of waste within the waste containment region 137. Alternatively, the waste containment region 137 may not include a cover. Furthermore, as shown in FIG. 4C, examples of the waste containment region 137 can include a pump outlet 51 distinct from the cover, where the pump outlet 51 can allow the residual air in the waste chamber to be pressurized by an off-cartridge pump(e.g., by pumping mechanisms, etc.); however, variations of the waste containment region 137 can alternatively omit a waste outlet.

In relation to the waste containment region 137, the system 100 can further include a valve 43 configured to allow and/or prevent flow from the sample processing chip 132 to the waste containment region 137. The valve 43 can interface with the outlet opening 36 of the sample processing chip 132 described above, in order to enable and/or block flow out of the outlet opening 36 and into the waste containment region 137. The valve 43 can have a normally open state and transition to a closed state upon interacting with a valve-actuating mechanism. Alternatively, the valve 43 can have a normally closed state and transition to an open state upon interacting with a valve-actuating mechanism.

Figure 6A:
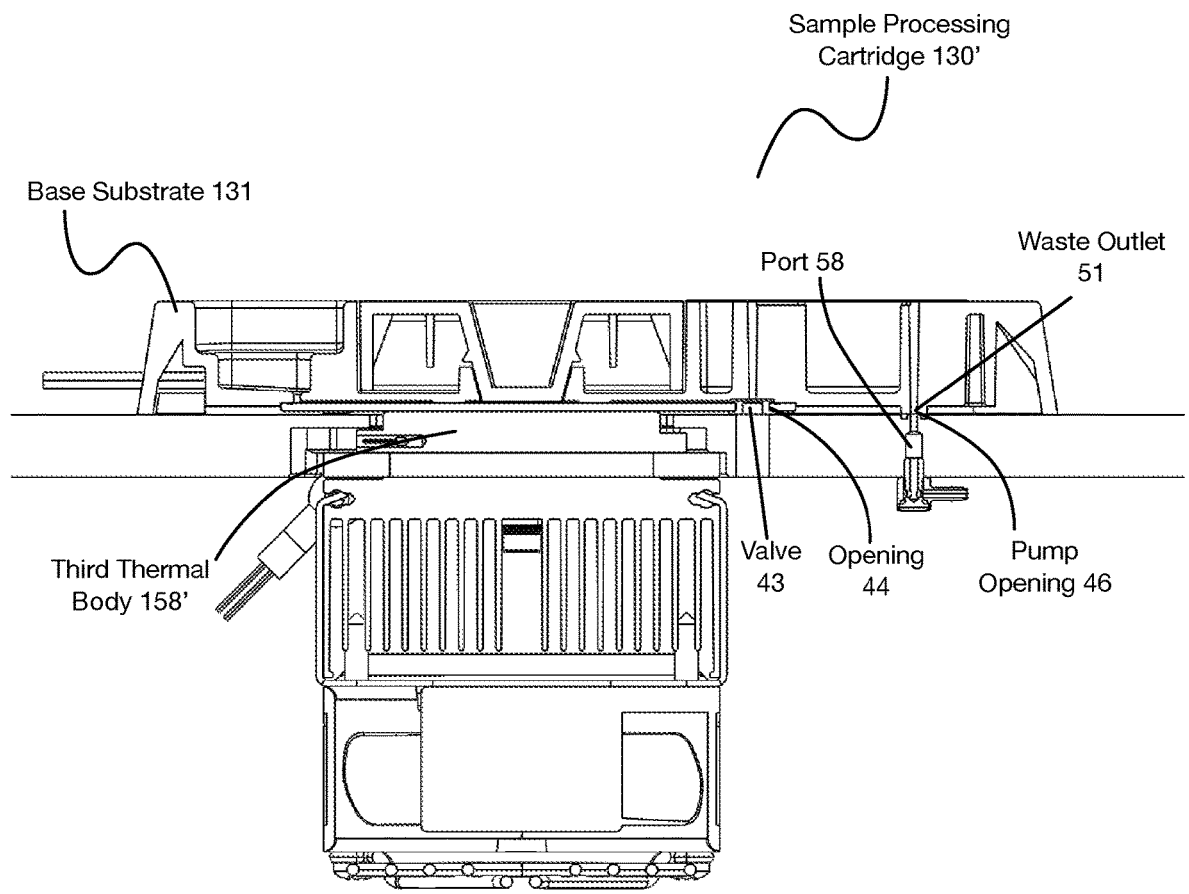
FIGS. 6A-6B depict operation modes of a valve and heating subsystem associated with the sample processing cartridge shown in FIGS. 4A-4C.
Figure 6B:
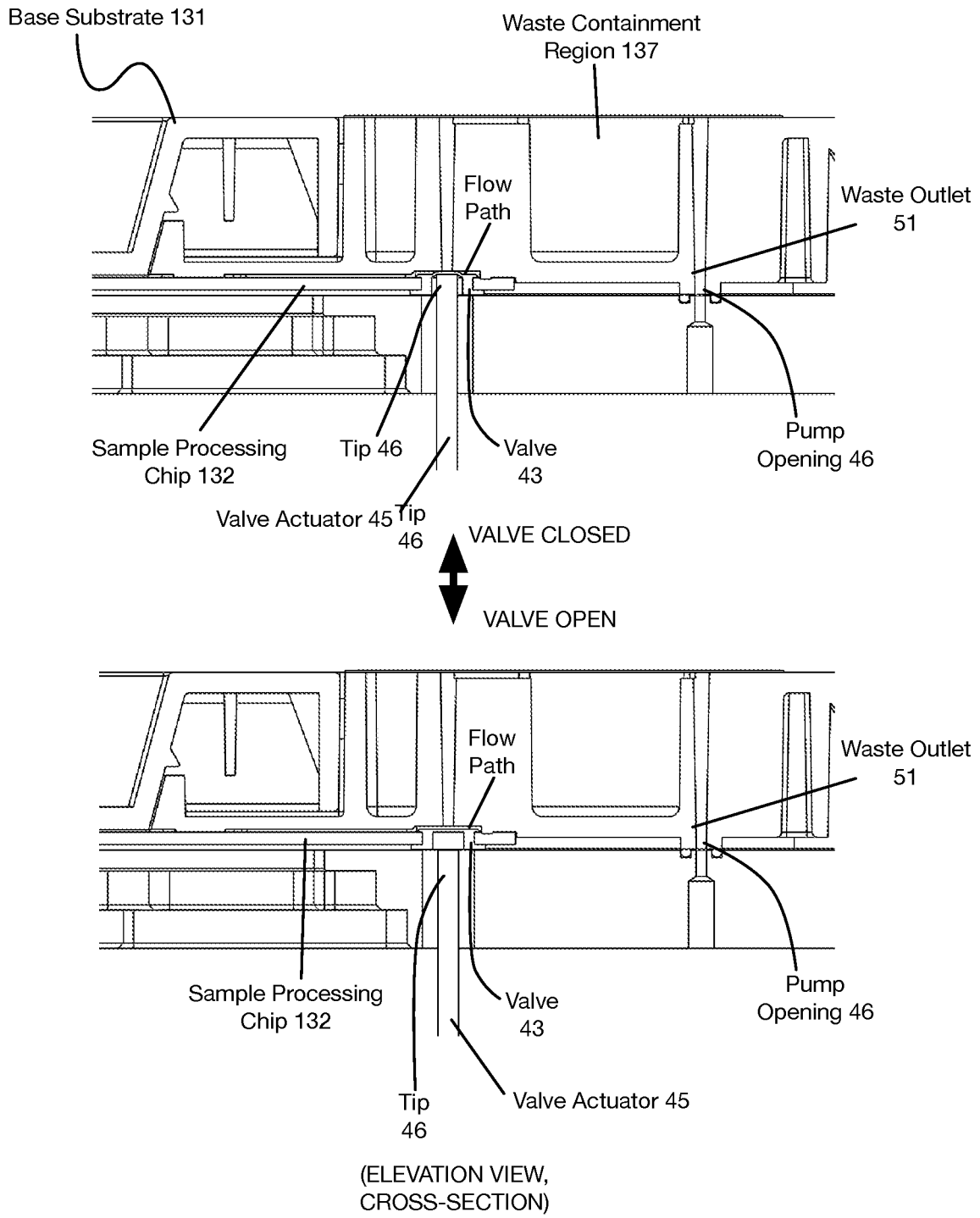

In the variation shown in FIGS. 4A and 6A-6B, the valve 43 comprises an elastomeric body and is configured to couple the sample processing chip 132 to the base substrate 131 through an opening 44 of the sample processing chip 132 that aligns with a corresponding valve-receiving portion of the base substrate 131. In this variation, a transitionable portion of the valve 43 is configured to be positioned along a flow path from the outlet opening 36 of the sample processing chip 132 to the inlet of the waste containment region 137 of the base substrate 132 (e.g., along a flow path from the microwell region to an outlet of the sample processing chip into a waste containment region of the sample processing cartridge). In an example the opening 44 of the sample processing chip 132 is contiguous with the outlet opening 37 of the sample processing chip 132; however, in other variations, the outlet opening 37 and the opening 44 may be displaced from the each other and connected by another microfluidic channel. As such, closure of the valve 43 can block flow from the outlet opening 37 into the waste containment region 137, and the valve 43 can be opened to allow flow from the outlet opening 37 into the waste containment region 137.

In a variation shown in the cross sectional images of the base substrate 131 shown in FIG. 6B, a valve actuator 45 can access the base substrate 131 from below (e.g., from below the deck), and pass through a channel or other recess/opening of the base substrate 132 in order to interact with the valve 43. In particular, when a tip 46 (aligned with the opening into the base substrate) of the valve actuator 45 pushes against the valve (e.g., a elastomeric membrane of the valve 43), as shown in FIG. 6B (top), the valve 43 can transition to a closed state in order to fluidically decouple the outlet opening 37 of the sample processing chip 132 from the waste containment region 137. Additionally or alternatively, as shown in FIG. 6B (bottom), removal of force by the valve actuator 45 can remove pressure from the valve 43 and transition it to an open state to fluidically couple the outlet opening 36 of the sample processing chip 132 from the waste containment region 137. As such, the valve actuation subsystem includes an engaged mode wherein the tip extends into the valve opening to deform the elastomeric valve, thereby closing the flow path, and a disengaged mode wherein the tip is retracted, thereby opening the flow path. However, the valve 43 can additionally or alternatively be configured in another suitable manner.

In other variations, the system can include a similar mechanism for coupling a valve to other flow paths of the sample processing chip 132 and/or to the base substrate 131.

Variations of the base substrate 131 can, however, include other elements. For instance, as described in more detail below, the base substrate 131 can include one or more openings, recesses, and/or protrusions that provide further coupling with the sample processing chip 132, in order to promote or inhibit flow through the sample processing chip 132. For instance, as shown in FIG. 6A, the base substrate can include a pump opening 46 that couples the base substrate 131 to a pumping element of the pumping subsystem 157 (e.g., through deck 110), in order to drive and/or stop fluid flow through the sample processing chip 132.

The base substrate 131 of the sample processing cartridge 130 can, however, include other suitable elements.

2.1.3 Deck-Supported Element: Tool Container

As shown in FIGS. 2A and 2B, the deck 110 includes at least one region 113 for supporting a unit of the tool container 140, where the region 113 functions to position the tool container 140 relative to fluid handling apparatus of the gantry 170 described below. The region 113 can also position the tool container 140 in proximity to the reagent cartridge 120 and sample processing cartridge 130 being used, in order to provide a more compact system and improve efficiency of automated operations involving contents of one or more of the reagent cartridge 120, sample processing cartridge 130, and tool container 140. The region 113 can also include an opening that allows the tool container 140 to be at least partially recessed below a surface of the deck 110.

The tool container 140 functions to contain, in one or more compartments, one or more units of various tools for fluid aspiration, fluid delivery, separation of target material from non-target material of a sample, sample processing cartridge lid-opening tools 145, and/or other tools, according to one or more workflows for various applications. As such, the tool container 140 can facilitate transfer and/or mixing of reagents with sample, fluidically couple and/or decouple elements at various regions of the deck 110, or otherwise interact with one or more components of the system 100.

Figure 7A:
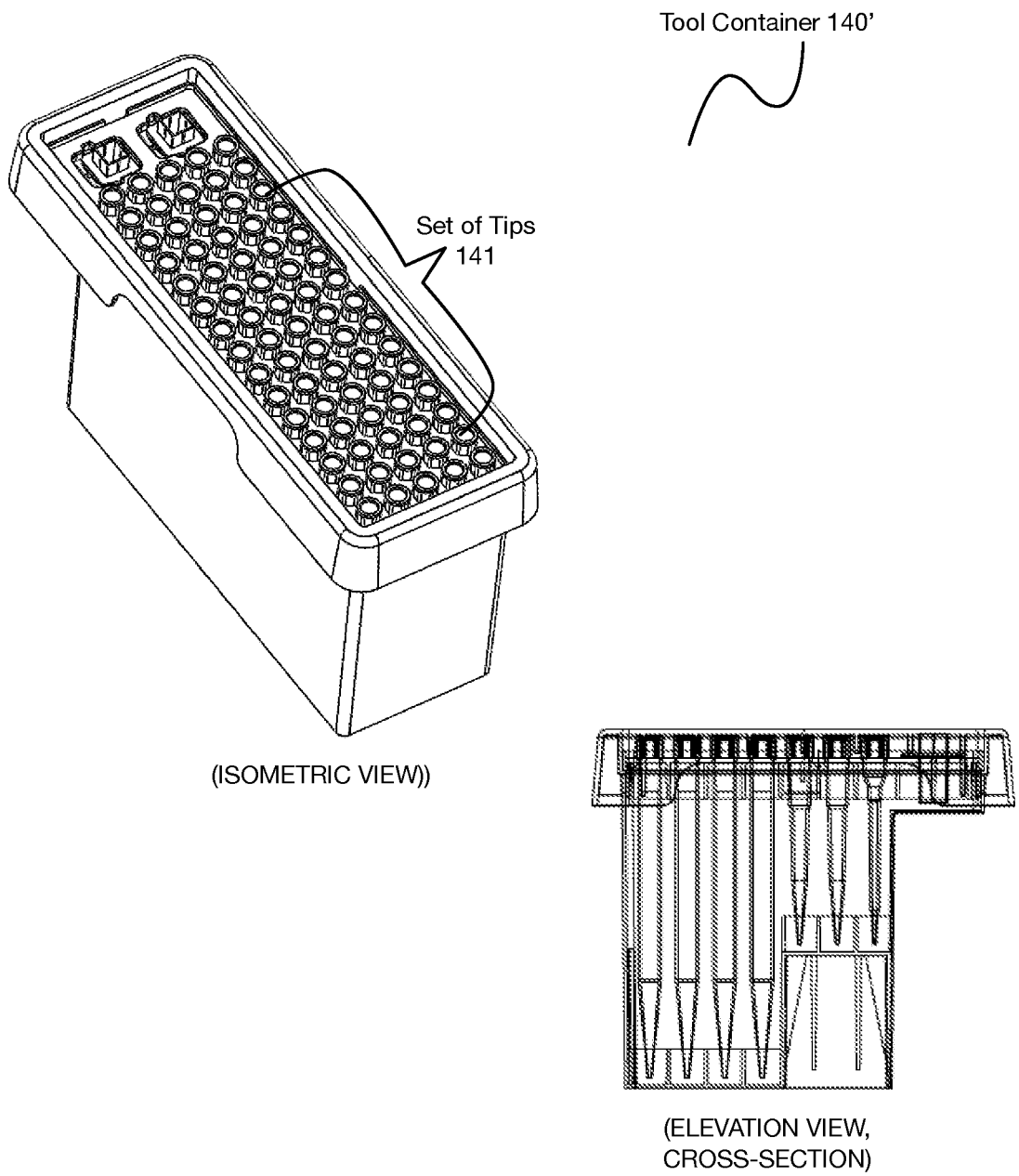
FIGS. 7A and 7B depict variations of a tool container and contents associated with a system for automated single cell sample processing.

In variations, one of which is shown in FIG. 7A the tool container 140' can include a set of tips 141 for fluid aspiration and/or fluid delivery (e.g., to and from the reagent cartridge 120, to and from the sample processing cartridge 130, etc.). The set of tips 141 can include any or all of: standard pipette tips (e.g. P20 tips, P200 tips, P1000 tips, etc.); additionally or alternatively, the set of tips can include piercing tools (e.g., to gain access to a reagent tube through a seal), blunt tips (e.g. for facilitating fluid flow, for blocking an aperture, for defining a fluidic pathway, etc.), or any other suitable tips. The tips can be configured or otherwise used in any or all of: piercing (e.g. piercing a reagent strip foil), transferring and/or mixing a set of reagents (e.g. a tip for mixing ethanol and priming buffer, a tip for transferring SPRI ethanol, a tip for transferring SPRI supernatant, a tip for transferring SPRI elution buffer, etc.), cell dispensing into a unit of the sample processing cartridge 130, dispensing of functionalized particles into a unit of the sample processing cartridge, facilitating the performance of a predetermined set of processes (e.g., particle washing, cell lysis, oil dispensing, pre-reverse-transcription wash, other workflows described below etc.), or can have any other suitable function.

As shown in FIG. 7A, the set of tips 141 can be arranged in an array (e.g., according to type, according to size, etc.) within the tool container 140, where the internal base of the tool container 140 can include drip-catching sections for catching drips leaving the aspiration/delivery ends of the tips from various fluid handling operations. Furthermore the tool container 140 can include spacing elements for preventing individual tips of the set of tips 141 from contacting each other, thereby preventing cross-contamination. Furthermore, regions of one or more of the tips for interfacing with the pipettor can be conductive (e.g., thermally conductive, electrically conductive, composed of a metal, composed of a conductive polymer, composed of a semiconducting material, etc.).

Figure 7B:
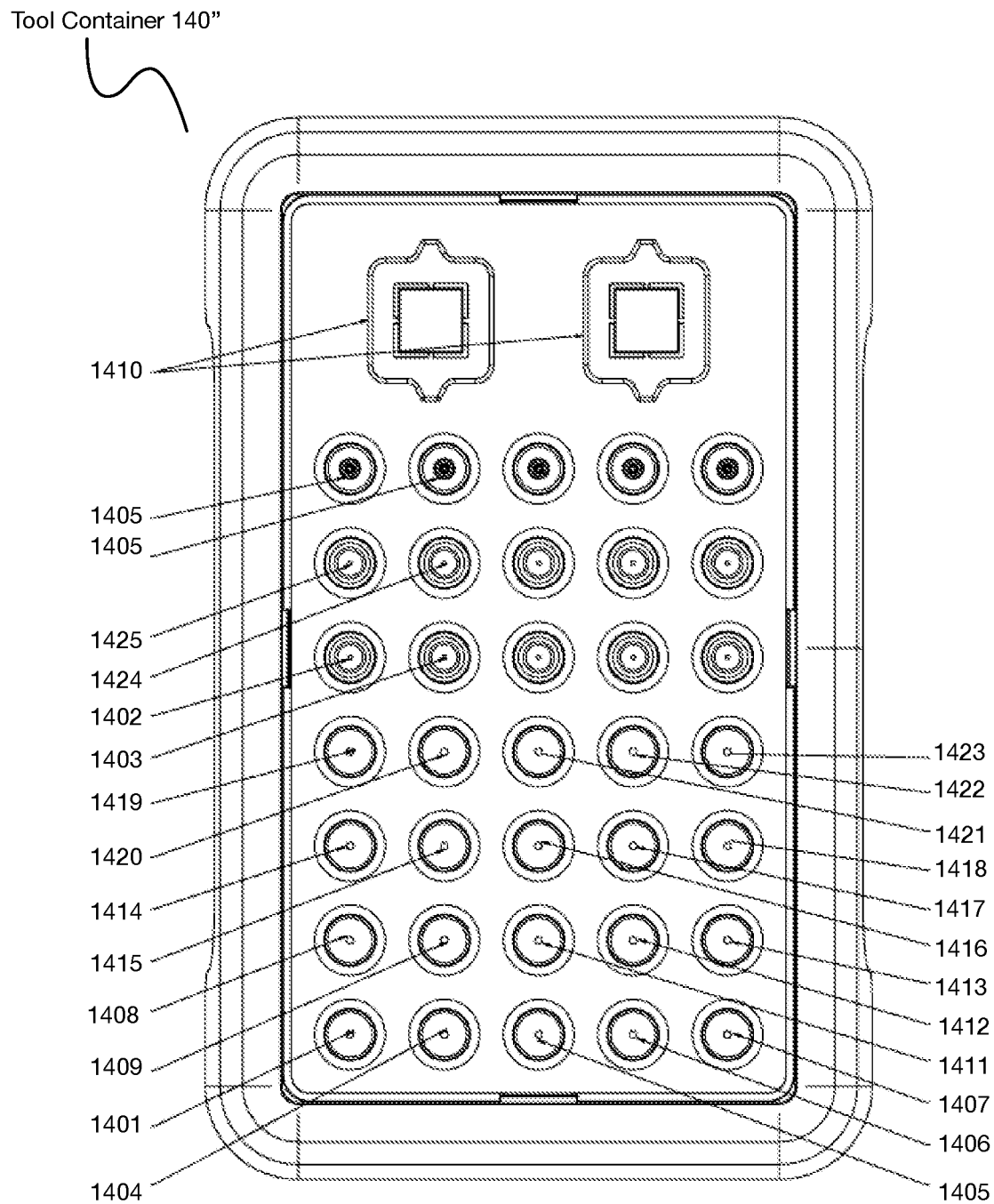

In a specific example for a 3' processing protocol shown in FIG. 7B, the tool container 140" can include: a first tip 1401 (e.g., with a tip volume of 200 mL, with a tip volume of 200 μL) for transferring ethanol, a wash buffer, and/or a priming solution; a second tip 1402 (e.g., with a tip volume of 1000 mL, with a tip volume of 1000 μL) for transferring of a cell suspension; a third tip 1403 (e.g., with a tip volume of 200 mL, with a tip volume of 200 μL) for transferring functionalized particles; a fourth tip 1404 (e.g., with a tip volume of 1000 mL, with a tip volume of 1000 μL) for transferring a wash buffer; a fifth tip 1405 (e.g., with a tip volume of 1000 mL, with a tip volume of 1000 μL) for transfer of a particle binding buffer; a sixth tip (e.g., with a tip volume of 1000 mL, with a tip volume of 1000 μL) for transfer of DTI and/or a lysis buffer; a seventh tip 1407 (e.g., with a tip volume of 1000 mL, with a tip volume of 1000 μL) for transfer of perfluorinert oil; an eighth tip 1408 (e.g., with a tip volume of 1000 mL, with a tip volume of 1000 μL) for transfer of DTT, particle binding solution, and/or wash solution; a ninth tip 1409 (e.g., with a tip volume of 1000 mL, with a tip volume of 1000 μL) for transfer of DTT and/or a pre-RT reaction wash solution; one or more magnetic sleeves 1410 for magnetic retrieval; an $11^{th}$ tip 1411 (e.g., with a tip volume of 1000 mL, with a tip volume of 1000 μL) for transfer of DTT and/or an RT cocktail solution; a $12^{th}$ tip 1412 (e.g., with a tip volume of 1000 mL, with a tip volume of 1000 μL) for transfer of an exonuclease treatment; a $13^{th}$ tip 1413 (e.g., with a tip volume of 1000 mL, with a tip volume of 1000 μL) for transfer of mineral oil; a $14^{th}$ tip 1414 for transfer of an exonuclease treatment; a $15^{th}$ tip 1415 (e.g., with a tip volume of 1000 mL, with a tip volume of 1000 μL) for transfer of a sodium hydroxide solution; a $16^{th}$ tip 1416 (e.g., with a tip volume of 1000 mL, with a tip volume of 1000 μL) for transfer of a second wash buffer; a $17^{th}$ tip 1417 for transfer of a second strand synthesis solution; an $18^{th}$ tip 1418 (e.g., with a tip volume of 1000 mL, with a tip volume of 1000 μL) for transfer of a particle solution; a $19^{th}$ tip 1419 (e.g., with a tip volume of 1000 mL, with a tip volume of 1000 μL)for transfer of a second wash buffer; a $20^{th}$ tip 1420 (e.g., with a tip volume of 1000 mL, with a tip volume of 1000 μL) for transfer of a PCR master mix and/or particle solution; a $21^{st}$ tip 1421 (e.g., with a tip volume of 1000 mL, with a tip volume of 1000 μL) for transfer of mineral oil; a $22^{nd}$ tip 1422 (e.g., with a tip volume of 1000 mL, with a tip volume of 1000 μL) for transfer of a PCR product; a $23^{rd}$ tip 1423 (e.g., with a tip volume of 1000 mL, with a tip volume of 1000 μL) for transfer of AMPure and/or supernatant; a $24^{th}$ tip 1424 (e.g., with a tip volume of 1000 mL, with a tip volume of 1000 μL) for transfer of ethanol; a $25^{th}$ tip 1425 (e.g., with a tip volume of 1000 mL, with a tip volume of 1000 μL) for transfer of ethanol; a $26^{th}$ tip 1426 (e.g., with a tip volume of 50 mL, with a tip volume of 50 μL) for transfer of ethanol; and a $27^{th}$ tip 1427 (e.g., with a tip volume of 50 mL, with a tip volume of 50 μL) for transfer of nuclease-free water and/or derived products.

In variations, the tool container 140 can additionally or alternatively include other sample processing tools. In one variation, the tool container 140 can include one or more units of a separation tool tip 142 for magnetic separation of target material from non-target material (described in more detail below). Additionally or alternatively, in variations, the tool container 140 can additionally or alternatively include units of a lid-opening tool 145 for transitioning the lid 135 described above to an open configuration. However, in relation to disposability of the tool container 140 and/or its contents, the tool container 140 can be configured to contain only disposable elements, and to omit reusable elements (e.g., units of a lid-opening tool 145, as shown in FIG. 2B).

Furthermore, units of contents of the tool container 140 can additionally be included with one or more of the reagent cartridge 120, the sample processing cartridge 130, otherwise arranged at the deck 110, separate from the deck 110, separate from the system 100 or otherwise arranged. In other variations, re-useable tools used in the tool container 140 may include other tools that use electrical, electromagnetic, optical or combination of different modalities to interact with the gantry 170 and be moved to specific locations over the reagent cartridge 120 and/or the sample processing cartridge 130 to provide specific energies (e.g., heat, optical signals, electromagnetic waves, etc.) and/or sense specific signals (e.g., optical, thermal, electromagnetic, etc). These tools may be wired to the control electronics or may be wirelessly charged and controlled/communicated.

2.1.4 Deck-Supported Elements—Registration and Retention Features

As shown in FIGS. 8A through 8I, the deck no can include a set of retention elements positioned relative to region in for the reagent cartridge 120, region 112 for the sample processing cartridge 130, and region 113 for the tool container 140, where the set of retention elements function to register and retain the reagent cartridge 120, sample processing cartridge 130, and tool container 140 at the deck 110 during operation to process samples, and to enable release of the reagent cartridge 120, sample processing cartridge 130, and tool container 140 from the deck 110 when appropriate. The set of retention elements can include mechanical retention elements (e.g., recesses, protrusions, etc.) configured provide retention by way of a snap fit, a press fit, ratcheting, or another suitable mechanism. Additionally or alternatively, the set of retention elements can include magnetic retention elements or other suitable retention elements. In variations including magnetic retention elements, associated magnets can be positioned away from magnetic separation areas of the reagent cartridge 120 and deck 110 (described in relation to 2.1.8 below) so as to not interfere with associated magnetic separation mechanisms. Alternatively, the associated magnets can be positioned in proximity to the magnetic separation areas of the reagent cartridge 120 and deck 110, in order to facilitate magnetic separation operations performed at the reagent cartridge 120 (and/or other suitable portions of the system.

The retention elements can provide uniform mechanisms for each of the reagent cartridge 120, sample processing cartridge 130, and tool container 140. Alternatively, the reagent cartridge 120, sample processing cartridge 130, and tool container 140 can each include different retention elements that operate by different mechanisms as appropriate. The retention mechanisms supported by the set of retention elements can be manually operated (e.g., a user interacts with the retention elements to disengage and/or engage a component with the deck no). Additionally or alternatively, the retention mechanisms supported by the set of retention elements can be non-manually operated (e.g., with actuators coupled to the retention elements in order to transition them between engaged and disengaged modes). Retention mechanisms are configured to operate with appropriate morphologies (e.g., to facilitate engagement by a manual operator or apparatus), loading and unloading forces, and/or transmitted forces (e.g., to other sensitive elements of the deck 110).

Figure 8A:
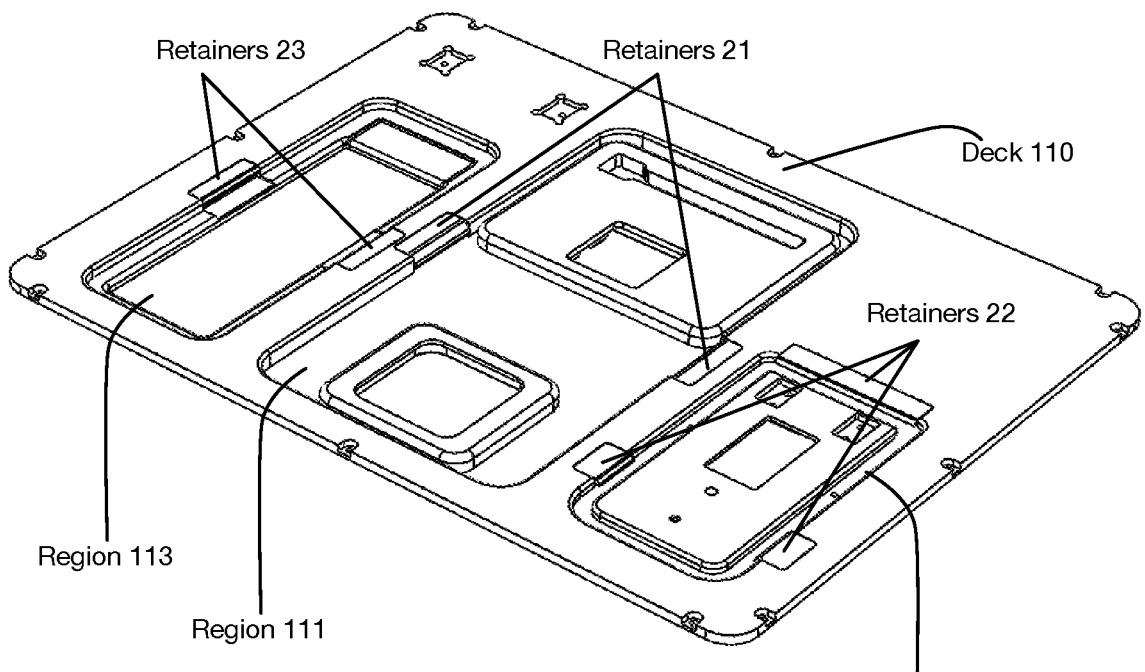
FIGS. 8A-8I depict variations of features for retaining elements at a deck of a system for automated single cell sample processing.

In the variation shown in FIG. 8A, the deck 110 can include a first subset of retention elements 21 corresponding to region in for the reagent cartridge 120, a second subset of retention elements 22 corresponding to region 112 for the sample processing cartridge 130, and a third subset of retention elements 23 corresponding to region 113 for the tool container 140.

Figure 8B:
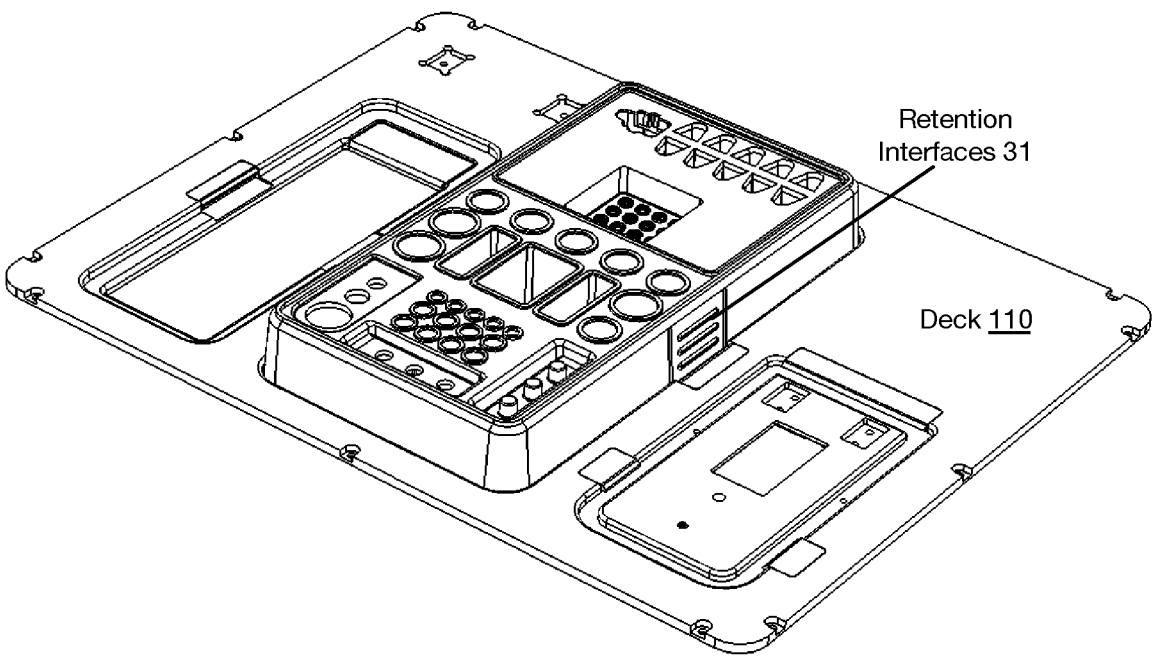
Figure 8C:
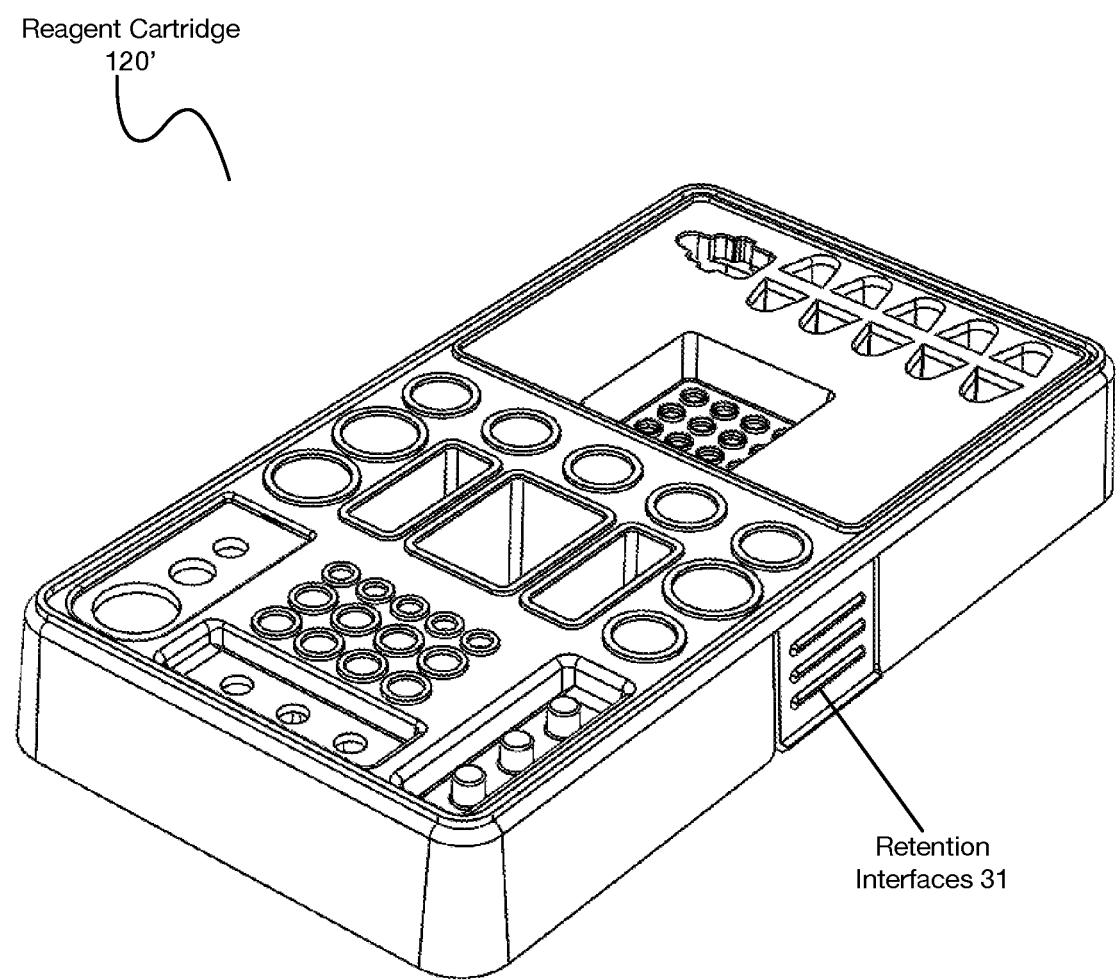
Figure 8D:
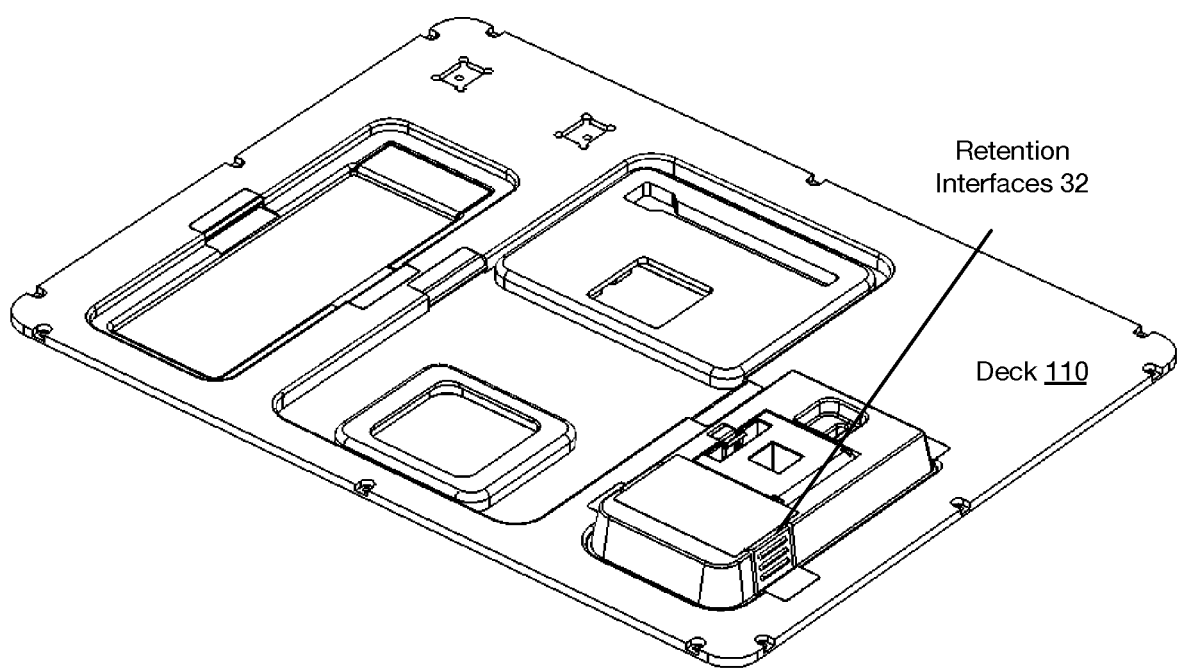
Figure 8E:
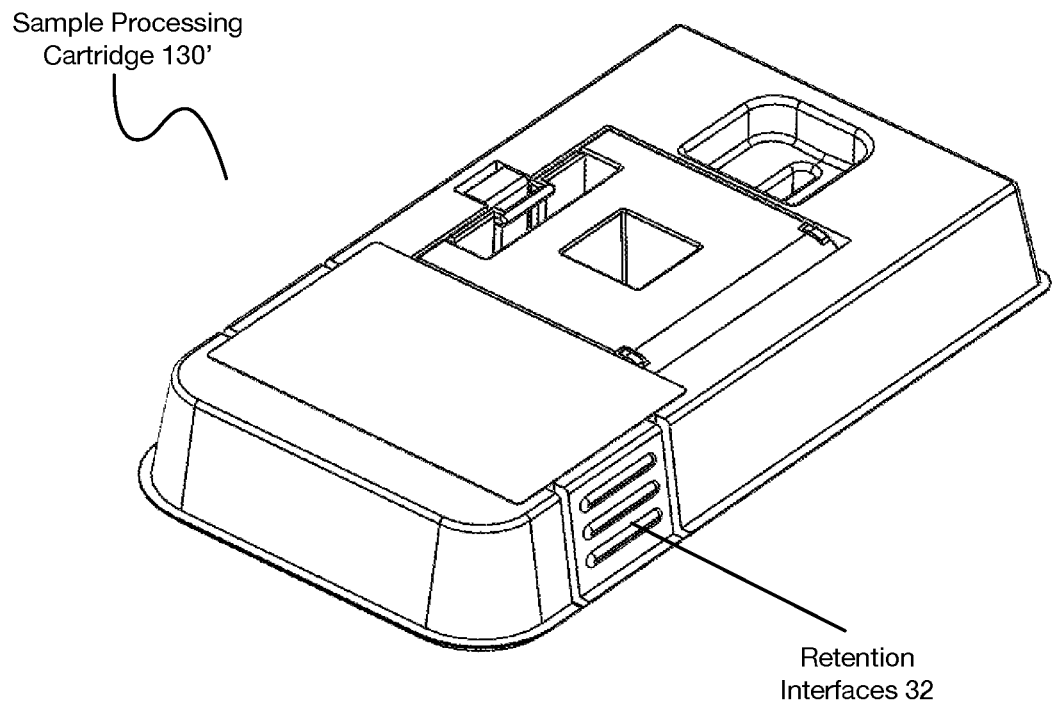
Figure 8F:
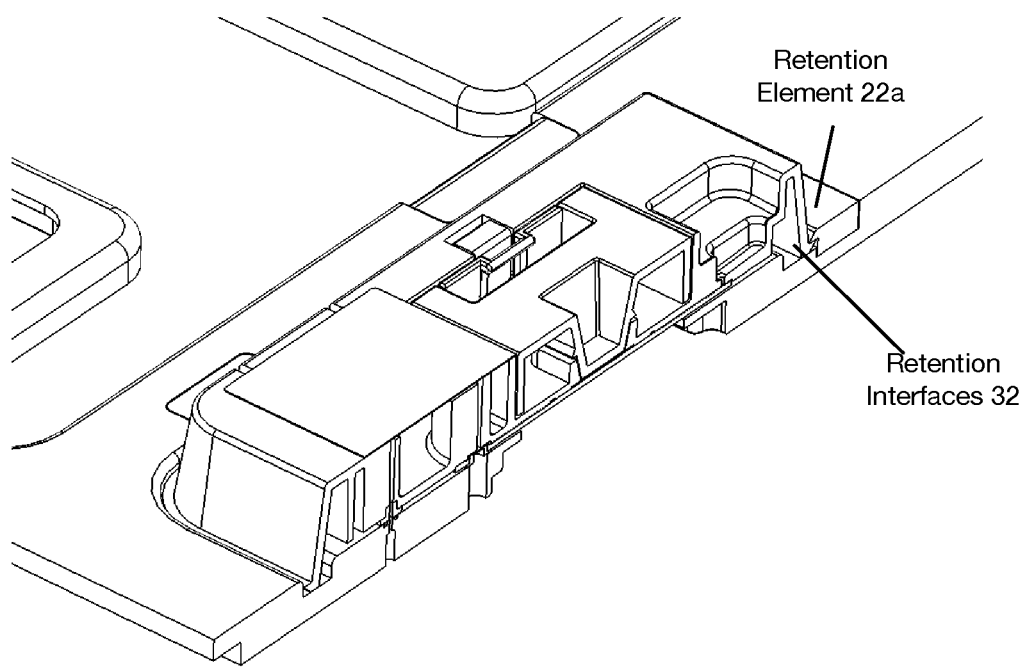
Figure 8G:
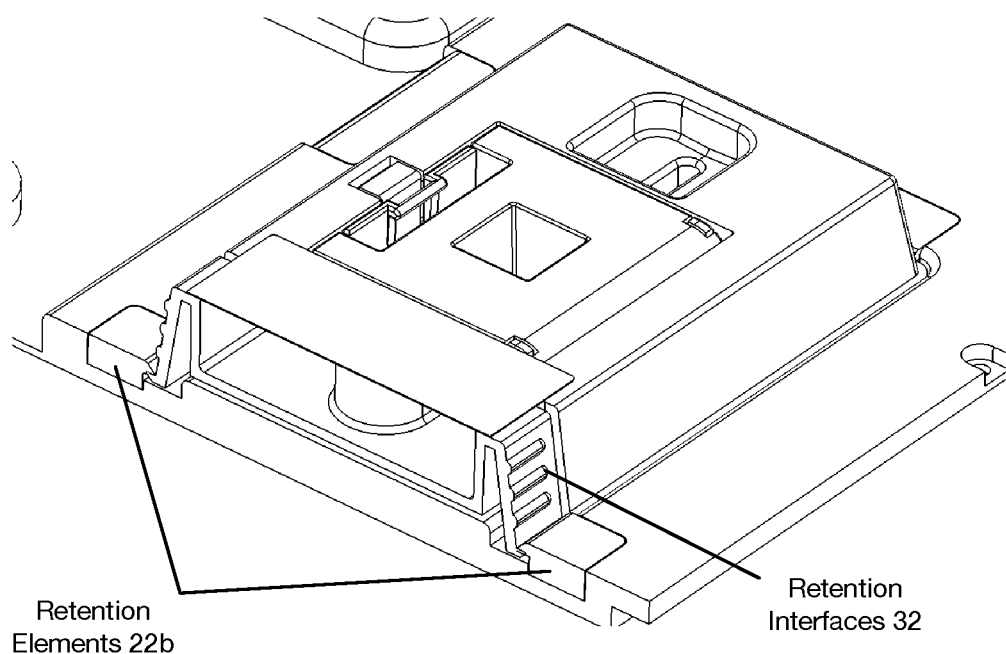

In relation to FIG. 8A, the first subset of retention elements 21 at region 111 can include a set of snap ledges positioned about region 111 (e.g., at contralateral sides of region in), in a manner that complements corresponding retention interfaces 31 of the reagent cartridge 120. In more detail, as shown in FIGS. 8B and 8C, the retention interfaces 31 of the reagent cartridge 120' can include a set of tabs (e.g., flexible tabs) that can be compressed from a baseline position to be positioned at region in, where release from the compressed configuration allows the set of tabs to latch with the snap ledges. The set of tabs of the retention interfaces 31 can further include gripping features (e.g., bumps, etc.) that allow a user to compress the set of tabs easily. In related variations, the first subset of retention elements 21 and corresponding retention interfaces of the reagent cartridge 120' can be positioned in another manner. For instance, the set of tabs of the reagent cartridge can be positioned at a non-peripheral region of the reagent cartridge 120 (e.g., with finger and/or thumb hole cutouts), with corresponding alignment with the retention elements 21 of the deck 110. In relation to providing robust contact, the retention elements 21 can be configured to provide a biasing force against deck elements (e.g., heating and cooling subsystem elements, magnetic separation subsystem elements, etc.) that the reagent cartridge 120 interacts with, in order to provide robust contact between surfaces. The biasing force used against the deck elements may be at least 0.5 lbs or at least 1 lbs or at least 2 lbs, or at least 3 lbs.

In relation to FIG. 8A, the second subset of retention elements 22 at region 112 can include a set of snap ledges positioned about region 112 (e.g., at contralateral sides of region 112 and at a third peripheral side of region 112), in a manner that complements corresponding retention interfaces 32 of the sample processing cartridge 130. In more detail, as shown in FIGS. 8D through 8G, the retention interfaces 32 of the sample processing cartridge 130 can include a set of tabs (e.g., flexible tabs) that can be compressed from a baseline position to be positioned at region 112, where release from the compressed configuration allows the set of tabs to latch with the snap ledges. In this variation, the sample processing cartridge 130 can be configured to be inserted into/engaged with a first of the retention elements 22a (e.g., at a side of the sample processing cartridge near the inlet reservoir, at a side of the sample processing cartridge near the waste containment, region, etc.) prior to latching of the other retention interfaces 22b with the contralateral snap ledges. Similar to the set of tabs of the reagent cartridge 120, the set of tabs of the retention interfaces 32 of the sample processing cartridge 130 can further include gripping features (e.g., bumps, etc.) that allow a user to compress the set of tabs easily. In relation to providing robust contact, the retention elements 22 can be configured to provide a biasing force against deck elements (e.g., heating and cooling subsystem elements, pumping subsystem elements, etc.) that the sample processing cartridge 130 interacts with, in order to provide robust contact between surfaces. Furthermore, the set of retention elements 22 of the deck no can be configured to reversibly engage the sample processing cartridge 120 and provide a counteracting force against the lid-opening tool 145 described in relation to lid-opening operation modes.

Figure 8H:
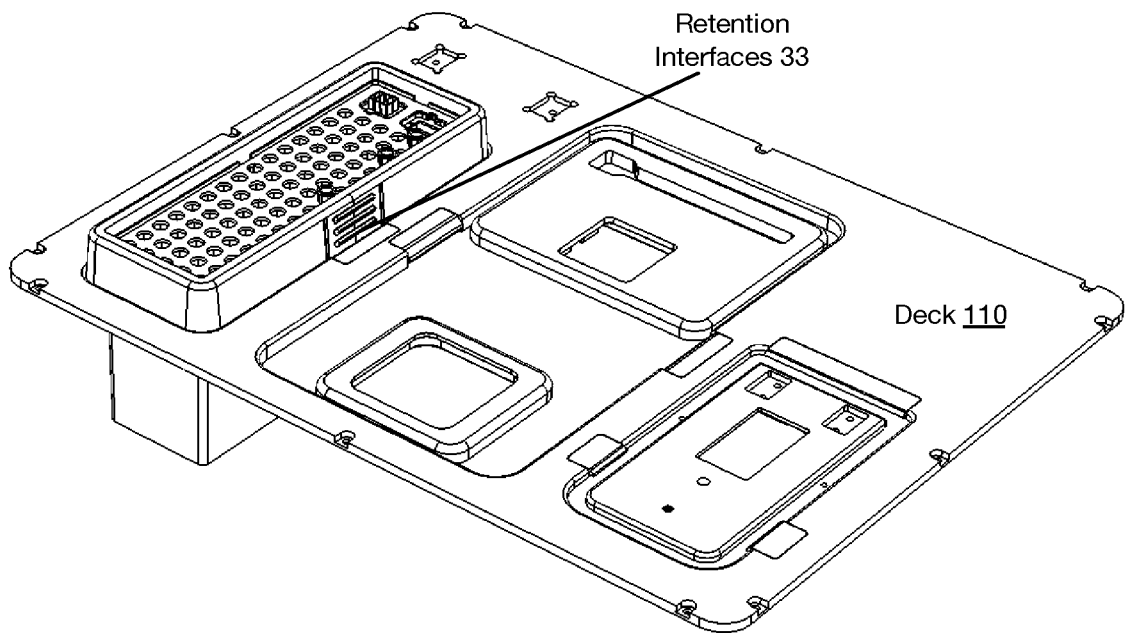
Figure 8I:
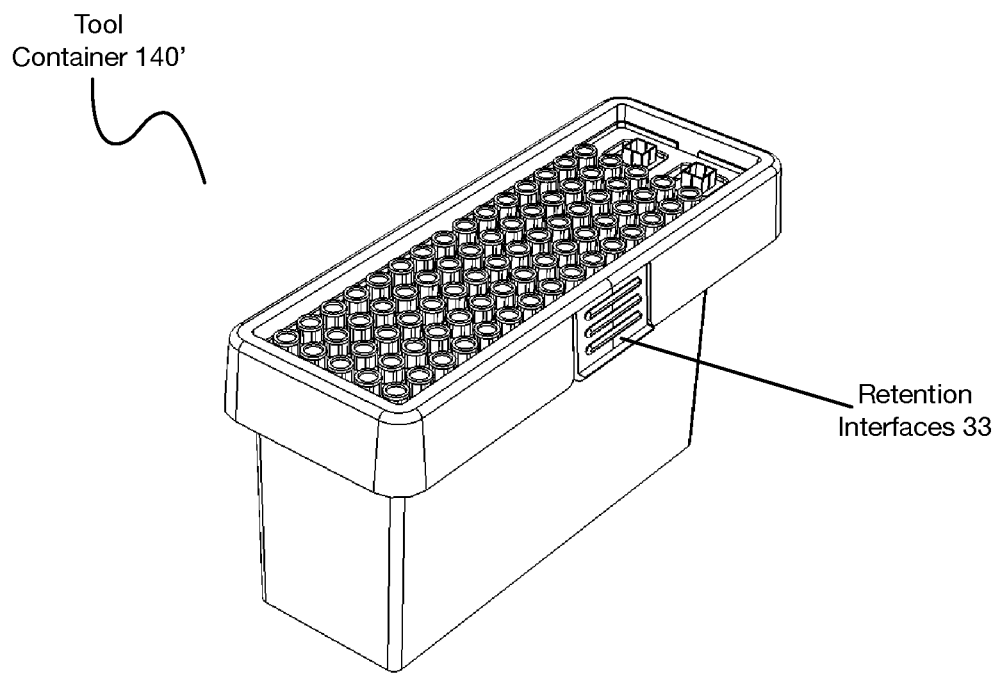

In relation to FIG. 8A, the third subset of retention elements 23 at region 113 can include a set of snap ledges positioned about region 113 (e.g., at contralateral sides of region 113), in a manner that complements corresponding retention interfaces 33 of the tool container. In more detail, as shown in FIGS. 8H and 8I, the retention interfaces 33 of the tool container 140 can include a set of tabs (e.g., flexible tabs) that can be compressed from a baseline position to be positioned at region 113, where release from the compressed configuration allows the set of tabs to latch with the snap ledges. The set of tabs of the retention interfaces 33 can further include gripping features (e.g., bumps, etc.) that allow a user to compress the set of tabs easily.

In variations of the retention elements of the deck no described above can, however, include other suitable features or be configured relative to associated elements in another suitable manner.

2.1.5 Deck-Supported Element: Heating and Cooling Subsystem

As shown in FIGS. 1A-1D and 2B, the system 100 can include a heating and cooling subsystem 150, which functions to transfer heat to and/or from desired regions of the reagent cartridge 120 and/or the sample processing cartridge 130. The heating and cooling subsystem 150 can additionally or alternatively function to maintain desired temperatures within internal volumes of the system 100. In variations, the heating and cooling subsystem 150 can include one or more units of: heating elements (e.g., Peltier heating elements, resistive heating elements, other heating elements), cooling elements (e.g., Peltier cooling elements, chilled aluminum block, fluidic pathway system to circulate coolant, etc.), thermal contact or non-contact bodies for transferring heat to or from the heating and cooling elements to other objects, heat sinks, fans, temperature sensors, and thermal control circuitry (e.g., with electrical coupling to processing elements of the base 180 described in more detail below). In variations, the cooling element(s) can maintain storage volumes and/or samples between 2 and 8 degrees Celsius, further preferably at 4 degrees Celsius. Additionally or alternatively, the cooling elements can maintain one or more storage volumes/samples at any suitable temperature (e.g. below 2 degrees Celsius, above 8 degrees Celsius, etc.).

One or more portions of the heating and cooling subsystem 150 can pass into openings of the deck no to thermally interface with or otherwise couple with desired portions of other system elements (e.g., reagent cartridges, sample processing cartridges, tool container, etc.) supported by the deck 110, in order to provide heat transfer functions for various applications. Alternatively, the deck no can be composed of a thermally conductive material at desired regions for heat transfer applications, and portions of the heating and cooling subsystem 150 can be configured to contact the thermally conductive material regions of the deck 110 for heat transfer.

In the specific example shown in FIG. 2B, the heating and cooling subsystem 150 includes a set of thermal bodies that thermally interface the heating elements with desired portions of the reagent cartridge 120 and the sample processing cartridge 130 supported by the deck 110. The set of thermal bodies includes a first thermal body 156' (e.g., thermal plate) passing through an opening of the deck 110' and configured to interface with the first domain 121' of the reagent cartridge 130' described above, where the first thermal body 156' includes an array of recesses for surrounding storage volumes of the first domain 121' (e.g., to provide a chilled environment for materials stored in the storage volumes of the first domain 121'). As shown in FIG. 2B, the set of thermal bodies can also include a second thermal body 157' (e.g., thermal plate) passing through an opening of the deck 110' and configured to interface with the third domain 123' of the reagent cartridge 130' described above, where the second thermal body 157' includes an array of recesses for surrounding storage volumes of the third domain 123' (e.g., to transfer heat for PCR and/or other heating operations for processes conducted within storage volumes of the third domain 123'). As shown in FIGS. 2B and 6A, the set of thermal bodies can also include a third thermal body 158' (e.g., thermal plate) passing through an opening of the deck 110' and configured to interface with the set of microwells 34 of the sample processing chip 132 described above, where the third thermal body 158' provides a substantially planar substrate for uniform heat transfer to and from microwells of the sample processing cartridge 130.

Figure 2D:
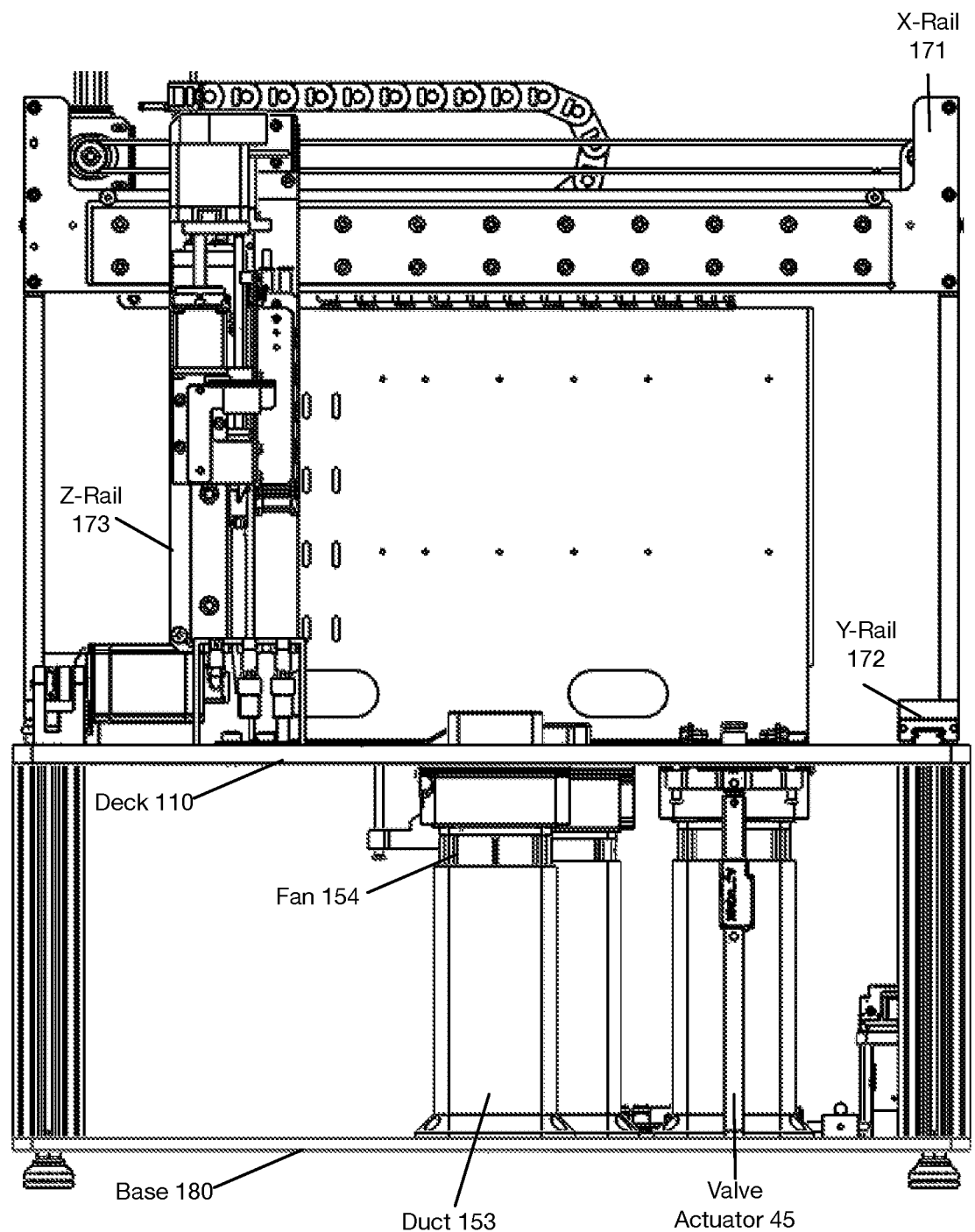
Figure 2E:
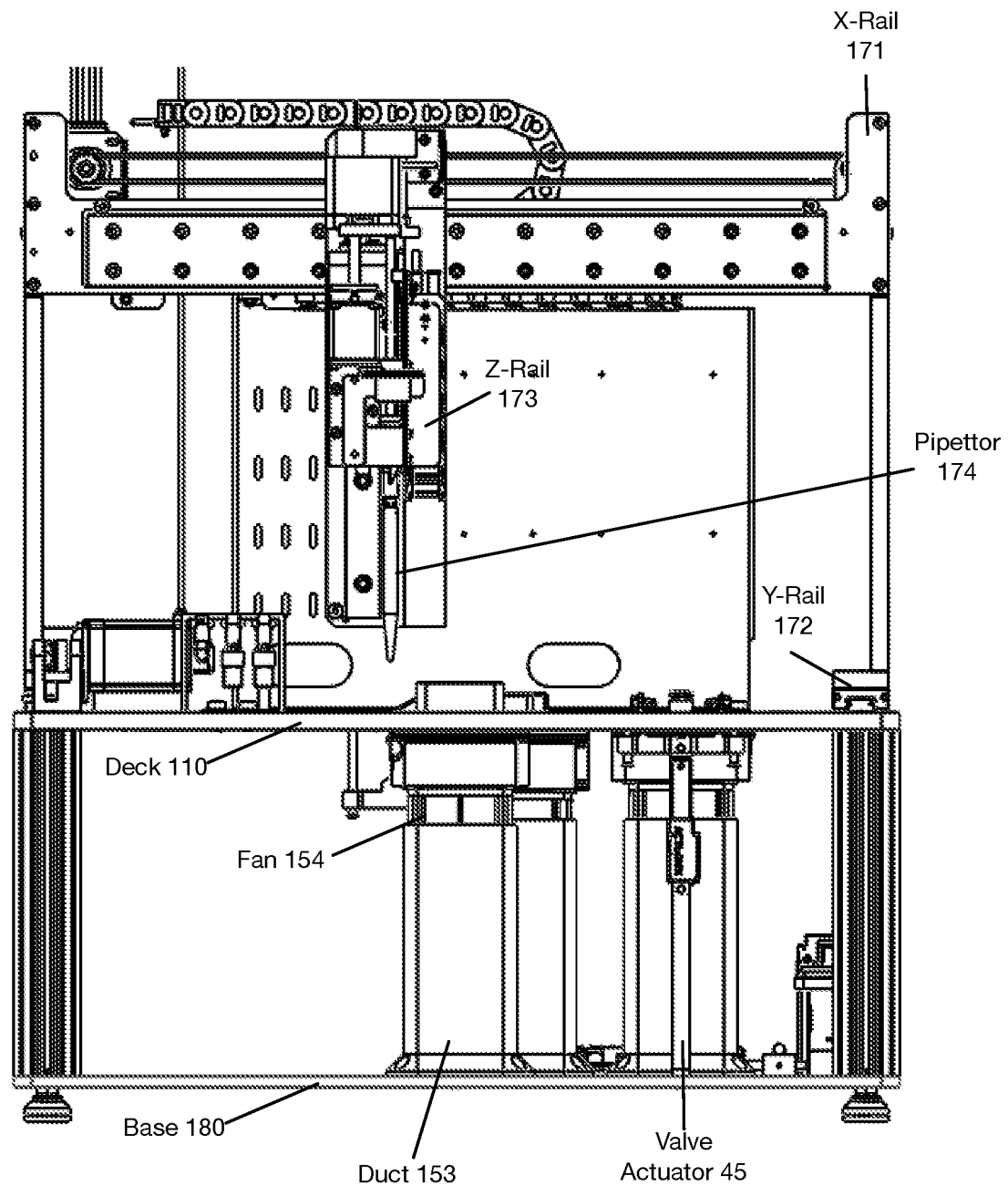
Figure 2F:
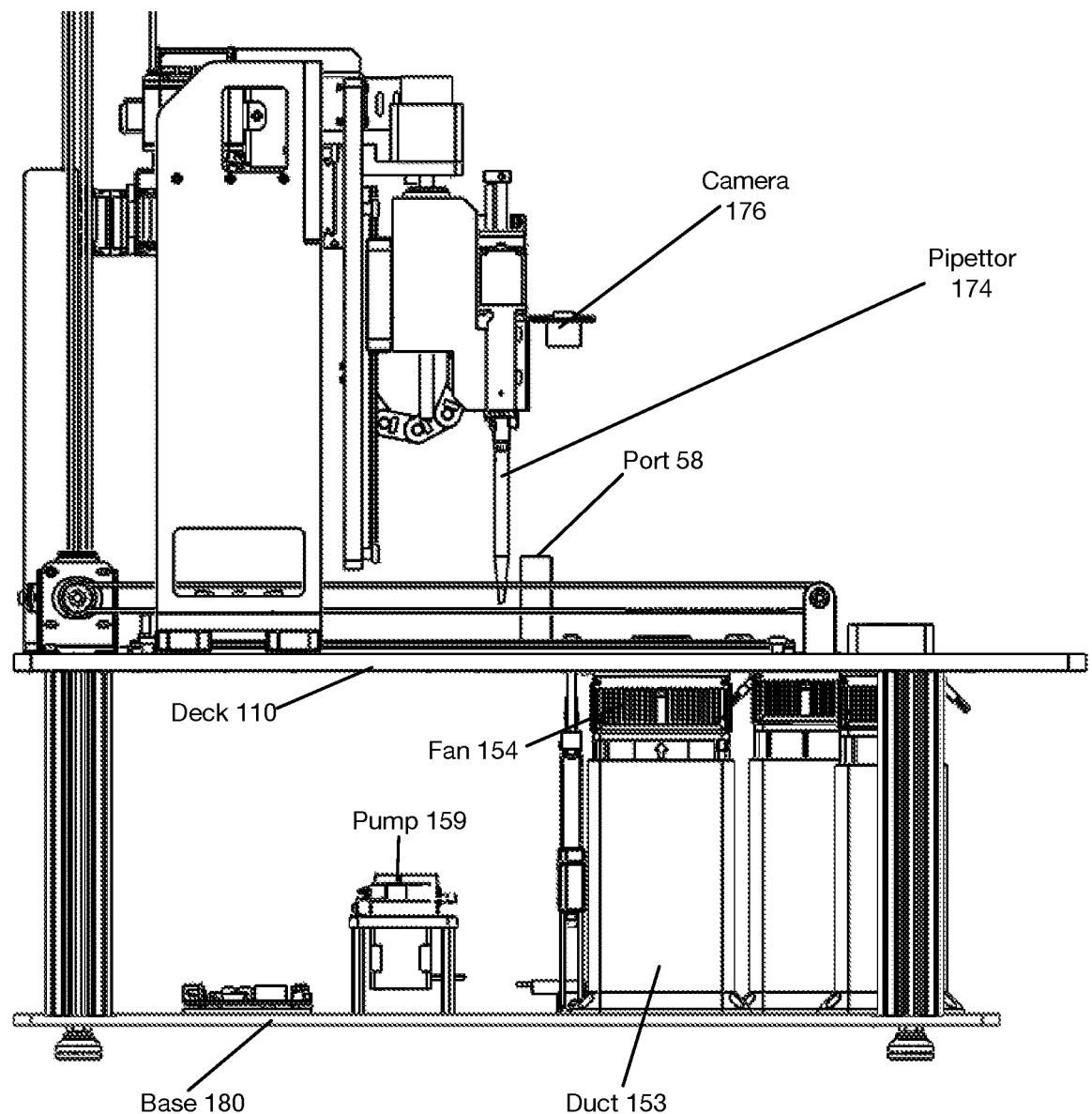

In variations, the set of thermal bodies can be coupled to heat sink elements 155 (e.g., at sides of the thermal bodies away from interfaces with reagent cartridges/sample processing cartridges), in order to provide greater surface area for heat transfer. Furthermore, as shown in FIGS. 2D-2F, areas between the deck 110 and the base 180 described in more detail below can include one or more fans 154 and/or ducts 153, in order to provide thermal mechanisms for convective heat transfer away from the set of thermal bodies as needed. Furthermore, in variations described above, one or more portions of the heating and cooling subsystem 150 (e.g., thermal bodies, etc.) can include features that facilitate retention of corresponding cartridges (e.g., reagent cartridges, sample processing cartridges, etc.) in position.

In variations, one or more of the thermal bodies and/or other portions of the heating and cooling subsystem 150 can be coupled to actuators that move the thermal bodies into and out of thermal communication with elements supported by the deck 110; however, variations of the system 100 can omit actuators of the heating and cooling subsystem 150.

2.1.6 Deck-Supported Element: Pumping Subsystem

As shown in FIGS. 1A, 2B, and 6A, the system 100 can include a pumping subsystem 157 (e.g., coupled to the deck 110 and/or base 180), which functions to provide positive pressure and/or negative pressure to desired portions of the sample processing cartridge 130 described above. In more detail, the pumping subsystem 157 can function to drive fluid flow from the inlet reservoir 133 and into the sample processing chip 132 of the sample processing cartridge 130. Additionally or alternatively, the pumping subsystem 157 can function to remove fluid from the waste containment region 137 of the sample processing cartridge 130 and into an external waste receptacle. In variations, the pumping subsystem 157 can include one or more ports 58 (e.g., vacuum ports) configured to interface with the sample processing cartridge 130 through openings in the deck 110, one or more pumps (e.g., vacuum pumps, peristaltic pumps, etc.) coupled to the ports 58, one or more manifolds to provide pressure driving pathways coupled to the pump(s), one or more pressure sensors configured to detect pressure levels along pressure pathways, and/or one or more control circuit elements configured to control operation of the pumping subsystem 157 (e.g., with electrical coupling to processing elements of the base 180 described in more detail below). As such, in variations, portions of the pumping subsystem 157 not directly coupled to the sample processing cartridge 130. can be situated between the deck 157 and the base.

In variations, the port(s) 58 of the pumping subsystem 157 can be coupled (e.g., physically connected, fluidically connected, etc.) suitable regions of the sample processing cartridge 130 (e.g. inlet, wells, etc.), and can additionally or alternatively be coupled to the reagent cartridge 120, another fluidic pathway of the system 100, or any other suitable component of the system 100.

In a first specific example, as shown in FIGS. 2F and 6A, the pumping subsystem 157 includes a pump 59 (e.g., peristaltic pump) arranged between the deck 110 and the base 180, and coupled to the waste containment region at the waste outlet 51, through a coupling arranged at a bottom broad surface of the base substrate 131 of the sample processing cartridge 130, wherein the pump 59 can draw fluid through the sample processing chip 132 in forward and reverse directions by applying negative and/or positive pressure accordingly. Additionally or alternatively, the pumping subsystem 157 can draw fluid from the inlet reservoir 133 and through the sample processing chip 132 at a predetermined pressure (e.g., −0.25 psi or −1 psi or −2.5 psi) according to triggering events associated with the fluid level detection subsystem 159 described in more detail below.

In relation to the sample processing cartridge 130 and forces applied by the lid-opening tool 145 to transition the lid 135 between closed and open states, retention elements described in Section 2.1.4 above can provide a retention force that balances/counteracts a force applied by the lid-opening tool 145 to open the lid 135, as described above. Additionally or alternatively, one or more portions of the pumping subsystem 157 can retain the sample processing cartridge 130 in position and provide a retention force that balances/counteracts a force applied by the lid-opening tool 145 to open the lid 135, as described above. In a specific example, the port 58 can couple with the sample processing cartridge 130 to provide a counteracting force to the lid-opening tool 145. However, other portions of the system 110 can additionally or alternatively provide a counteracting force.

2.1.7 Deck-Supported Element: Fluid Level Detection Subsystem

Figure 9:
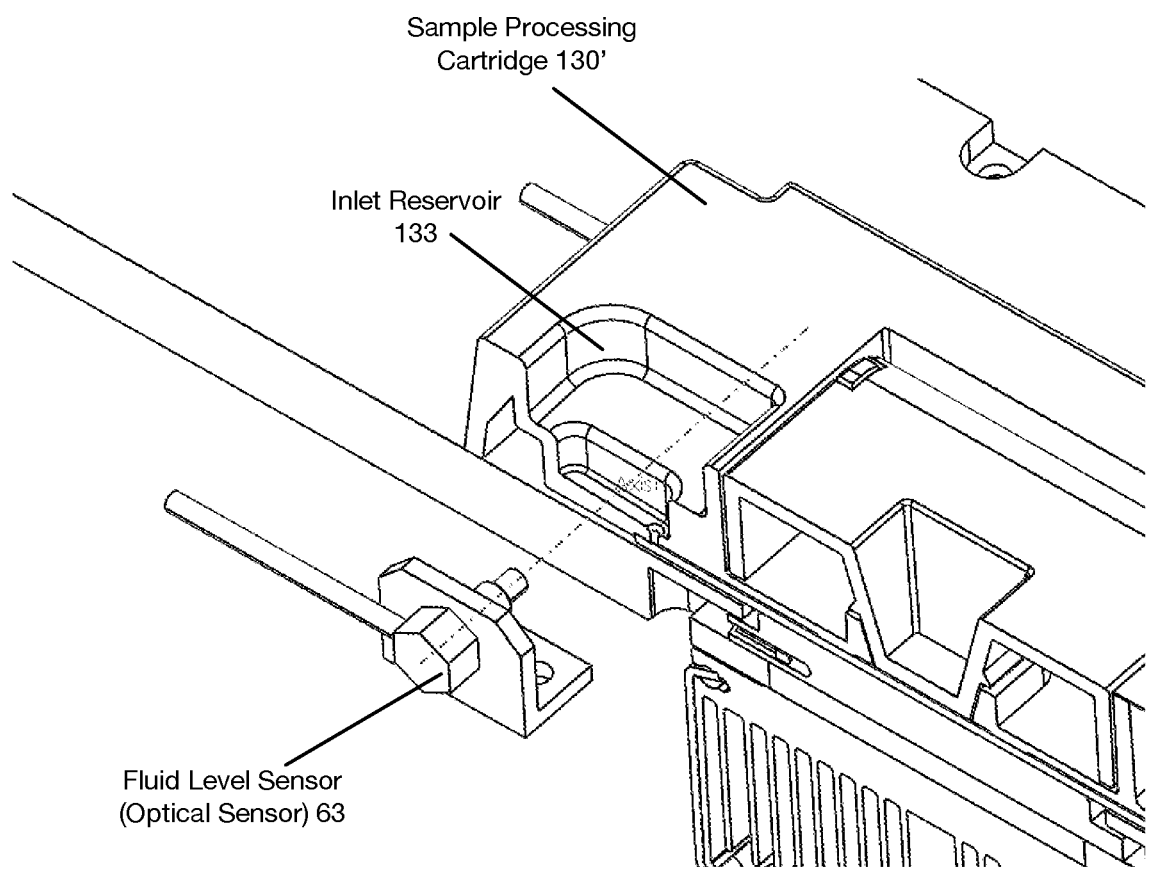
FIG. 9 depicts an example of a fluid level detection subsystem of a system for automated single cell sample processing.

As shown in FIGS. 1A, 2B, and 9, the system 100 can include a fluid level detection subsystem 159 at least partially supported by the deck 110 and configured to interface with the sample processing cartridge 130. The fluid level detection subsystem 159 functions to detect and/or measure a fluid parameter (e.g. a binary presence of fluid, a volume of fluid, a fluid flow rate, a fluid type etc.) associated with fluid at the sample processing cartridge 130 and/or other fluid processing elements of the system 100. In variations, the fluid level detection subsystem 159 can include a fluid level sensor 63 coupled to fluid level control circuitry (e.g., with electrical coupling to processing elements of the base 180 described in more detail below).

A unit of the fluid level sensor 63 can determine a fluid parameter associated with the inlet reservoir 133 (e.g. fluid passing from the inlet reservoir to microwells) of the sample processing cartridge 130. A unit of the fluid level sensor 63 can additionally or alternatively determine a fluid parameter associated with an outlet (e.g. fluid passing from microwells to outlet, fluid passing from outlet to waste containment region, etc.) of the sample processing cartridge 130. A unit of the fluid level sensor 63 can additionally or alternatively determine a fluid parameter associated with the waste containment region (e.g. volume of fluid in waste containment region) of the sample processing cartridge 130, or any other suitable fluid parameter. The fluid level sensor 63 can include any or all of: an optical sensor, pressure sensor, temperature sensor (e.g. to detect a fluid of certain temperature in a fluidic pathway), or any other suitable sensor configured to detect the presence of fluid and optionally determine a value associated with the fluid (e.g. volumetric flow rate, etc.) in the sample processing cartridge.

In a first variation, the system includes an optical sensor 63 configured to detect the presence of fluid being transferred from the inlet to the set of wells. In an example, an infrared (IR) emitter/detector pair is used to determine the presence of fluid and a volume of the fluid being transferred (e.g. further based on the duration of time that the fluid is present) at the inlet reservoir 133 of the sample processing cartridge 130.

In the specific example shown in FIGS. 2B and 9, the fluid level detection subsystem 159 includes an IR emitter 63a displaced from and opposing an IR detector 63b across the inlet reservoir 133 of the sample processing cartridge 130, where the IR emitter 63a and IR detector 63b are configured to be positioned within an underside internal portion of the base substrate 131 of the sample processing cartridge 130, to pass IR radiation across walls and an internal volume of the inlet reservoir 133, thereby enabling fluid level detection. Variations of the fluid level sensor 63 can, however, be configured in another suitable manner.

2.1.8 Deck-Supported Element: Separation Subsystem and Operation Modes

As shown in FIGS. 1A, 2B, and 10A-10C, the system 100 can include a separation subsystem 160, which functions to facilitate separation of target material from non-target material (e.g., using magnetic forces, using other forces). In variations, the separation subsystem 160 can include embodiments, variations, and examples of components described in U.S. Application 62/866,726, titled "System and Method for Target Material Retrieval from Microwells" and filed on 26 Jun. 2019, which is herein incorporated in its entirety by this reference. However, variations of the separation subsystem 160 can additionally or alternatively include other components.

Figure 10A:
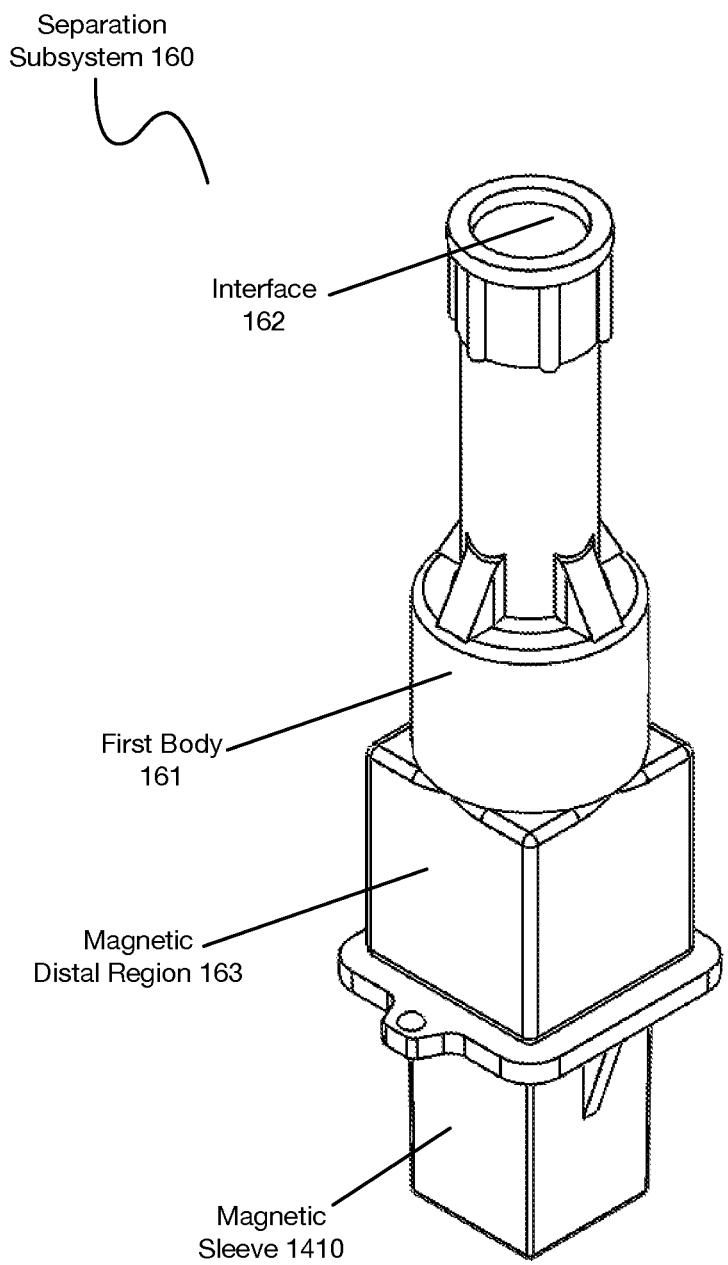

In one variation, as shown in FIGS. 10A-10C, the separation subsystem 160 can include a first body 161 including an interface 162 to the fluid handling subsystem (e.g., pipette interface) of the gantry 170 described below, and a magnetic distal region 163 configured to provide magnetic forces for target material separation. In this variation, the magnetic distal region 163 can be configured to couple with one or more units of the magnetic sleeves 1410 (e.g., of tool container 140) described above, where the magnetic sleeves 1410 can be disposable elements. Furthermore, the interface 162 can be configured to couple to a pipetting head coupled to the gantry 170 described in more detail below, in order to facilitate target or non-target material retrieval by way of magnetic forces, fluid aspiration, and/or fluid delivery operations provided by the pipetting head. As such, the system 100 can include a separation mode in which the gantry 170 transports the first body 161, coupled to the magnetic sleeve 1410, between the sample processing cartridge 130 and the reagent cartridge 120 for magnetic separation of target material from a sample. Furthermore, embodiments of methods implemented using the separation subsystem 160 can produce rapid retrieval of target material, with a retrieval efficiency of >90% where only magnetic particles coupled to target material (or non-target material) of the sample are retrieved. The separation subsystem 160 can thus function to produce increased selective retrieval efficiency can thus reduce downstream costs in relation to processing reagent and other material costs (due to reduced volumes needed, due to reduced splits in biochemistry reactions) and processing burden.

As shown in FIG. 10A, the first body 161 can include an interface 162 to the fluid handling subsystem of the gantry 170 described below, where the interface includes a coupling region that complements a corresponding coupling region of the fluid handling subsystem. The coupling region of the interface 162 can operate by: a magnetic coupling mechanism; a press fit; a snap fit, a screwing mechanism; a male-female connection; or another suitable mechanism for providing reversible coupling with the fluid handling subsystem.

The magnetic distal region 163 of the first body 161 can include or be composed of a material for providing a permanent magnet, or can alternatively be configured as an electromagnet (e.g., with coupling to suitable electronics of the system Dm). In variations, the magnetic distal region 163 can be composed of one or more of: alnico, neodymium, neodymium iron boron, samarium cobalt, ferrite, and any other suitable magnetic material. In morphology, the magnetic distal portion 163 can complement a morphology of the magnetic sleeve 1410, such that units of the magnetic sleeve 1410 can couple (e.g., reversibly couple) with the magnetic distal portion. Furthermore, the morphology and pole configuration of the magnetic distal portion 163 is such that nearly normal magnetic force is applied to majority of the target microwells from where entrapped particles are being removed.

The magnetic sleeve 1410 can include a first region 1410a configured to interface with the sample processing chip 132, for instance, through access region 134, in order to enable transfer of material from the sample processing chip 132. The magnetic sleeve 1410 can also include a second region 1410b for coupling with the magnetic distal portion 163 of the first body 161, and an internal cavity 1410c passing from the first region to the second region. The magnetic sleeve 1410 functions to provide structures that separate the first body 163 from physically contacting wells or other sensitive material of the sample processing chip 132, and to support application of a magnetic field to the desired regions for retrieval of target material (or non-target material). The magnetic sleeve 1410 can also function to prevent sample cross contamination, by serving as a disposable component that can be discarded between uses of the system 100.

The magnetic sleeve 1410 can be morphologically prismatic with an internal cavity 1410c, where the cross section of the magnetic sleeve 1410 along its longitudinal axis is defined by a polygonal perimeter, an ellipsoidal perimeter, an amorphous perimeter, or a boundary of any other suitable shape (e.g., closed shape, open shape). The cross section of the magnetic sleeve 1410 can complement a shape of a footprint of the microwell region of the sample processing chip 132, but may alternatively not complement a shape corresponding to the sample processing chip 132. The magnetic sleeve 1410 preferably has a wall thickness that supports application of a magnetic force, from the magnetic distal portion 163, to the sample processing chip 132 interfacing with the first region 1410a of the magnetic sleeve 1410. The wall thickness can be constant or non-constant along the length of the adaptor 210. In examples, the wall thickness can range from 0.2 to 3 mm thick; however, in other examples, the wall thickness can have any other suitable thickness. The surface of the magnetic sleeve 1410 that receives the magnetic particles is made smooth (say surface finish better than SPIB1) such that the small magnetic particles (1-3 micron) do not gets entrapped in the surface during the bead capture onto its surface and subsequent release to another receptacle.

The magnetic sleeve 1410 can additionally or alternatively include structural features that enable separation operation modes of the separation subsystem 160. For instance, in relation to release of the magnetic sleeve 1410 from the pipetting head (described in more detail below), the magnetic sleeve 1410 can include a protrusion 1410*d* configured to allow another object (e.g., sleeve stripping tool 165) to provide a force against the protrusion 1410*d* to release the magnetic sleeve 1410 from the first body 161.

As described above, the magnetic sleeve 1410 couples, at a first region 1410*a*, to a region of the sample processing chip 132 exposed through access region 134, in order to facilitate application of magnetic force to the region, and to enable drawing of material (e.g., target or non-target material coupled to magnetic particles) into the magnetic sleeve 1410 for further downstream processing. The magnetic sleeve 1410 can thus include a seal at the first region 1410*a*, in order to facilitate mechanisms for drawing target material from the sample processing chip 132 into the magnetic sleeve 1410. The seal can be a separate element or an element integrated with the magnetic sleeve 1410. The magnetic sleeve 1410 can, however, omit a seal at the first region 1410*a*.

The magnetic sleeve 1410 can be composed of a polymeric material (e.g., plastic) that does not adversely affect the magnetic field applied by the magnetic distal portion 163 during operation. The magnetic sleeve 1410 can additionally or alternatively include (e.g., include particles of) or be composed of a material (e.g., metallic material) that is magnetic or can produce an induced magnetic field to support applications of use of the system 100. The magnetic sleeve 1410 can additionally or alternatively be composed of any other suitable material. Distributions of the material(s) of the magnetic sleeve 1410 can be homogenous or non-homogenous through the body of the adaptor, in relation to desired magnetic effects at the capture region of the sample processing chip 132. The internal cavity iztioc of the magnetic sleeve 1410 can include a medium (e.g., magnetic medium, etc.), or can alternatively not include any medium.

Figure 11A:
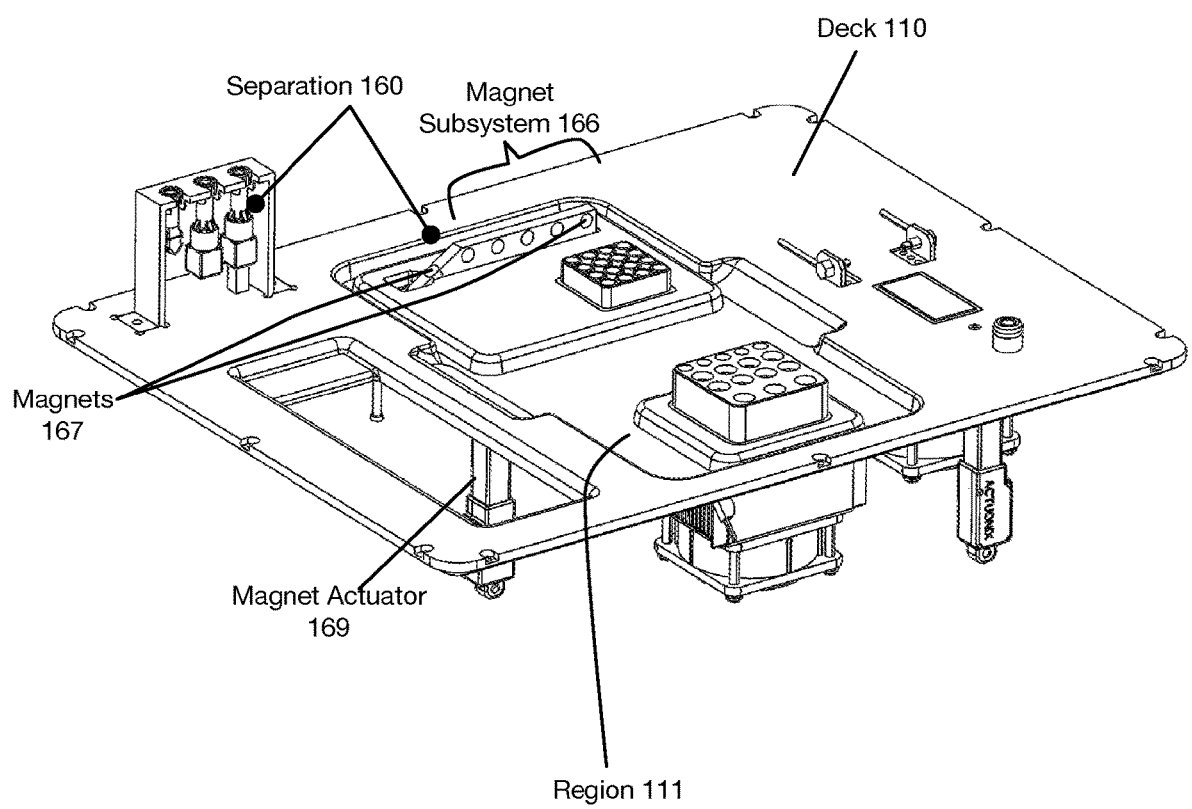
FIGS. 11A-11B depict variations of a second subset of components used for material separation in a system for automated single cell sample processing.
Figure 11B:
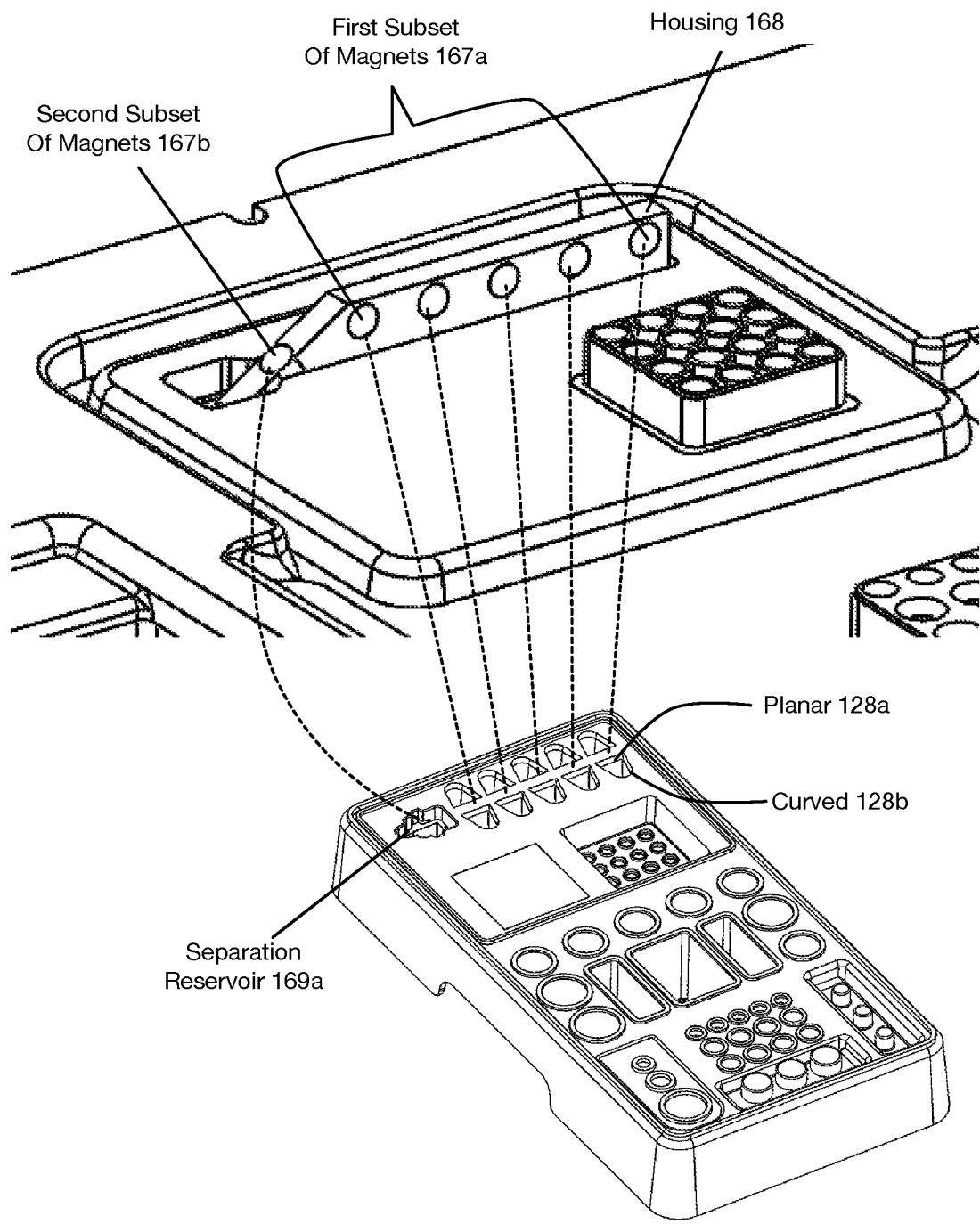

As shown in FIGS. 1A, 2B, and 11A-11B, in variations, the separation subsystem 160 can include a magnet subsystem 166 including a set of magnets 167 within a housing 168, where the magnet subsystem 166 further includes a magnet actuator 169 configured to move the set of magnets 167 relative to the deck 110 (e.g., through in opening in the deck no), and into/out of alignment with one or more separation reservoirs 129 of the reagent cartridge 120 described above. The magnet actuator 169 can also be coupled to control circuitry (e.g., at the base 180) described in more detail below. Furthermore, the magnet actuator 169 can be configured to transition the set of magnets between a retracted state and an extended state, wherein in the extended state, the set of magnets passes into the first region of the deck (e.g., as shown in FIGS. 11A and 11B). As such, the separation subsystem 160 can also include elements that are supported by the deck 110 and/or base 180, in order to enable operations for separating target material from non-target material.

In variations, the set of magnets 167 can include one or more permanent magnets and/or electromagnets (e.g., with coupling to suitable electronics of the system 100). Permanent magnets can be composed of one or more of: alnico, neodymium, neodymium iron boron, samarium cobalt, ferrite, and any other suitable magnetic material.

In the example shown in FIGS. 11A-11B, the set of magnets 167 can include a first subset of magnets 167*a* arranged in a linear array (e.g., for performance of purification operations at the reagent cartridge 120), where the positions of the first subset of magnets 167*a* correspond to positions of volumes of the fifth domain 125' for particle separation/purification, described in relation to the reagent cartridge 120' above and workflows in Section 3 below. In the example shown in FIG. 11A-11B, the set of magnets 167 also includes a second subset of magnets 167*b* (e.g., one or more magnets) displaced from or otherwise offset from an axis associated with the first subset of magnets 167*a*, in order to interact with a separation reservoir 129*a* of the reagent cartridge 120 (e.g., for initial bead retrieval). The set of magnets 167 can, however, be arranged in another suitable manner (e.g., in relation to distributed arrays, in relation to number, etc.) in relation to providing suitable interactions with separation reservoirs 129 of the reagent cartridge 120 or other cartridges.

The housing 168 functions to surround the set of magnets 167, and to provide smooth operation in relation to transitioning the set of magnets 167 into/out of alignment with corresponding portions of the reagent cartridge 120. Thus, as shown in FIG. 11B, in relation to configurations where there is a first subset of magnets 167*a* and a second subset of magnets 167*b*, the housing 168 can include a first surface (e.g., first planar surface) tracking the first subset of magnets 167*a*, and a second surface (e.g., second planar surface) tracking the second subset of magnets 167*b*, wherein the first surface 168*a* and the second surface 168*b* are angled away from each other. In this variation, a pair of opposing walls can extend from the first surface and the second surface, in order to promote smooth operation (e.g., sliding operations) of the housing 168 and magnets through the deck 110 in order to interface with the reagent cartridge 120.

In relation to the reagent cartridge 120', as shown in FIGS. 3A and 11B, volumes of the reagent cartridge 120 configured for magnetic separation can each include a planar surface 128*a*, or other surface complementary to the housing 168 at sides configured to be closest to the housing 168 during operation (e.g., in the extended magnet states). Furthermore, volumes of the reagent cartridge 120 configured for magnetic separation can each include a second surface 128*b* (e.g., curved surfaces) displaced away from the housing 168 for aspiration and/or delivery of fluids by a pipettor coupled to the gantry 170 described below. Cross sections taken longitudinally through separation volumes/reservoirs 129 of the reagent cartridge 120 can further be tapered toward a base of the reagent cartridge 120, such that separation operations require a lower volume of fluid and/or provide more efficient aspiration and separation of target from non-target material.

Figure 12A:
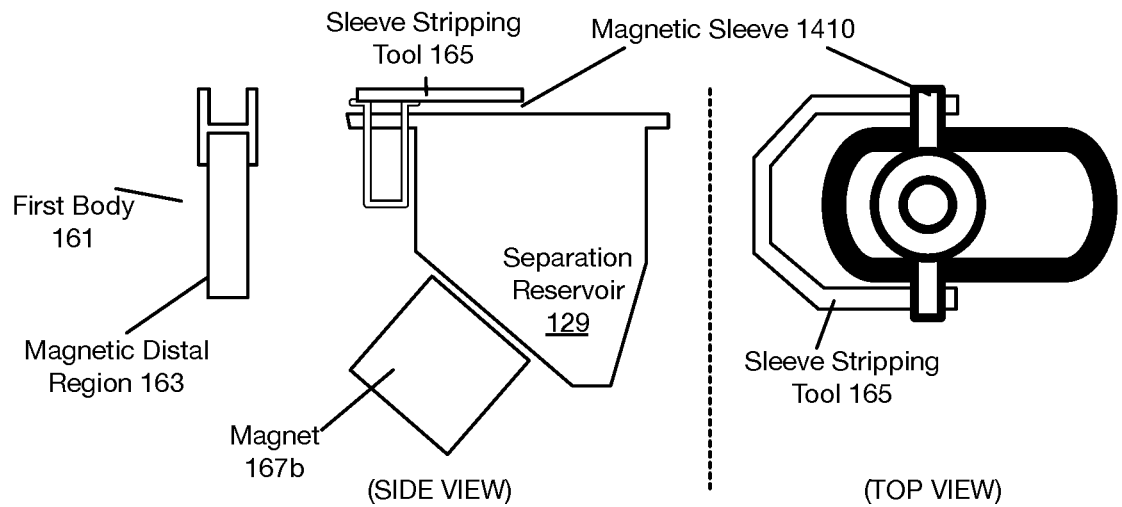
FIGS. 12A-12J depict operation modes of a separation subsystem associated with a system for automated single cell sample processing.

As shown in FIGS. 12A through 12J, the separation subsystem 160 can provide a sequence of operation modes for material separation, where, as shown in FIG. 12A, the operation modes involved specific system structure configurations of: a first body 161 coupled with a pipetting head or other actuatable component (e.g., described in relation to the gantry 170 below), the first body having a magnetic distal region 163, a magnetic sleeve 1410, a sleeve stripping tool 165, a separation reservoir 129, and a magnet 167*b* of the set of magnets 167 described above.

Figure 12B:
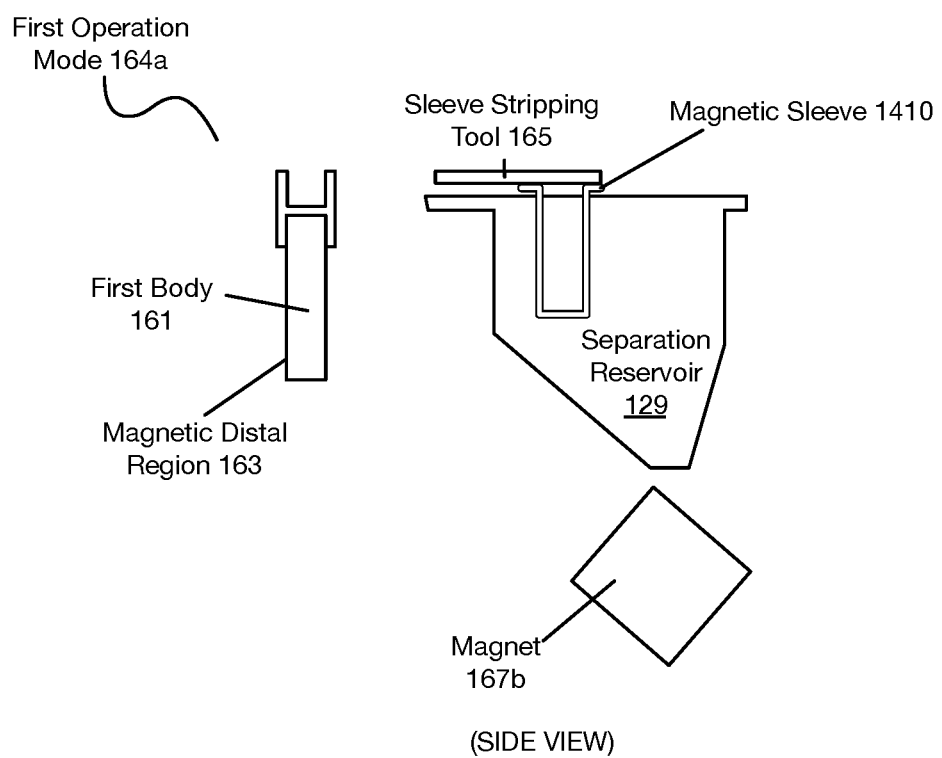

In more detail, as shown in FIG. 12B, the separation subsystem 160 can provide a first operation mode 164*a*, where the first operation mode 164*a* is a baseline operation mode in which the first body 161 is uncoupled from a pipette interface or other actuatable component (e.g., described in relation to the gantry 170 below) and the magnetic distal region 163 of the first body 161 is uncoupled from the magnetic sleeve 1410. The magnetic sleeve 1410 is further retained by sleeve stripping tool 165 above the separation reservoir 129 (or in variations, at another position), and the magnet 167*b* is displaced away from the separation reservoir 129 (e.g., by magnet actuator 169 described above).

Figure 12C:
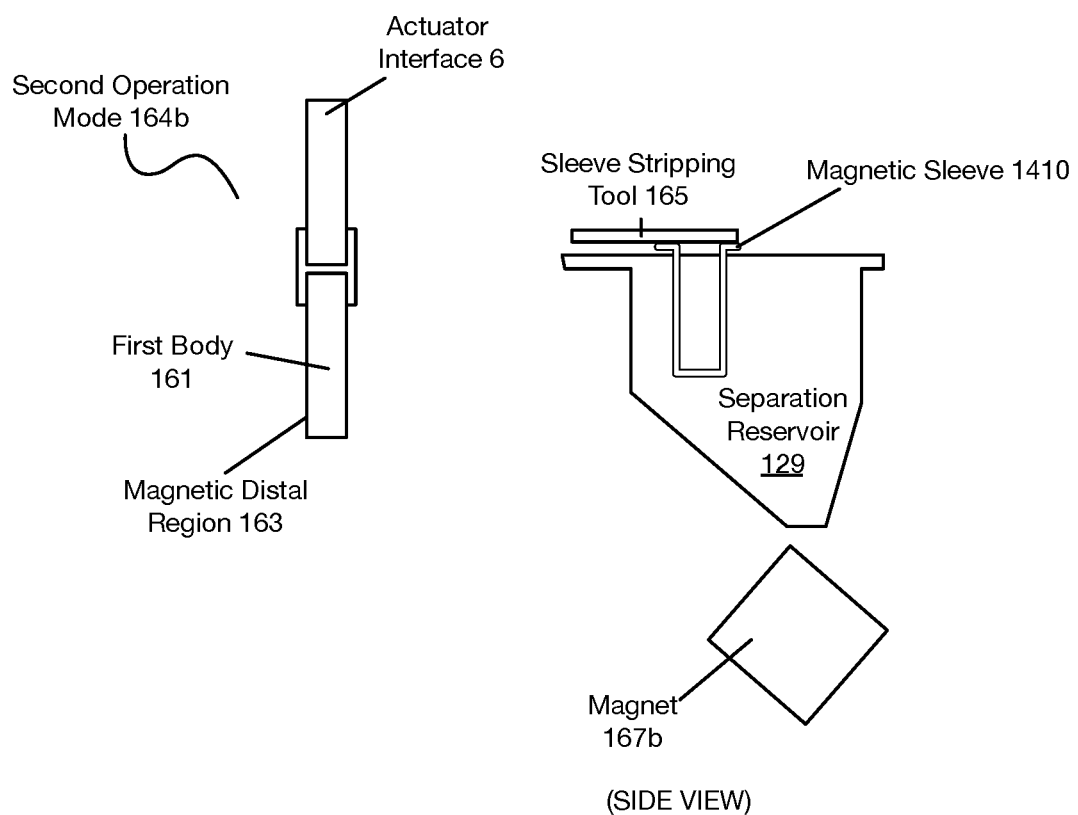

As shown in FIG. 12C, the separation subsystem 160 can provide a second operation mode 164*b*, where the second operation mode 164*b* is an initializing operation mode in which the first body 161 is coupled with a pipette interface or other actuator interface 6 (e.g., described in relation to the gantry 170 below) and the magnetic distal region 163 of the first body 161 is uncoupled from the magnetic sleeve 1410. The magnetic sleeve 1410 is further retained by sleeve stripping tool 165 above the separation reservoir 129, and the magnet 167*b* is displaced away from the separation reservoir 129 (e.g., by magnet actuator 169 described above).

Figure 12D:
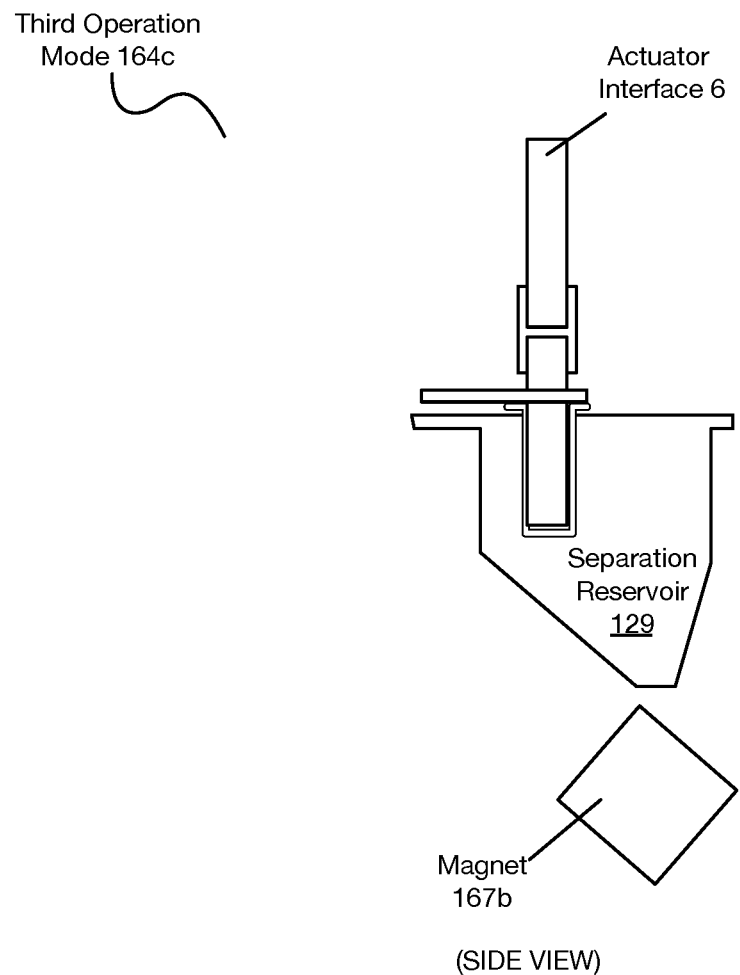

As shown in FIG. 12D, the separation subsystem 160 can provide a third operation mode 164*c*, wherein, in the third operation mode 164*c*, the first body 161 is coupled with a pipette interface or other actuator interface 6 (e.g., described in relation to the gantry 170 below) and moved into alignment with the separation reservoir 129. In the third operation mode 164*c*, the magnetic distal region 163 of the first body 161 is coupled with the magnetic sleeve 1410 above the separation reservoir 129 in the retained position of the magnetic sleeve 1410. In the third operation mode 164*c*, magnet 167*b* is displaced away from the separation reservoir 129 (e.g., by magnet actuator 169 described above).

Figure 12E:
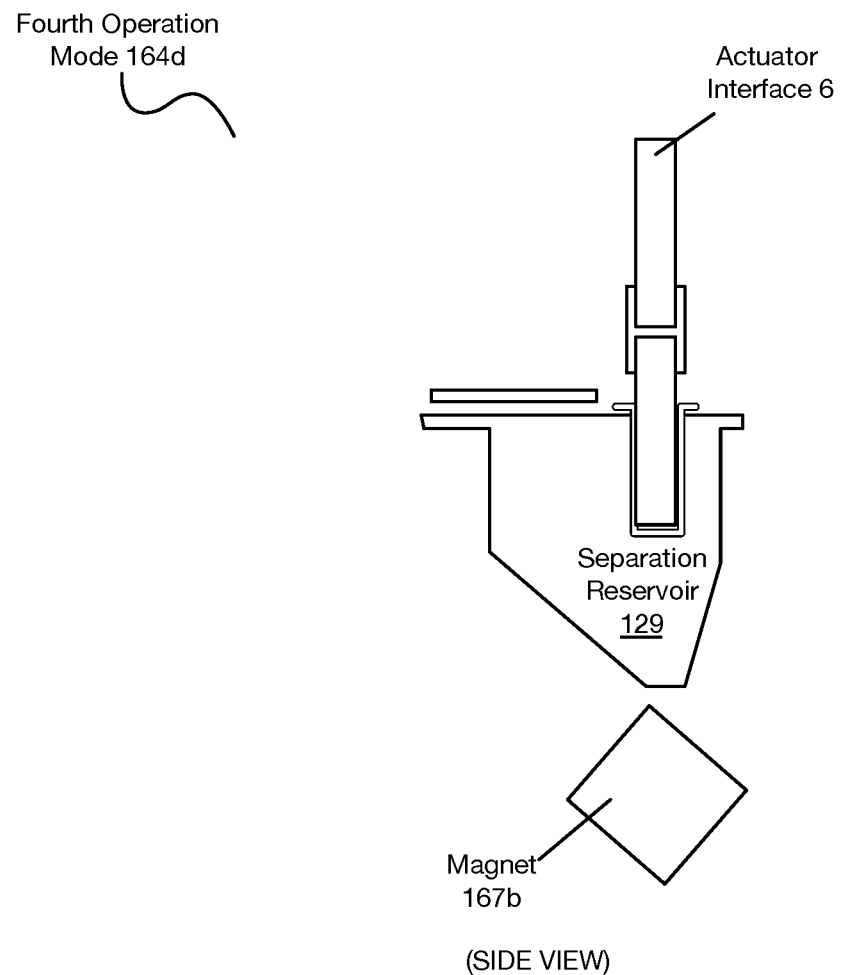

As shown in FIG. 12E, the separation subsystem 160 can provide a fourth operation mode 164*d*, wherein, in the fourth operation mode 164*d*, the first body 161 is coupled with a pipette interface or actuator interface 6 (e.g., described in relation to the gantry 170 below) and the magnetic distal region 163 of the first body 161 is coupled with the magnetic sleeve 1410 above the separation reservoir 129. In the fourth operation mode 164*d*, the pipetting head (or other actuatable component) moves the first body 161 and magnetic sleeve 1410 out of the retained position provided by the sleeve stripping tool 165, to prepare for extraction of material (e.g., functionalized particles from the sample processing cartridge) and/or delivery of material from the pipette interface, coupled to the first body and magnetic sleeve, into the separation reservoir 129. In the fourth operation mode 164*d*, magnet 167*b* is displaced away from the separation reservoir 129 (e.g., by magnet actuator 169 described above).

Figure 12F:
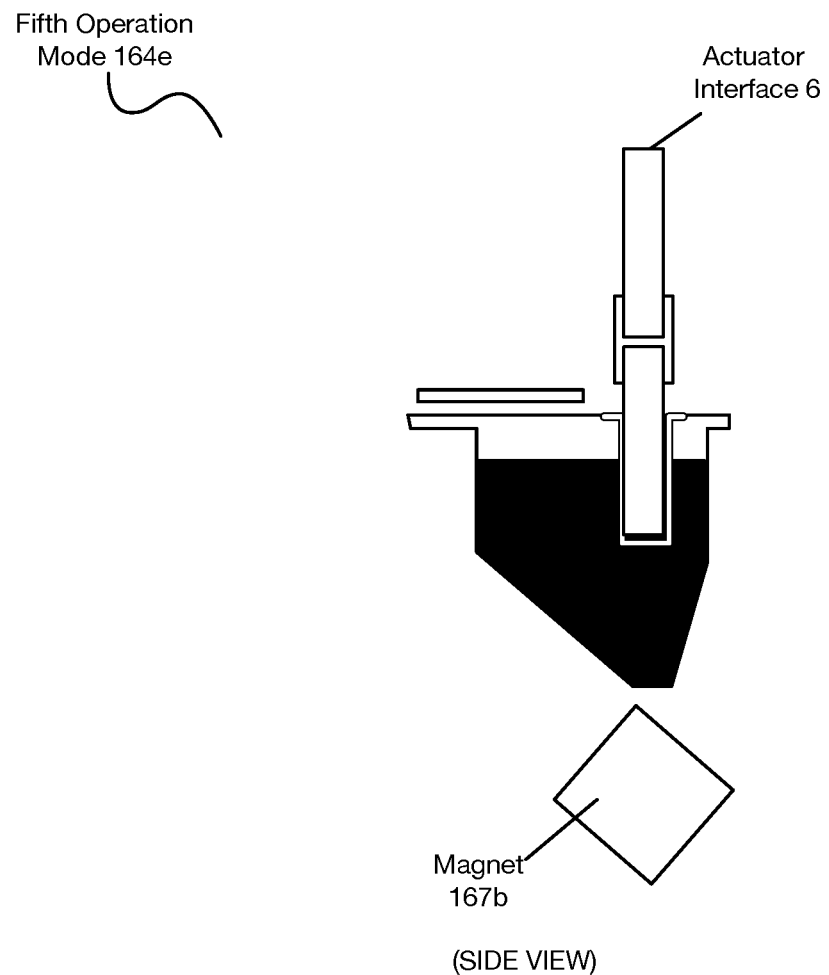

As shown in FIG. 12F, the separation subsystem 160 can provide a fifth operation mode 164*e*, wherein, in the fifth operation mode 164*e*, the first body 161 is coupled with a pipette interface or actuator interface 6 (e.g., described in relation to the gantry 170 below) and the magnetic distal region 163 of the first body 161 is coupled with the magnetic sleeve 1410 above the separation reservoir 129. In the fifth operation mode 164*d*, the pipette interface (or other actuatable component) delivers fluid from the pipetting head into the separation reservoir 129, and the magnetic sleeve 1410, still coupled with the first body 161 (and coupled to functionalized particles), is submerged within the fluid in the separation reservoir 129. In the fifth operation mode 164*e*, magnet 167*b* is displaced away from the separation reservoir 129 (e.g., by magnet actuator 169 described above).

Figure 12G:
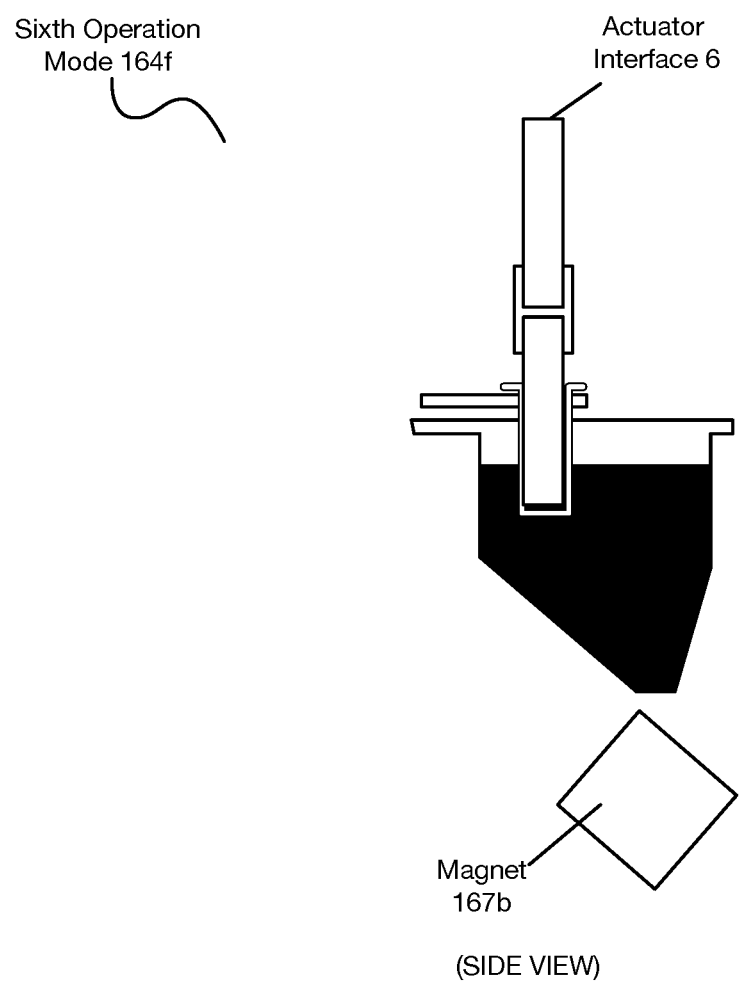

As shown in FIG. 12G, the separation subsystem 160 can provide a sixth operation mode 164*f*, wherein, in the sixth operation mode 164*f*, the first body 161 is coupled with a pipette interface or actuator interface 6 (e.g., described in relation to the gantry 170 below) and the magnetic distal region 163 of the first body 161 is coupled with the magnetic sleeve 1410 above the separation reservoir 129. In the sixth operation mode 164*f*, the pipette interface (or other actuatable component) moves the magnetic sleeve 1410, still coupled with the first body 161 back into a retained position at the sleeve stripping tool 165, and the magnetic sleeve 1410 (still coupled with functionalized particles) is submerged within the fluid in the separation reservoir 129. In the sixth operation mode 164*f*, magnet 167*b* is displaced away from the separation reservoir 129 (e.g., by magnet actuator 169 described above).

Figure 12H:
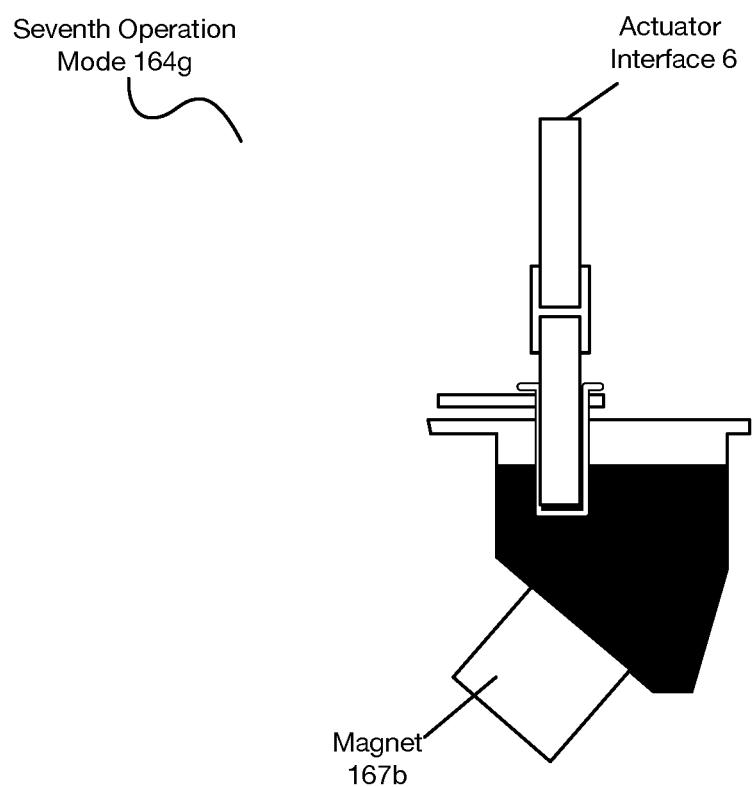

As shown in FIG. 12H, the separation subsystem 160 can provide a seventh operation mode 164*g*, wherein, in the seventh operation mode 164*g*, the first body 161 is coupled with a pipette interface or actuator interface 6 (e.g., described in relation to the gantry 170 below) and the magnetic distal region 163 of the first body 161 is coupled with the magnetic sleeve 1410 above the separation reservoir 129. In the seventh operation mode 164*g*, the magnetic sleeve 1410, still coupled with the first body 161 is in a retained position at the sleeve stripping tool 165, and the magnetic sleeve 1410 (with functionalized particles) is submerged within the fluid in the separation reservoir 129. In the seventh operation mode 164*g*, magnet 167*b* is displaced toward the separation reservoir 129 (e.g., by magnet actuator 169 described above) for to prepare for attraction and retention of target or non-target material coupled to the functionalized particles of the fluid against a wall 128*a* of the separation reservoir 129.

Figure 12I:
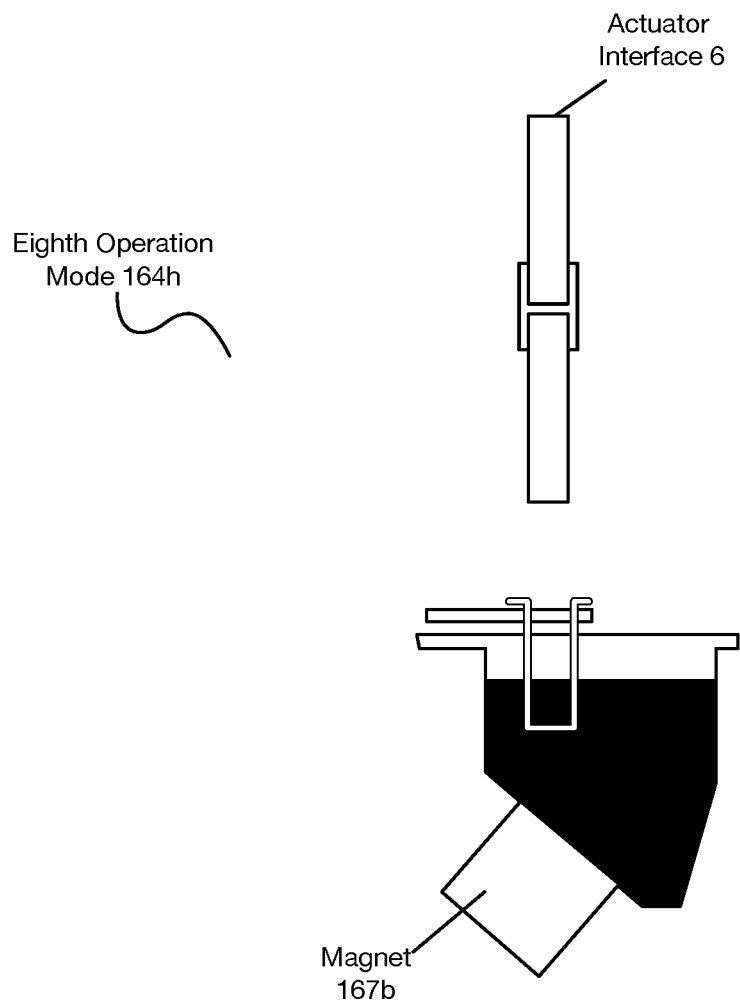

As shown in FIG. 12I, the separation subsystem 160 can provide an eighth operation mode 164*h*, wherein, in the eighth operation mode 164*h*, the first body 161 is coupled with a pipette interface or actuator interface 6 (e.g., described in relation to the gantry 170 below), and is being moved away from the separation reservoir 129 to be removed and replaced with a suitable tip from the tool container described above. In the eighth operation mode 164*h*, the magnetic distal region 163 of the first body 161 is uncoupled from the magnetic sleeve 1410 above the separation reservoir 129, by having the pipetting head move the first body 161 away from the magnetic sleeve 1410 while the magnetic sleeve 1410 is retained in position at the sleeve stripping tool 165. In the eighth operation mode 164*h*, the magnetic sleeve 1410 is submerged within the fluid in the separation reservoir 129. In the eighth operation mode 164*h*, magnet 167*b* is still positioned in proximity to the separation reservoir 129 (e.g., by magnet actuator 169 described above) for retention of target or non-target material coupled to functionalized particles of the fluid against a wall 128*a* of the separation reservoir 129. In the eighth operation mode 164*h*, the magnet 167*b* draws target material toward the bottom of the separation reservoir 129 (e.g., for later extraction from the bottom by the pipettor, for retention while the pipettor draws material unbound by the magnet 167*b*).

Figure 12J:
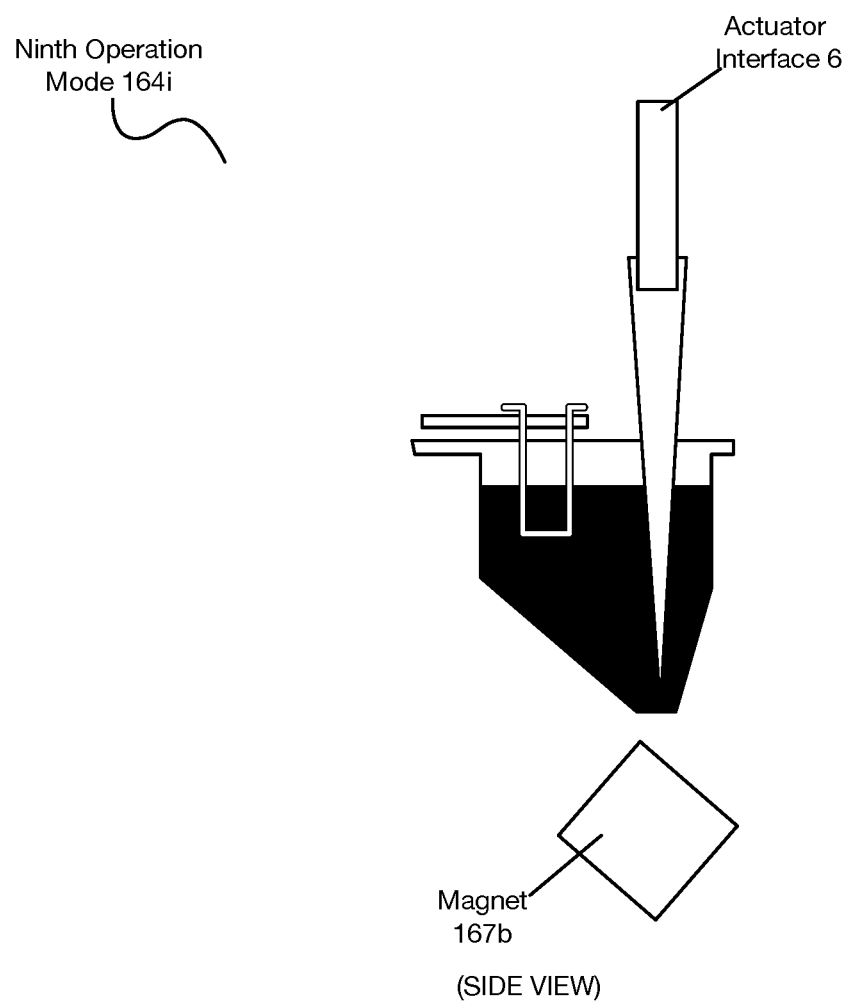
Figure 13A:
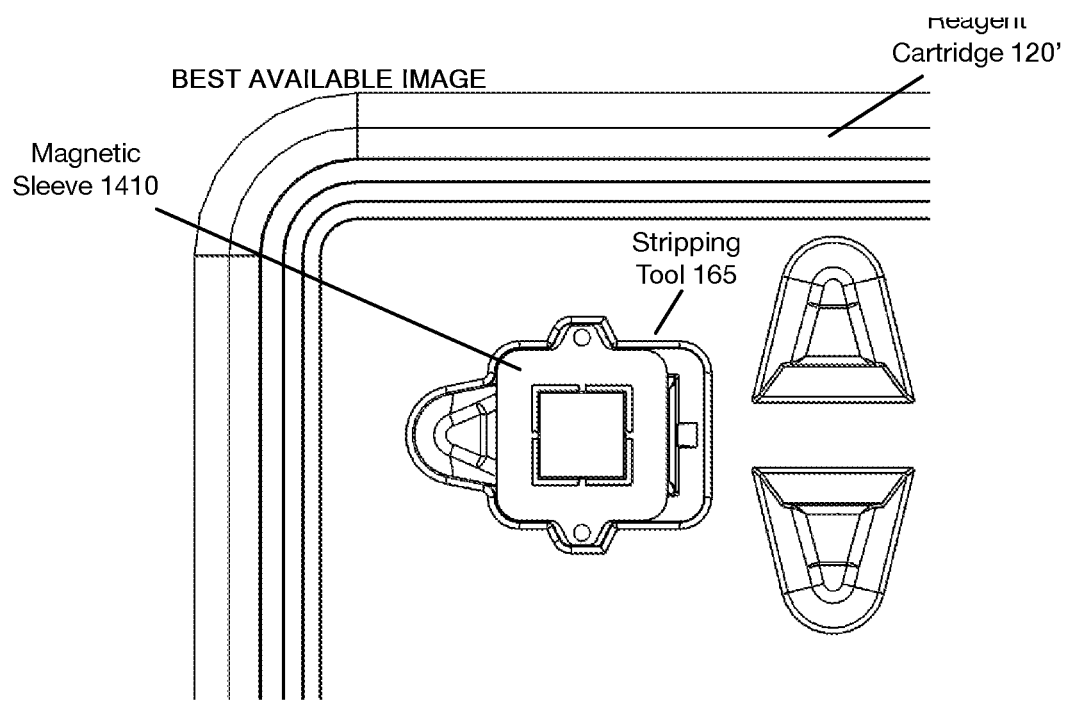
FIGS. 13A-13D depict views of components of a variation of a separation subsystem associated with a system for automated single cell sample processing.
Figure 13B:
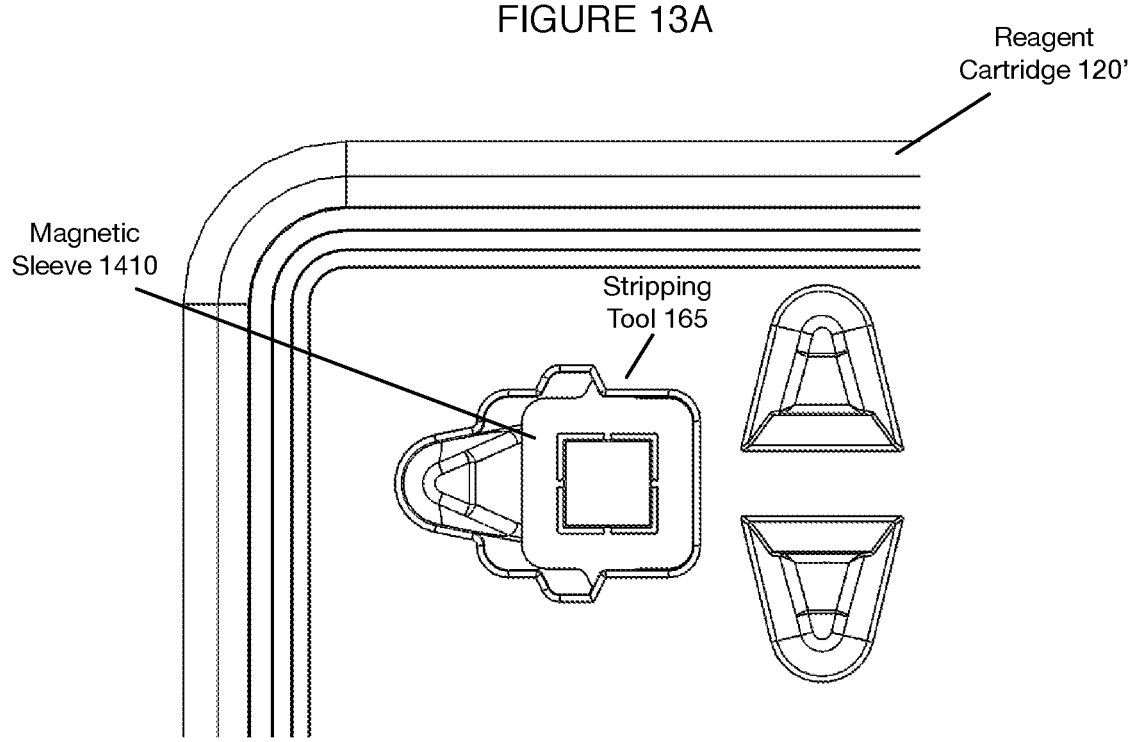
Figure 13C:
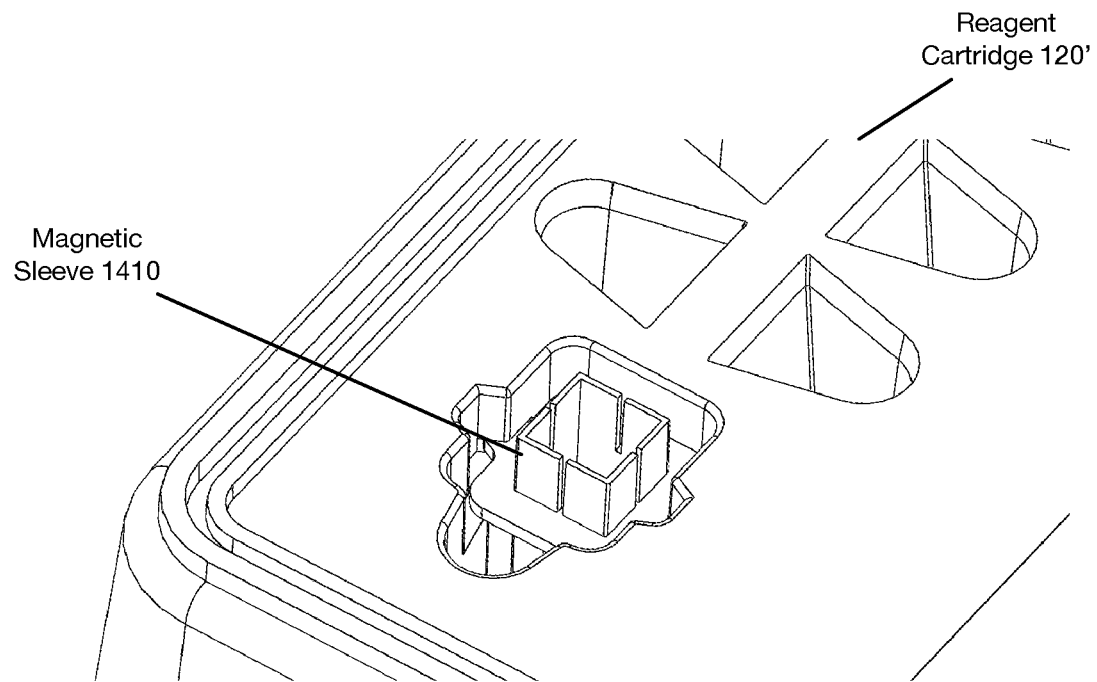
Figure 13D:
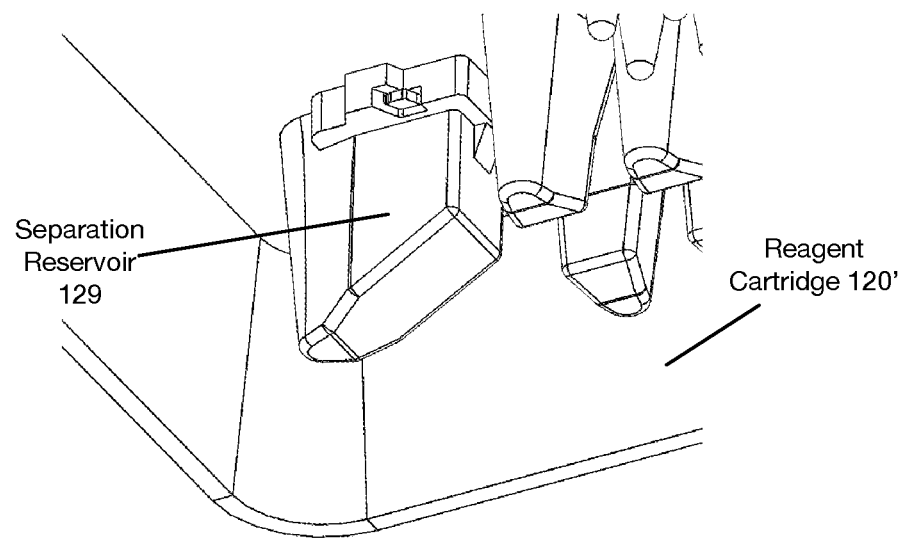

As shown in FIG. 12J, the separation subsystem 160 can provide a ninth operation mode 164*i*, wherein, in the ninth operation mode 164*i*, the pipetting head/actuator interface 6 is coupled with a suitable tip and moved into the separation reservoir 129 to aspirate material from the separation reservoir 129. In the ninth operation mode 164*i*, the magnetic sleeve 1410 is still retained in position above the separation reservoir 129 at the sleeve stripping tool 165 and submerged within the fluid in the separation reservoir 129. In the ninth operation mode 164*i*, magnet 167*b* is moved away from the separation reservoir 129 (e.g., by magnet actuator 169 described above) in coordination with aspiration of material by the pipetting head.

FIGS. 13A through 13D depict additional views of configurations of a magnetic sleeve 1410 with respect to sleeve stripping tool 165 of a separation reservoir 129 of a reagent cartridge 120, in relation to operation modes described above.

Variations of the separation subsystem 160 can, however, include elements and provide modes of operation for target material retrieval based upon one or more of: gravitational forces, buoyant forces, centrifugal forces, chemical separation, and/or any other suitable separation approaches. In yet another embodiment, target material retrieval operation by the separation subsystem 160 may be used to transfer target particles from the microwell chip to another substrate or another new empty microwell chip while keeping the relative spatial locations of the different particles being transferred.

2.2 System—Gantry

As shown in FIGS. 1A-1B, 2A, and 2C-2F, the system 100 can include a gantry 170 coupled to the deck no, which functions to support and/or enable actuation of one or more tools for various interactions with elements of the deck no, along a set of axes. In variations, the gantry 170 provides one or more rails/tracks for moving tools, such as pipettor 174 with pipette interface described below, in three dimensional space (e.g., a three dimensional volume bound by the first side of the deck). In variations, tools actuated using the gantry 170 can be moved relative to the sample processing cartridge 130, reagent cartridge 120, tool container 140, or other elements, for transfer of materials (e.g. cells, reagents, particles, etc.) across different components supported by the deck no. Additionally or alternatively, tools supported by the gantry 170 can be used for reading of barcodes associated with various disposables supported by the deck no (e.g., in relation to identifying proper setup of a run, in relation to inventory management, etc.). The gantry 170 preferably enables movement of one or more tools along one or more axes (e.g., X and Y axes shown in FIG. 2A) parallel to broad surfaces of the reagent cartridge 120, sample processing cartridge 130, and tool container 140, and additionally along an axis (e.g., Z axis shown in FIG. 2A) perpendicular to the broad surfaces. The gantry 170 can additionally or alternatively enable movement along a subset of these directions or along any other suitable direction. In order to enable movement, the gantry 170 includes or is otherwise coupled to one or more motors (e.g., motors for each axis or direction of movement), one or more encoders for position identification in each axis or direction of movement, and/or one or more switches (e.g., optical switches for each axis) for control of the gantry 170 (e.g., where the switches are electrically coupled with control circuity described in relation to the base 180 below).

In a first variation (e.g., as shown in FIGS. 2A-2B and 2D-2F), the gantry 170 includes a three dimensional track assembly (X-Y-Z track assembly) including an X-rail 171 for movement of tools along an X-axis, a Y rail 172 for movement of tools along a Y-axis, and a Z-rail 173 for movement of tools along a Z-axis. In the variation shown in FIG. 2A, the X-rail 171 is coupled with and slides along the Y-rail 172, and the Z-rail 173 is coupled with and slides along the X-rail 171; however, in other variations, the X-rail 171, Y-rail 172, and Z-rail 173 can be coupled and interact with each other in another suitable manner. In the variation shown in FIG. 2A, the gantry 170 is configured to move tools, using the X-rail 171 and the Y-rail 172, into alignment with elements of the deck no, and is configured to move tools, using the Z-rail 173 for accessing elements of the deck (e.g., portions of the reagent cartridge 120, elements of the sample processing cartridge 130, tools of the tool container 140, etc.). In some variations, the gantry 170 can be configured to return to a parked position (e.g., once a protocol is completed, when the system is turned off, before the lid is opened, etc.), where the parked position allows the user to access appropriate areas of the deck (e.g., for refilling tips, filling tubes with reagents, removing a microwell cartridge, etc.). However, the gantry 170 can have another suitable baseline position. Various operation modes of the gantry 170 are further described in relation to workflows of Section 3 below.

2.2.1 Gantry—Pipettor

As shown in FIG. 2A, the gantry 170 can include and/or or be configured to interact with a pipettor 174, which functions to hold, move, and/or otherwise interact with any number of tips or other tools, such as those of the tool container 140 described above. In variations, the pipettor 174 assembly can include one or more of: a pump (e.g., displacement pump) for providing pressure differentials for delivery and aspiration of fluids, a pressure sensor for sensing pipetting pressure, a level sensor for sensing fluid level within the pipettor 174, a tip detector (e.g., to enable determination of presence or absence of a tip coupled to the pipettor 174), and a tip ejection motor coupled to a tip ejector for removing tips from the pipettor 174. As shown in FIG. 2A, the pipettor 174 can be coupled to the Z-rail 173 of the gantry 170; however, in other variations, the pipettor 174 can additionally or alternatively be coupled to other portions of the gantry 170.

The pipettor 174 is preferably operable in an automated fashion (e.g., motorized, mechanized, self-operating, etc.) and can be configured to control any or all of the following predetermined parameters: volume (e.g. dispensing exact volumes, aspirating exact volumes), a height above the well at which each material is dispensed (e.g. priming buffer is dispensed between 0.25 and 0.3 millimeters above the top of each well, cell suspension is dispensed at a height of 0.25 millimeters above the top of each well, etc.), or can control any other suitable property according to any suitable parameter. Additionally or alternatively, the pipettor 174 can be configured to operate in a manual fashion (e.g., according to a user, with user intervention, held and used by a user, etc.) or in any suitable way. In yet another embodiment, the pipettor 174 may be used to pick up one or more tools associated with the tool container, such as any or all of: a mechanical tool, magnetic tool, an optical tool, and any other suitable tool. The tools can be moved by the pipettor 174 to the reagent cartridge and/or the microwell cartridge such that the tool(s) can perform specific mechanical/magnetic and/or optical functions with respect to specific contents of the reagent cartridge or microwell cartridge.

2.2.2 Gantry—Other Tools

Additionally, the gantry 170 can include or support one or more tools described in relation to other elements above. For instance, the gantry 170 can be coupled with a unit of lid-opening tool 145 (shown in FIG. 2B) for transitioning the lid 135 of the sample processing cartridge 130 between open and closed states. The gantry 170 can additionally or alternatively be coupled with a magnetic head actuator 175 (shown in FIG. 2B) associated with the separation subsystem 160 described above (e.g., in relation to actuation of the first body 161 with magnetic distal region 163) for separation of target material from non-target material.

In some variations, the gantry 170 can directly or indirectly be coupled with a camera 176 (e.g., camera coupled with a light), which functions to enable reading of tags (e.g., barcodes) associated with various disposables supported by the deck 110 (e.g., in relation to identifying proper setup of a run, in relation to inventory management, etc.). Additionally or alternatively, the camera 176 can include functionality for transmitting image data capturing configurations of elements at the deck no without reading of specific tags. As shown in FIGS. 2A and 2F, the camera 176 can be coupled to the Z-rail 173 with pipettor 174 described above, such that the camera 176 has a field of view associated with objects that the pipettor 174 is aligned with. However, motion of the camera 176 can alternatively be uncoupled from the pipettor 174, such that the camera 176 can be moved independently of the pipettor 174. In variations, the camera 176 can include components described in applications incorporated by reference above. The camera image can also be used as an additional feedback mechanism for the precise movement of the gantry 170 and/or its components (e.g., pipettor, tools, etc.) to reach a desired location, thereby dramatically improving the accuracy and precision of the motion system (e.g., to less than 100 microns, less than 50 microns, less than 25 microns, less than 10 microns, less than 5 microns, less than 1 micron, etc.).

Additionally or alternatively, as shown in FIGS. 1A and 1B, the gantry 170 can include various sensors for monitoring environmental or other parameters of the system 100. For instance, in variations, the sensors can include one or more of: temperature sensors, humidity sensors, pressure sensors, optical sensors, vibration sensors, and other suitable sensors. The sensors can, however, be positioned relative to the system 100 in another suitable manner (e.g., uncoupled from the gantry 170, positioned at the deck 110, positioned at the base 180, etc.).

2.3 System—Base

As shown in FIG. 1A, the system 100 can include a base 180, which functions to support control and processing architecture associated with elements of the deck 110 and gantry 170 described above. In variations, the base 180 can support control and processing architecture for one or more system functions including: pressure modification for fluid delivery throughout the sample processing cartridge 130 and/or pipettor 174; fluid level sensing (e.g., at the sample processing cartridge 130, at the pipettor 174, at various storage volumes of the reagent cartridge 120, etc.); actuation of lid opening mechanisms of the sample processing cartridge 130; thermocycling and/or other heating functions for the reagent cartridge 120 and/or sample processing cartridge 130; cooling functions for the reagent cartridge 120 and/or sample processing cartridge 130; separation functions (e.g., elution, magnetic separation, other separation, etc.); functions for control of the gantry 170; functions involving receiving sensor signals and returning outputs; functions involving receiving sensor signals and executing various actions; functions for transitioning system doors between various states (e.g., open states, closed states, locked states, unlocked states, etc.); functions associated with system power management; functions associated with system status indication elements (e.g., lights, audio output devices, visual output devices, etc.); functions associated with system input devices (e.g., buttons, keyboards, keypads, mice, joysticks, switches, touch screens, etc.); functions associated with display devices; functions associated with system data storage devices; functions associated with system transmission devices (e.g., wired transmission devices, wireless transmission devices, etc.); and other suitable functions.

In variations, the base 180 can thus support an electronics subsystem (e.g. PCB, power source, communication module, encoder, etc.) associated with a processing architecture (e.g. onboardthe system, separate from the system, etc.), or any other suitable component, where the processing architecture can include any or all of: processors (e.g. microprocessors), controllers (e.g. microcontrollers), memory, storage, software, firmware, or any other suitable component. Additionally, the processing subsystem can include a machine vision module, which functions to read tags, verify protocols, perform error detection (e.g. detect that reagents do not match an assigned protocol), or perform any other function.

For instance, in an example operation flow, an operator can initiate the performance of the protocol (e.g., by pushing a button of the system, by interacting a touch-sensitive display of the system to make a selection, etc.). A barcode reader performs an error detection protocol by scanning tags of the deck elements (e.g, reagent cartridge, sample processing cartridge, tool container, etc.) and comparing with the protocol selected by the user; if the tags do not match the selected protocol, a notification can be transmitted to the user, and if the tags are correct, the protocol can begin. At this point, the operator may no longer needed. According to one or more workflows, some of which are described in Section 3 below, the correct types and volumes of materials (e.g., reagents/samples) are added to or removed from the sample processing cartridge at the correct times in an automated fashion. Once the protocol is complete, the operator can proceed with collecting and/or processing the contents of the microwell cartridge as desired, and/or setting up a new run. Variations of methods and workflows enabled by the system 100 are further described below.

Embodiments, variations, and examples of control and processing architecture are further described in U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; U.S. application Ser. No. 15/815,532, filed 16 Nov. 2017; U.S. application Ser. No. 16/115,370, filed 28 Aug. 2018, U.S. application Ser. No. 16/564,375, filed 9 Sep. 2019, and U.S. application Ser. No. 16/816,817, filed 12 Mar. 2020, as incorporated by reference above.

2.4 System—Functional Coupling Between Deck, Gantry, and Base

Figure 14A:
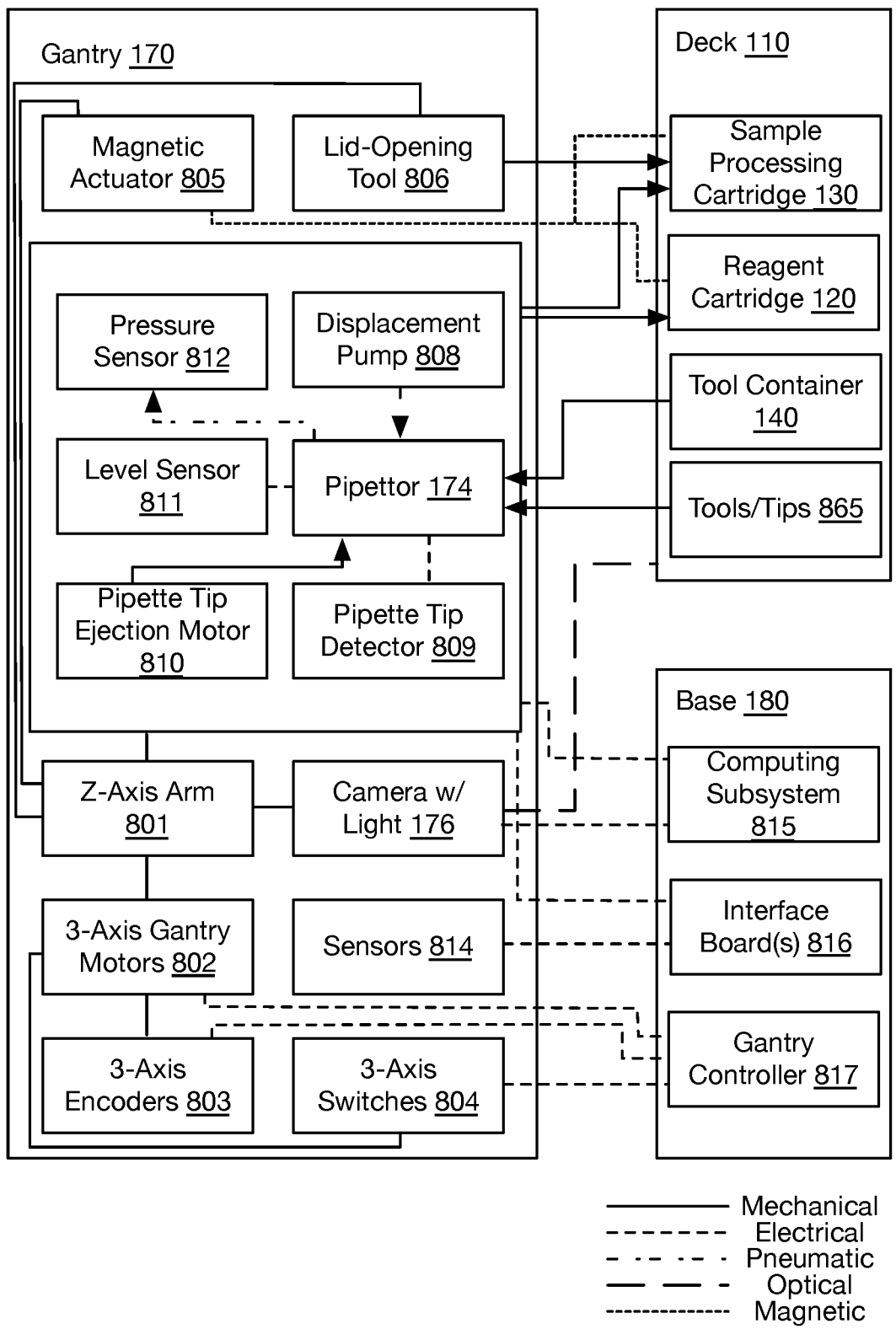
FIGS. 14A-14C depict embodiments of functional coupling between components of a system for automated single cell sample processing.
Figure 14B:
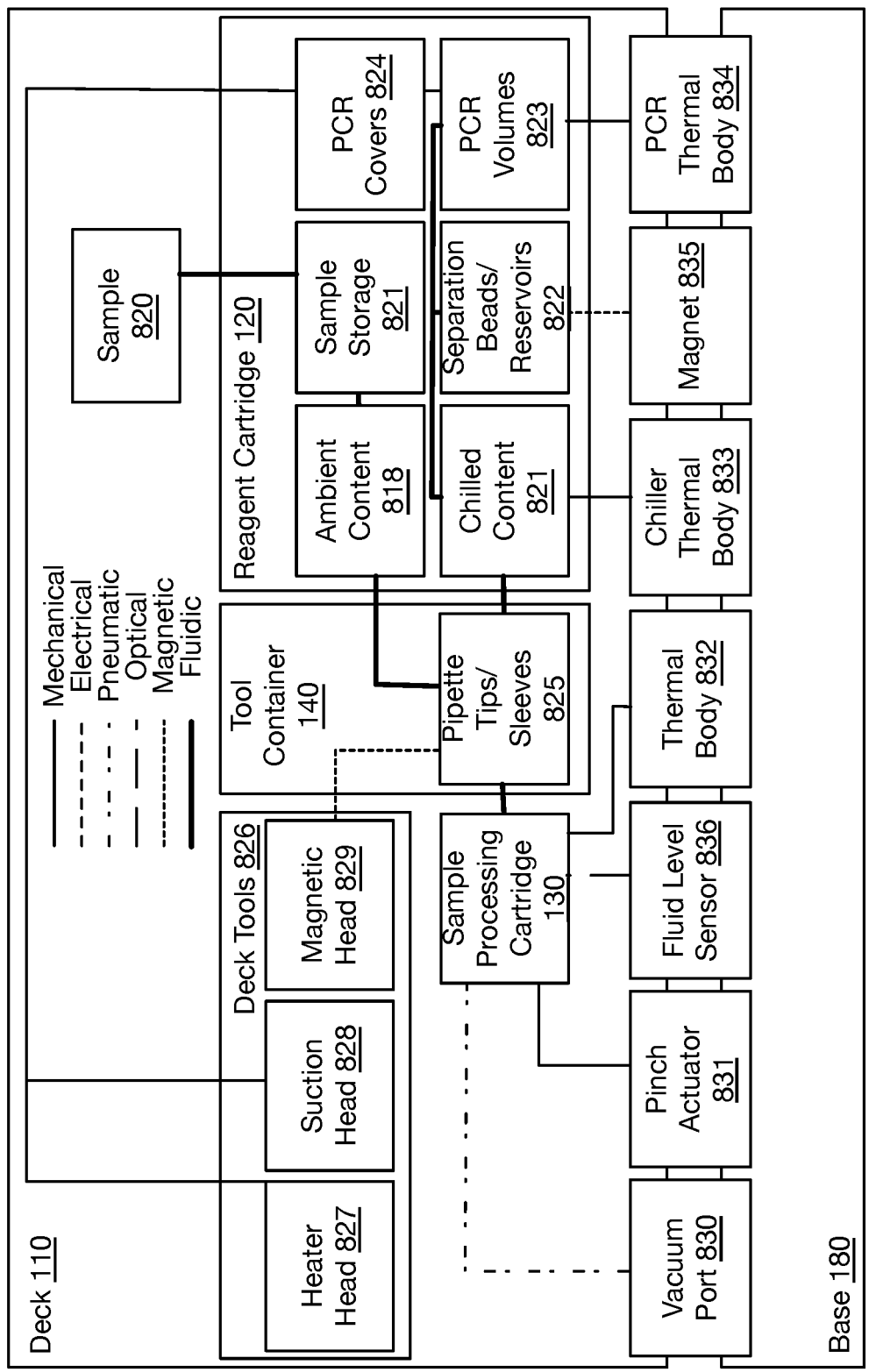
Figure 14C:
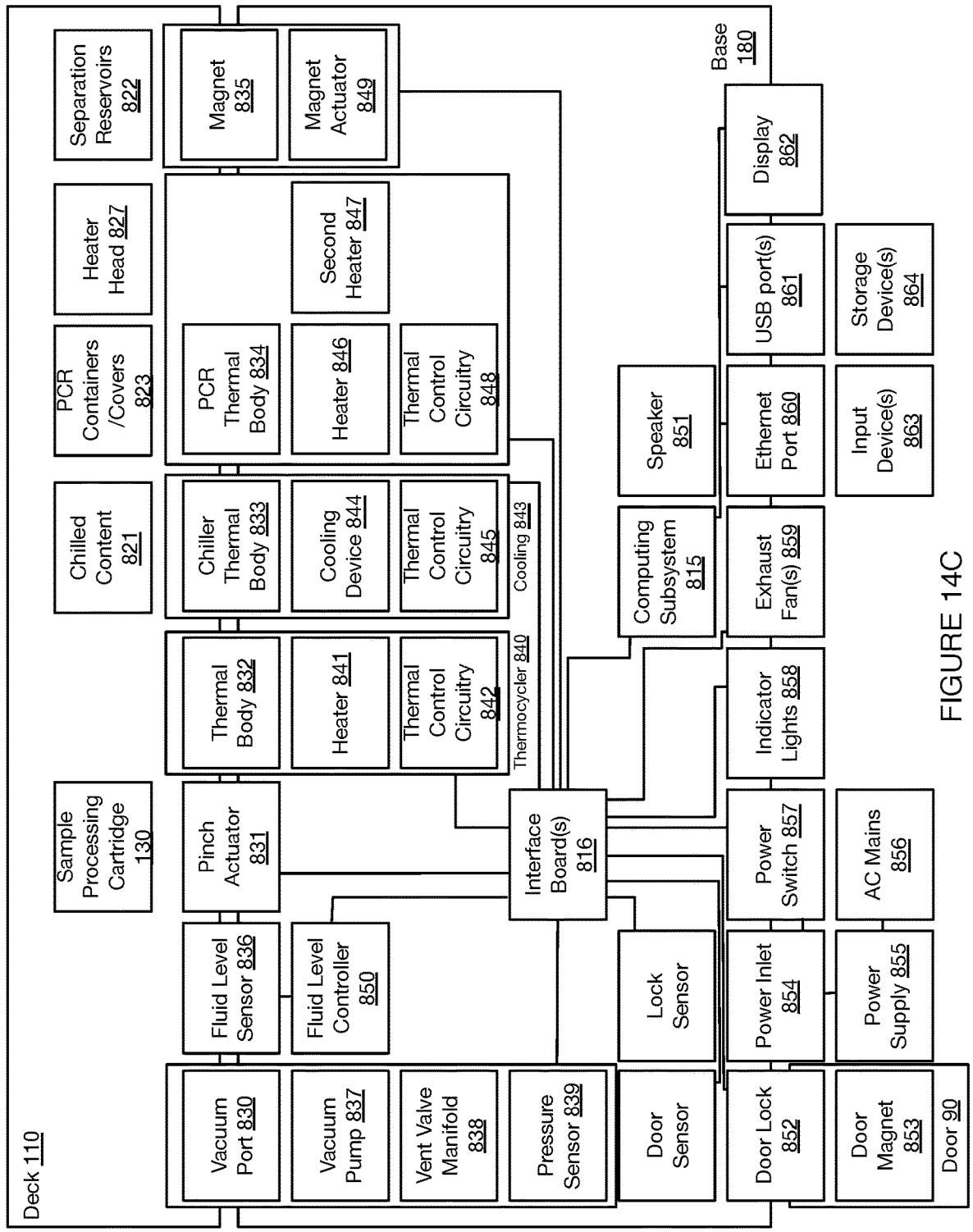

In variations, the deck 110, gantry 170, and base 180 of the system can be functionally coupled to provide various functions. Functional coupling can be electromechanical, mechanical, electrical, magnetic, pneumatic, fluidic, optical, and/or of other coupling means, according to various modes of operation. FIGS. 14A-14C depict functional coupling for a variation of a system, as described below.

FIG. 14A depicts an example of mechanical, electrical, pneumatic, optical, and magnetic communication between various elements of the deck 110, gantry 170, and base 180. In more detail, as shown in FIG. 14A, the gantry 170 supports actuation-associated elements including a Z-axis arm 801 associated with Z-rail 173 described above, 3-axis gantry motors 802, 3-axis encoders 803, 3-axis optical switches 804, a magnetic actuator 805, and a lid-opening tool 806. The gantry 170 further supports pipetting elements including: a pipettor 174, a displacement pump 808, a pipette tip detector 809, a pipette tip ejection motor 810, a level sensor 811, and a pressure sensor 812. The gantry 170 also supports a camera and light 176 and a set of sensors 814 including temperature and humidity sensors. As shown in FIG. 14A, the deck 110 supports a sample processing cartridge 130, a reagent cartridge 120, and a tool container 140 including a set of tools 865. As shown in FIG. 14A, the base 180 supports a first computing subsystem 815, one or more interface boards 816, and gantry-control circuitry 817. Mechanical, electrical, pneumatic, optical, and magnetic communication between various elements of the deck 110, gantry 170, and base 180 are depicted with various line types in FIG. 14A.

FIG. 14B depicts an example of mechanical, fluidic, magnetic, and pneumatic communication between various elements of the deck 110 and base 180. In more detail, as shown in FIG. 14B, the deck 110 supports a reagent cartridge 120 including: a storage volume for ambient reagents and functional beads 818, a sample storage volume 819 for receiving a raw sample 820, a storage volume for storing chilled reagents and/or results of sample processing 821, a set of storage volumes for separation particles and associated separation reservoirs 822, and a set of storage volumes for PCR 823, with associated PCR covers 824; a tool container 140 including a set of tools (e.g., pipette tips) 825; a sample processing cartridge 130; and a set of deck tools 826 including a heater head 827, a suction head 828, and a magnetic head 829. As shown in FIG. 14B, a set of elements interface the deck 110 with the base 180, where the set of elements can include one or more of: a vacuum port 830, a pinch actuator 831, a sample processing cartridge thermal body 832 (configured to mate with the microwell region of the sample processing cartridge 130 or other region of the sample processing cartridge 130), a first reagent cartridge thermal body 833 (configured to mate with a domain of the reagent cartridge 120, at the first region in, for chilled reagents), a second reagent cartridge thermal body 834 (configured to mate with a domain of the reagent cartridge 120, at the first region in, for PCR thermocycling), a fluid level sensor 836, and a magnet 835 for separation processes. Mechanical, fluidic, magnetic, and pneumatic communication between various elements of the deck 110 and base 180 are depicted with various line types in FIG. 14B.

FIG. 14C depicts an example of electrical communication between various elements of the deck 110 and base 180. In more detail, as shown in FIG. 14C, the deck 110 supports a sample processing cartridge 130; a reagent cartridge 120 including: a storage volume for storing chilled reagents and/or results of sample processing 821, a set of storage volumes for separation particles and associated separation reservoirs 822, and a set of storage volumes for PCR 823 with associated PCR covers; and a set of deck tools 826 including a heater head 827. As shown in FIG. 14C, a set of elements interface the deck 110 with the base 180, where the set of elements can include one or more of: a vacuum port 830, a pinch actuator 831, a sample processing cartridge thermal body 832, a first reagent cartridge thermal body 833, a second reagent cartridge thermal body 834, a magnet 835 for separation processes, and a fluid level sensor 836.

In more detail, the vacuum port 830 is coupled to a pumping subsystem 837 which includes a vent valve manifold 838, and a pressure sensor 839. The sample processing cartridge thermal body 832 is coupled to a thermocycler 840 of a heating and cooling subsystem, which includes a heater 841 (e.g., Peltier heater, thermocouples, heat sinks, and fans) and thermal control circuitry 842. The first reagent cartridge thermal body 833 is coupled to a cooling device 843 of a heating and cooling subsystem, which includes a cooling element 844 (e.g., Peltier cooler, thermocouples, heat sinks, and fans) and thermal control circuitry 845. The second reagent cartridge thermal body 834 is coupled to a heating device (e.g., for on-boardPCR) of a heating and cooling subsystem, which includes a first heater 846 (e.g., Peltier heater, thermocouples, heat sinks, and fans), a second heater 847 coupled to the heat sink, and thermal control circuitry 848. The magnet 835 is coupled to a magnet actuator 849. Finally, the fluid level sensor 836 is coupled to a fluid level controller 850.

As shown in FIG. 14C, the base 180 further supports a first computing subsystem 815, one or more interface boards 816, a speaker 851, a door locking element 852 (interfacing with a door magnet 853 to provide operation modes of a door 90, as described above), a power inlet 854 coupled to a power supply 855 coupled to AC mains 856, a power switch 857, indicator lights 858 (e.g., for power/ground effects), exhaust fans 859, a set of ports (e.g., including an ethernet port 860 and USB ports 861), and a display 862 (e.g., touchscreen display). Elements of the base can further interface with off-system accessories (e.g., input devices 863, storage devices 864). Electrical, communication between various elements of the deck 110 and base 180 are depicted with various line types in FIG. 14C.

3. Method

Figure 15:
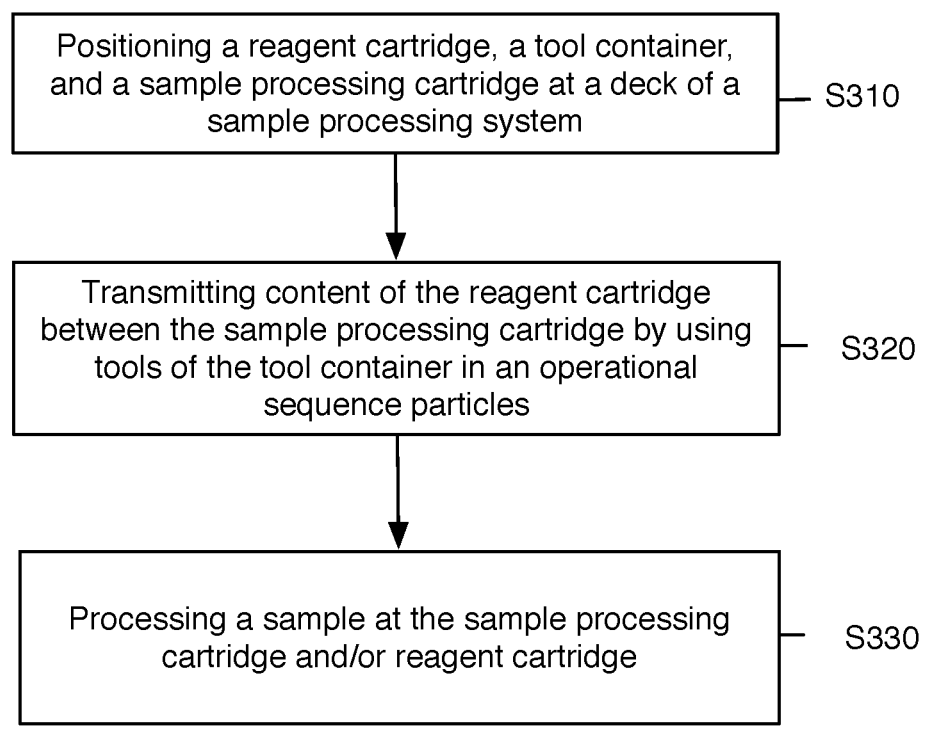
FIG. 15 depicts a flow chart of an embodiment of a method for automated single cell sample processing.

As shown in FIG. 15, an embodiment of a method 300 for sample processing includes: positioning a reagent cartridge, a tool container, and a sample processing cartridge at a deck of a sample processing system S310; transmitting content of the reagent cartridge between the sample processing cartridge by using tools of the tool container in an operational sequence S320; and processing a sample at the sample processing cartridge and/or reagent cartridge S330. Additionally or alternatively, the method 300 can include any or all of the processes described in U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; U.S. application Ser. No. 15/815,532, filed 16 Nov. 2017; U.S. application Ser. No. 16/115,370, filed 28 Aug. 2018, U.S. application Ser. No. 16/564,375, filed 9 Sep. 2019, and U.S. application Ser. No. 16/816,817, filed 12 Mar. 2020, which are each incorporated in their entirety by this reference.

The method is preferably performed with an embodiment, variation, or example of the systems described above (e.g., in relation to transmission of content between various elements and/or sample processing), but can additionally or alternatively be performed with any other suitable system. The method is further preferably at least partially automated (e.g., requires user to load reagents and select a protocol, requires no user intervention, etc.), but one or more portions can additionally or alternatively be manually performed (e.g., for quality control steps, for all protocols, for rare protocols, etc.).

Specific workflows associated with the method 300 and system elements described above are described in further detail below, where samples (e.g., samples including cell-derived material, proteins, mRNAs, proteins and mRNA; samples that include multiple samples each tagged with multiplexing barcodes; samples that include encapsulated particles from either cell or non-cell derived biomarkers, etc.) can be processed according to the workflows (e.g., workflows in Sections 3.1-3.3 below), followed by library preparation workflows (e.g., workflow in Section 3.4 below), followed by next generation sequencing (NGS).

Figure 16:
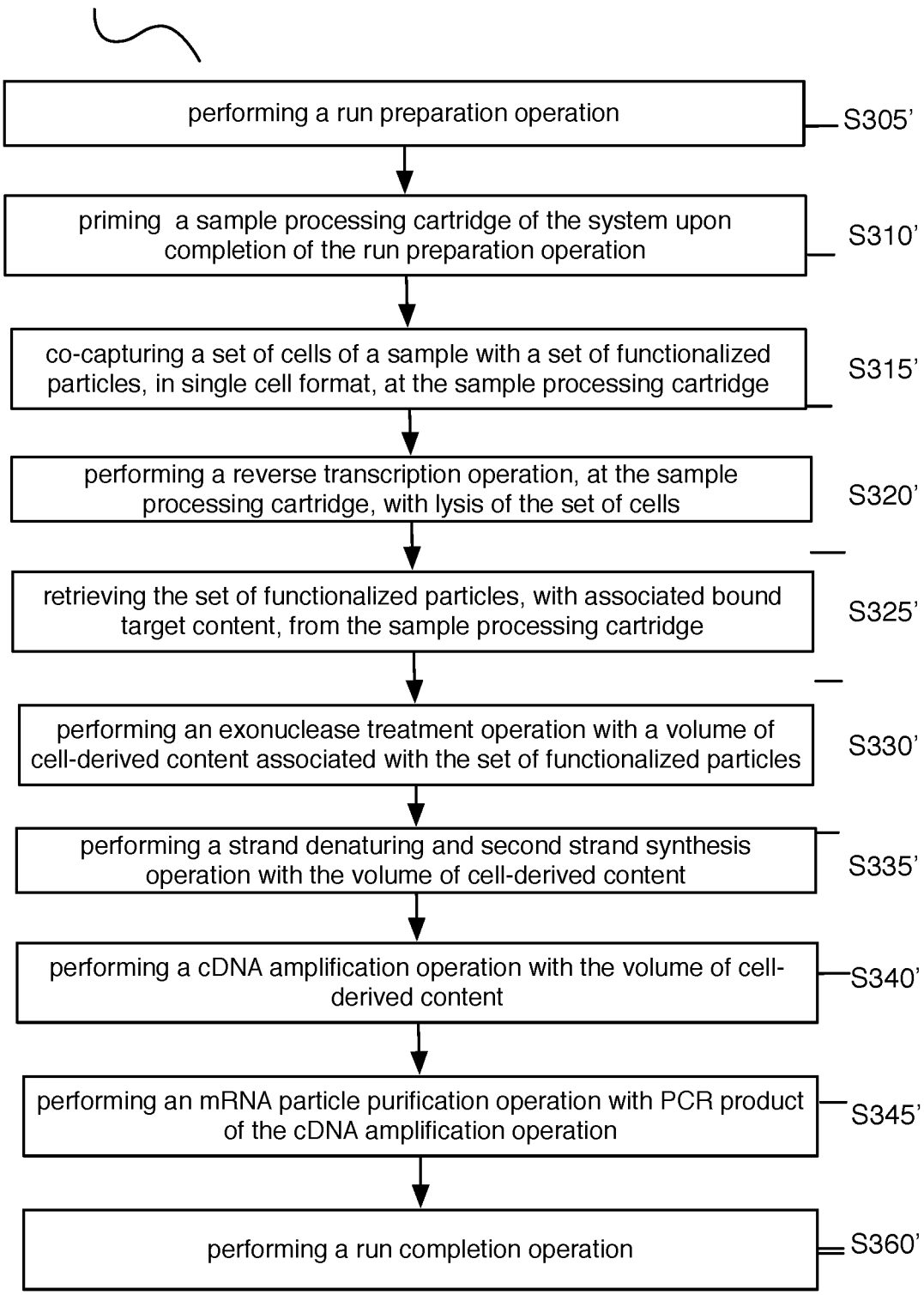
FIG. 16 depicts a first variation of a method for automated single cell sample processing.

3.1 Method—Example Workflow for a 3' Protocol for mRNA Synthesis/cDNA Amplification As shown in FIG. 16, a variation of the method, configured for mRNA synthesis/cDNA amplification 300' can include: performing a run preparation operation, wherein the run preparation operation configures a system for performing an mRNA synthesis/cDNA amplification protocol S305'; priming a sample processing cartridge of the system upon completion of the run preparation operation S310'; co-capturing a set of cells of a sample with a set of functionalized particles, in single cell format, at the sample processing cartridge S315'; lysing the set of cells followed by binding released mRNA from the lysed cells with the functionalized particles (e.g., barcoded microspheres) (e.g., with associated washing the functionalized particles of any unbound mRNA) S320'; performing a reverse transcription operation; retrieving the set of functionalized particles, with associated bound target content, from the sample processing cartridge S325'; performing an exonuclease treatment operation with a volume of cell-derived content associated with the set of functionalized particles S330'; performing a strand denaturing and second strand synthesis operation with the volume of cell-derived content S335'; performing a cDNA amplification operation with the volume of cell-derived content S340'; performing an mRNA particle purification operation with PCR product of the cDNA amplification operation S345'; and performing a run completion operation upon completion of the mRNA particle purification operation S360'.

In more detail, performing a run preparation operation, S305' can include sub-steps associated with one or more of: preparing a cell suspension; initializing and performing operational checks of system subsystems (e.g., associated with the deck, associated with the gantry, associated with the base, etc.); returning the gantry to a home position; removing one or more seals from the reagent cartridge and/or loading reagents onto the reagent cartridge; positioning a sample processing cartridge unit; removing one or more seals from the tool container positioned at the deck; dispensing the cell suspension into a storage container prior to use; verifying proper positioning and states (e.g., in relation to expiration dates) of disposables for the protocol, upon scanning tags of disposables with a camera (e.g., machine vision camera); receiving sample identification information (e.g., from an operator); and initiating run of the sample. Steps of S305" can be implemented by the system automatically and/or by an operator. Furthermore, various sub-steps can be performed once, or repeated as recommended.

In more detail, priming a sample processing cartridge of the system upon completion of the run preparation operation S310' and co-capturing a set of cells of a sample with a set of functionalized particles, in single cell format, at the sample processing cartridge S315' can include one or more of: dispensing a priming solution (e.g., in a manner that prevents bubbles from being trapped within the sample processing cartridge) into the inlet reservoir of a sample processing cartridge; incubating the priming solution within the sample processing cartridge; dispensing one or more wash solutions into the inlet reservoir of the sample processing cartridge; transmitting solutions to a waste containment region of the sample processing cartridge; dispensing a cell suspension into the inlet reservoir of the sample processing cartridge and capturing cells, in single-cell format, within wells of the sample processing cartridge; dispensing a set of functionalized particles into the inlet reservoir of the sample processing cartridge and co-capturing the set of functionalized particles with the set of cells; incubating content of the wells of the sample processing cartridge; and picking up/releasing various tools (e.g., by a gantry coupled to a pipette interface) involved with the substep(s). Steps S310' and S315' are preferably performed automatically by the system but can alternatively be performed in another suitable manner. Furthermore, various sub-steps can be performed once, or repeated as recommended.

In more detail, performing a reverse transcription operation, at the sample processing cartridge, with lysate of the set of cells S320' in the presence of functionalized particles (e.g., barcoded microspheres) can include one or more of: dispensing one or more wash solutions into the inlet reservoir of the sample processing cartridge; transmitting solutions to a waste containment region of the sample processing cartridge; dispensing a particle-binding buffer into the inlet reservoir of the sample processing cartridge; dispensing a DTT solution into the inlet reservoir of the sample processing cartridge; dispensing a lysis solution into the inlet reservoir of the sample processing cartridge; displacing fluid above wells of the sample processing cartridge with an oil, thereby isolating contents of wells and preventing undesired material transfer across wells (e.g., as in U.S. application Ser. No. 16/564,375 filed 9 Sep. 2019, which is herein incorporated in its entirety by this reference); displacing the oil with air from the inlet reservoir; dispensing a particle-binding wash buffer into the inlet reservoir of the sample processing cartridge; dispensing a pre-RT reaction wash buffer into the inlet reservoir of the sample processing cartridge; dispensing a cDNA synthesis solution (e.g., SuperScript IV™) into the inlet reservoir of the sample processing cartridge; dispensing an RT cocktail into the inlet reservoir of the sample processing cartridge; incubating contents of the sample processing cartridge; performing incubation steps; and picking up/releasing various tools involved with the substep(s). Step S320' is preferably performed automatically by the system but can alternatively be performed in another suitable manner. Furthermore, various sub-steps can be performed once, or repeated as recommended.

In more detail, retrieving the set of functionalized particles, with associated bound target content, from the sample processing cartridge S325' can include performing magnetic separation operations (e.g., as described above), using manual or automatic operations. Furthermore, various sub-steps can be performed once, or repeated as recommended.

In more detail, performing an exonuclease treatment operation with a volume of cell-derived content associated with the set of functionalized particles S330' can include one or more of: mixing water and exonuclease buffer to produce an exonuclease solution having a desired concentration; dispensing the exonuclease solution, with functionalized particles into a first PCR container; dispensing an oil (e.g., mineral oil) into the first PCR container; thermocycling and incubating contents of the first PCR container; extracting a product of the first PCR container; performing a separation operation with the product of the first PCR container; discarding waste from the separation operation; performing incubation steps; and picking up/releasing various tools involved with the substep(s). Step S330' is preferably performed automatically by the system but can alternatively be performed in another suitable manner. Furthermore, various sub-steps can be performed once, or repeated as recommended.

In more detail, performing a strand denaturing and second strand synthesis operation S335' can include one or more of: transferring a hydroxide solution (e.g., sodium hydroxide solution) to a second magnetic separation container; mixing contents of the second magnetic separation container; activating a magnetic separation subsystem (e.g., set of magnets coupled to actuator, described above) in proximity to the second magnetic separation container, thereby separating functionalized magnetic particles toward the magnet(s); discarding waste material from the second magnetic separation container; dispensing a wash solution to the second magnetic separation container; mixing a second strand synthesis primer enzyme within a process container in proximity to the second magnetic separation container; mixing the second strand synthesis primer enzyme with contents of the second magnetic separation container; dispensing product of the second magnetic separation container into a second PCR container; thermocycling contents of the second PCR container, with mixing; transferring product of the second PCR container to a third magnetic separation container; magnetically separating product of the third magnetic separation container from waste and discarding waste; transferring a wash solution to the third magnetic separation container; and picking up/releasing various tools involved with the substep(s). Step S335' is preferably performed automatically by the system but can alternatively be performed in another suitable manner. Furthermore, various sub-steps can be performed once, or repeated as recommended.

In more detail, performing a cDNA synthesis operation S340' can include one or more of: mixing a polymerase blend (e.g., Kapa Biosystems HiFi Hotstart Ready Mix™) within a cold storage volume; mixing the PCR master mix from the cold storage volume with contents of the third magnetic separation container; aliquoting contents of the third magnetic separation container into a third, fourth, fifth, and sixth PCR operation containers; aliquoting an oil (e.g., mineral oil) into the third, fourth, fifth, and sixth PCR operation containers; running a third PCR operation; and picking up/releasing various tools involved with the substep(s). Step S340' is preferably performed automatically by the system but can alternatively be performed in another suitable manner. Furthermore, various sub-steps can be performed once, or repeated as recommended.

In more detail, performing an mRNA particle purification operation with PCR product of the cDNA amplification operation S345' can include one or more of: dispensing product from the third, fourth, fifth, and sixth PCR operation containers into a fourth magnetic separation container; mixing and transferring PCR purification particles (e.g., AMPure beads XP™) into the fourth magnetic separation container; diluting and mixing ethanol with nuclease-free water within a tenth magnetic separation container; removing waste from the tenth magnetic separation container, after incubation; mixing nuclease-free water with target content of the tenth magnetic separation container; magnetically separating target mRNA-cDNA product from tenth magnetic separation container; transferring target mRNA-cDNA product from tenth magnetic separation container to cold storage; and picking up/releasing various tools involved with the substep(s). Step S345' is preferably performed automatically by the system but can alternatively be performed in another suitable manner. Furthermore, various sub-steps can be performed once, or repeated as recommended.

In more detail, performing a run completion operation upon completion of the mRNA particle purification operation S360' can include one or more of: returning the gantry to a home configuration; providing a notification that sample processing is complete; releasing the reagent cartridge and/or sample processing cartridge from the system for off-boardstorage; discarding system waste; performing a system cleaning operation; and transitioning the system to a deactivated (e.g., idle, off) state. Steps of S360' can be implemented by the system automatically and/or by an operator. Furthermore, various sub-steps can be performed once, or repeated as recommended.

Example details of steps of the method 300' are further described in TABLE 1 of Appendix A. In relation to steps of the method 300', descriptions of ambient temperature and chilled reagents, as well as positions associated with storage volumes of an embodiment of the reagent cartridge described above are described in TABLE 2 of Appendix A. In relation to TABLE 2 of Appendix A, volumes of reagents can be scaled according to sizes of sample processing chips used and/or number of reactions run. In relation to magnetic separation operations, descriptions of apparatus and associated reagents used, as well as positions associated with storage volumes of an embodiment of the reagent cartridge described above are described in TABLE 3 of Appendix A. In relation to amplification (e.g., PCR) operations, descriptions of apparatus and associated reagents used, as well as positions associated with storage volumes of an embodiment of the reagent cartridge described above are described in TABLE 4 of Appendix A. In relation to fluid aspiration and delivery operations, descriptions of apparatus, as well as positions associated with an embodiment of the tool container described above are described in TABLE 5 of Appendix A. In relation to actuation of components for automation of protocol aspects, gantry arm and pipettor operations (e.g., in relation to apparatus coupling with disposables, apparatus uncoupling from disposables, fluid mixing, waste discarding, aspiration, delivery, aliquoting, etc.) are described in TABLE 6 of Appendix A. In relation to transitioning between modes for automation of protocol aspects, sample processing cartridge operations are described in TABLE 7 of Appendix A. In relation to transitioning between modes for automation of protocol aspects, heating and cooling subsystem operation modes are described in TABLE 8 of Appendix A. In relation to transitioning between modes for automation of protocol aspects, magnetic separation subsystem operations are described in TABLE 9 of Appendix A. In relation to amplification operations, PCR program details associated with the method 300' are described in TABLE 10 of Appendix A.

3.2 Method—Example Workflow for Single Cell Cytometry

Figure 17:
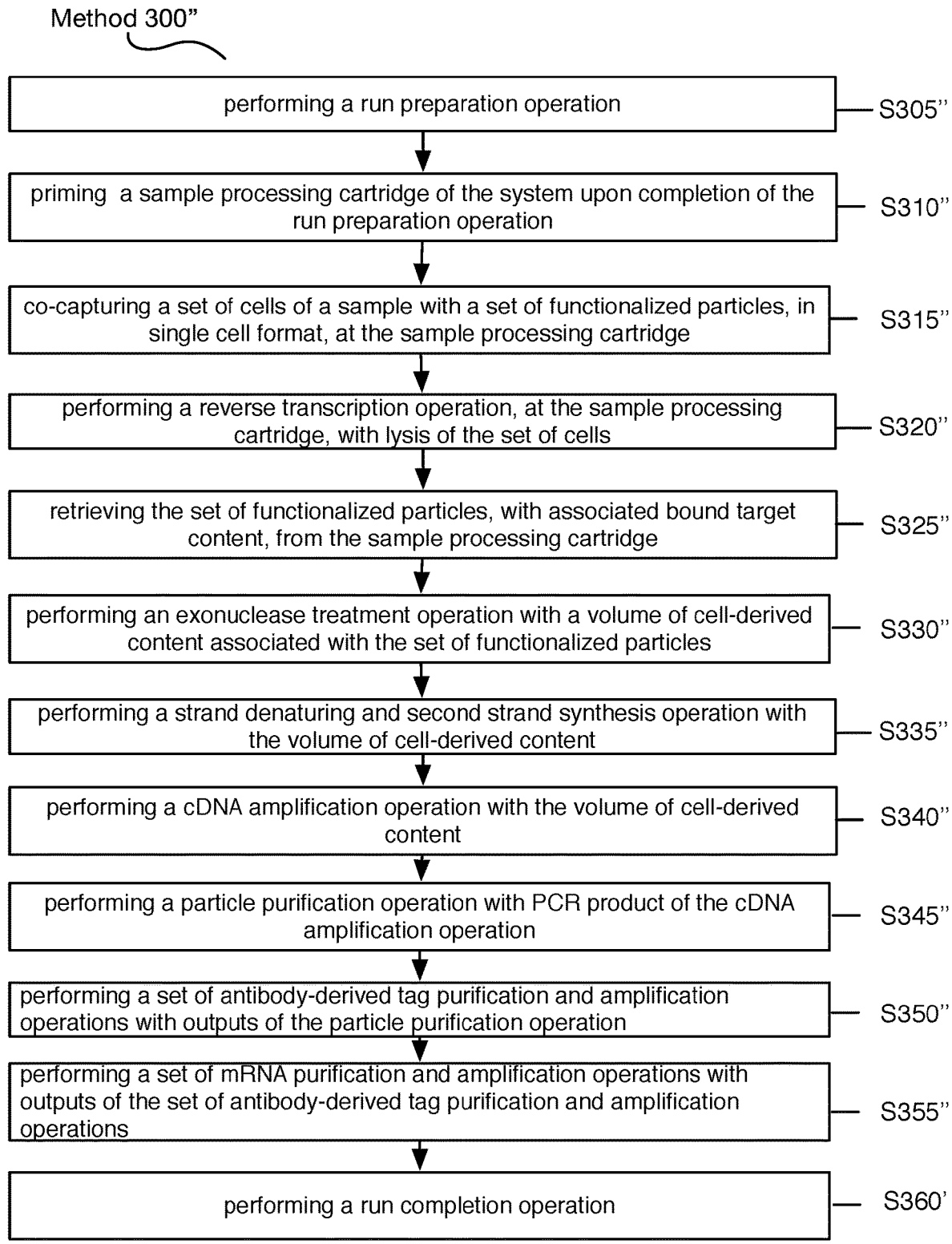
FIG. 17 depicts a second variation of a method for automated single cell sample processing.

As shown in FIG. 17, a variation of the method, configured for single cell cytometry 300" can include: performing a run preparation operation, wherein the run preparation operation configures a system for performing a single cell cytometry protocol S305"; priming a sample processing cartridge of the system upon completion of the run preparation operation S310"; co-capturing a set of cells of a sample with a set of functionalized particles, in single cell format, at the sample processing cartridge S315"; lysing the set of cells followed by binding released antibody-tagged oligonucleotides from the lysed cells to functionalized particles (e.g., barcoded microspheres) S320"(e.g., with washing the unbound materials and then performing a reverse transcription operation); retrieving the set of functionalized particles, with associated bound target content, from the sample processing cartridge S325"; performing an exonuclease treatment operation with a volume of cell-derived content associated with the set of functionalized particles S330"; performing a strand denaturing and second strand synthesis operation with the volume of cell-derived content S335"; performing a cDNA amplification operation with the volume of cell-derived content S340"; performing a particle purification operation with PCR product of the cDNA amplification operation S345"; performing a set of antibody-derived tag purification and amplification operations with outputs of the particle purification operation S350"; performing a set of mRNA purification and amplification operations with outputs of the set of antibody-derived tag purification and amplification operations S355"; and performing a run completion operation upon completion of the set of mRNA purification and amplification operations S360".

In more detail, performing a run preparation operation, S305" can include sub-steps associated with one or more of: preparing a cell suspension; initializing and performing operational checks of system subsystems (e.g., associated with the deck, associated with the gantry, associated with the base, etc.); returning the gantry to a home position; removing one or more seals from the reagent cartridge and/or loading reagents onto the reagent cartridge; positioning a sample processing cartridge unit; removing one or more seals from the tool container positioned at the deck; dispensing the cell suspension into a storage container prior to use; verifying proper positioning and states (e.g., in relation to expiration dates) of disposables for the protocol, upon scanning tags of disposables with a camera (e.g., machine vision camera); receiving sample identification information (e.g., from an operator); and initiating run of the sample. Steps of S305" can be implemented by the system automatically and/or by an operator. Furthermore, various sub-steps can be performed once, or repeated as recommended.

In more detail, priming a sample processing cartridge of the system upon completion of the run preparation operation S310" and co-capturing a set of cells of a sample with a set of functionalized particles, in single cell format, at the sample processing cartridge S315" can include one or more of: dispensing a priming solution into the inlet reservoir of a sample processing cartridge; incubating the priming solution within the sample processing cartridge; dispensing one or more wash solutions into the inlet reservoir of the sample processing cartridge; transmitting solutions to a waste containment region of the sample processing cartridge; dispensing a cell suspension into the inlet reservoir of the sample processing cartridge and capturing cells, in single-cell format, within wells of the sample processing cartridge; dispensing a set of functionalized particles into the inlet reservoir of the sample processing cartridge and co-capturing the set of functionalized particles with the set of cells; incubating content of the wells of the sample processing cartridge; and picking up/releasing various tools involved with the substep(s). Steps S310" and S315" are preferably performed automatically by the system but can alternatively be performed in another suitable manner. Furthermore, various sub-steps can be performed once, or repeated as recommended.

In more detail, performing a reverse transcription operation, at the sample processing cartridge, with lysis of the set of cells S320" can include one or more of: dispensing one or more wash solutions into the inlet reservoir of the sample processing cartridge; transmitting solutions to a waste containment region of the sample processing cartridge; dispensing a particle-binding buffer into the inlet reservoir of the sample processing cartridge; dispensing a DTT solution into the inlet reservoir of the sample processing cartridge; dispensing a lysis solution into the inlet reservoir of the sample processing cartridge; displacing fluid above wells of the sample processing cartridge with an oil, thereby isolating contents of wells and preventing undesired material transfer across wells (e.g., as in U.S. application Ser. No. 16/564,375 filed 9 Sep. 2019, which is herein incorporated in its entirety by this reference); displacing the oil with air from the inlet reservoir; dispensing a particle-binding wash buffer into the inlet reservoir of the sample processing cartridge; dispensing a pre-RT reaction wash buffer into the inlet reservoir of the sample processing cartridge; dispensing a cDNA synthesis solution (e.g., SuperScript IV™) into the inlet reservoir of the sample processing cartridge; dispensing an RT cocktail into the inlet reservoir of the sample processing cartridge; incubating contents of the sample processing cartridge; performing incubation steps; and picking up/releasing various tools involved with the substep(s). Step S320" is preferably performed automatically by the system but can alternatively be performed in another suitable manner. Furthermore, various sub-steps can be performed once, or repeated as recommended.

In more detail, retrieving the set of functionalized particles, with associated bound target content, from the sample processing cartridge S325" can include performing magnetic separation operations (e.g., as described above), using manual or automatic operations. Furthermore, various sub-steps can be performed once, or repeated as recommended.

In more detail, performing an exonuclease treatment operation with a volume of cell-derived content associated with the set of functionalized particles S330" can include one or more of: mixing water and exonuclease buffer to produce an exonuclease solution having a desired concentration; dispensing the exonuclease solution, with functionalized particles into a first PCR container; dispensing an oil (e.g., mineral oil) into the first PCR container; thermocycling and incubating contents of the first PCR container; extracting a product of the first PCR container; performing a separation operation with the product of the first PCR container; discarding waste from the separation operation; performing incubation steps; and picking up/releasing various tools involved with the substep(s). Step S330" is preferably performed automatically by the system but can alternatively be performed in another suitable manner. Furthermore, various sub-steps can be performed once, or repeated as recommended.

In more detail, performing a strand denaturing and second strand synthesis operation S335" can include one or more of: transferring a hydroxide solution (e.g., sodium hydroxide solution) to a second magnetic separation container; mixing contents of the second magnetic separation container; activating a magnetic separation subsystem (e.g., set of magnets coupled to actuator, described above) in proximity to the second magnetic separation container, thereby separating functionalized magnetic particles toward the magnet(s); discarding waste material from the second magnetic separation container; dispensing a wash solution to the magnetic separation container; mixing a second strand synthesis primer enzyme within a process container in proximity to the second magnetic separation container; mixing the second strand synthesis primer enzyme with contents of the second magnetic separation container; dispensing product of the second magnetic separation container into a second PCR container; thermocycling contents of the second PCR container, with mixing; transferring product of the second PCR container to a third magnetic separation container; magnetically separating product of the third magnetic separation container from waste and discarding waste; transferring a wash solution to the third magnetic separation container; and picking up/releasing various tools involved with the substep(s). Step S335" is preferably performed automatically by the system but can alternatively be performed in another suitable manner. Furthermore, various sub-steps can be performed once, or repeated as recommended.

In more detail, performing a cDNA synthesis operation S340" can include one or more of: mixing a polymerase blend (e.g., Kapa Biosystems HiFi Hotstart Ready Mix™) within a cold storage volume; mixing the PCR master mix from the cold storage volume with contents of the third magnetic separation container; aliquoting contents of the third magnetic separation container into a third, fourth, fifth, and sixth PCR operation containers; aliquoting an oil (e.g., mineral oil) into the third, fourth, fifth, and sixth PCR operation containers; running a first PCR operation; and picking up/releasing various tools involved with the substep(s). Step S340" is preferably performed automatically by the system but can alternatively be performed in another suitable manner. Furthermore, various sub-steps can be performed once, or repeated as recommended.

In more detail, performing a particle purification operation with PCR product of the cDNA amplification operation S345" can include one or more of: dispensing product from the third, fourth, fifth, and sixth PCR operation containers into a fourth magnetic separation container; separating target content of the fourth magnetic separation container and transmitting target content into a fifth magnetic separation container; mixing and transferring PCR purification particles (e.g., AMPure beads XP™) into the fifth magnetic separation container; transferring product of the fifth magnetic separation container into a sixth separation container; and picking up/releasing various tools involved with the substep(s). Step S345" is preferably performed automatically by the system but can alternatively be performed in another suitable manner. Furthermore, various sub-steps can be performed once, or repeated as recommended.

In more detail, performing a set of antibody-derived tag purification and amplification operations with outputs of the particle purification operation S350" can include one or more of: mixing and transferring PCR purification particles (e.g., AMPure beads XP™) into the sixth magnetic separation container; discarding waste from the sixth magnetic separation container; diluting and mixing ethanol with nuclease-free water within a process container; transferring ethanol to the sixth magnetic separation container; discarding waste from the sixth magnetic separation container, upon performing magnetic separation; transferring target content of the sixth magnetic separation container into a seventh magnetic separation container; mixing PCR purification particles (e.g., AMPure beads XP™) into the seventh magnetic separation container; transferring ethanol to the seventh magnetic separation container; discarding waste from the seventh magnetic separation container, upon performing magnetic separation; dispensing water into the seventh magnetic separation container; transferring purified cDNA from the seventh magnetic separation container into a seventh PCR operation container; and picking up/releasing various tools involved with the substep(s). Step S350" is preferably performed automatically by the system but can alternatively be performed in another suitable manner. Furthermore, various sub-steps can be performed once, or repeated as recommended.

In more detail, performing a set of mRNA purification and amplification operations with outputs of the set of antibody-derived tag purification and amplification operations S355" can include one or more of: transferring PCR indexing primers into the seventh PCR operation container; transferring a polymerase blend into the seventh PCR operation container; mixing contents of the seventh PCR operation container; transferring an oil (e.g., mineral oil) into the seventh PCR operation container; initiating a second PCR operation; transferring PCR product from the seventh PCR operation container to an eighth magnetic separation container; transferring PCR purification particles (e.g., AMPure beads XP) into the eighth magnetic separation container; transferring ethanol to the eighth magnetic separation container; discarding waste from the eighth magnetic separation container, upon performing magnetic separation; dispensing water into the eighth magnetic separation container; transferring purified cDNA from the eighth magnetic separation container into a storage container; and picking up/releasing various tools involved with the substep(s). Step S355" is preferably performed automatically by the system but can alternatively be performed in another suitable manner. Furthermore, various sub-steps can be performed once, or repeated as recommended.

In more detail, performing a run completion operation upon completion of the set of mRNA purification and amplification operations S360" can include one or more of: returning the gantry to a home configuration; providing a notification that sample processing is complete; releasing the reagent cartridge and/or sample processing cartridge from the system for off-boardstorage; discarding system waste; performing a system cleaning operation; and transitioning the system to a deactivated (e.g., idle, off) state. Steps of S360" can be implemented by the system automatically and/or by an operator. Furthermore, various sub-steps can be performed once, or repeated as recommended.

Example details of steps of the method 300" are further described in TABLE 1 of Appendix B. In relation to steps of the method 300", descriptions of ambient temperature and chilled reagents, as well as positions associated with storage volumes of an embodiment of the reagent cartridge described above are described in TABLE 2 of Appendix B. In relation to TABLE 2 of Appendix B, volumes of reagents can be scaled according to sizes of sample processing chips used and/or number of reactions run. In relation to magnetic separation operations, descriptions of apparatus and associated reagents used, as well as positions associated with storage volumes of an embodiment of the reagent cartridge described above are described in TABLE 3 of Appendix B. In relation to amplification (e.g., PCR) operations, descriptions of apparatus and associated reagents used, as well as positions associated with storage volumes of an embodiment of the reagent cartridge described above are described in TABLE 4 of Appendix B. In relation to fluid aspiration and delivery operations, descriptions of apparatus, as well as positions associated with an embodiment of the tool container described above are described in TABLE 5 of Appendix B. In relation to actuation of components for automation of protocol aspects, gantry arm and pipettor operations (e.g., in relation to apparatus coupling with disposables, apparatus uncoupling from disposables, fluid mixing, waste discarding, aspiration, delivery, aliquoting, etc.) are described in TABLE 6 of Appendix B. In relation to transitioning between modes for automation of protocol aspects, sample processing cartridge operations are described in TABLE 7 of Appendix B. In relation to transitioning between modes for automation of protocol aspects, heating and cooling subsystem operation modes are described in TABLE 8 of Appendix B. In relation to transitioning between modes for automation of protocol aspects, magnetic separation subsystem operations are described in TABLE 9 of Appendix B. In relation to amplification operations, PCR program details associated with the method 300" are described in TABLE 10 of Appendix B.

3.3 Method—Example Workflow for CITE-Seq Protocol (Single Cell Multiomics)

Figure 18:
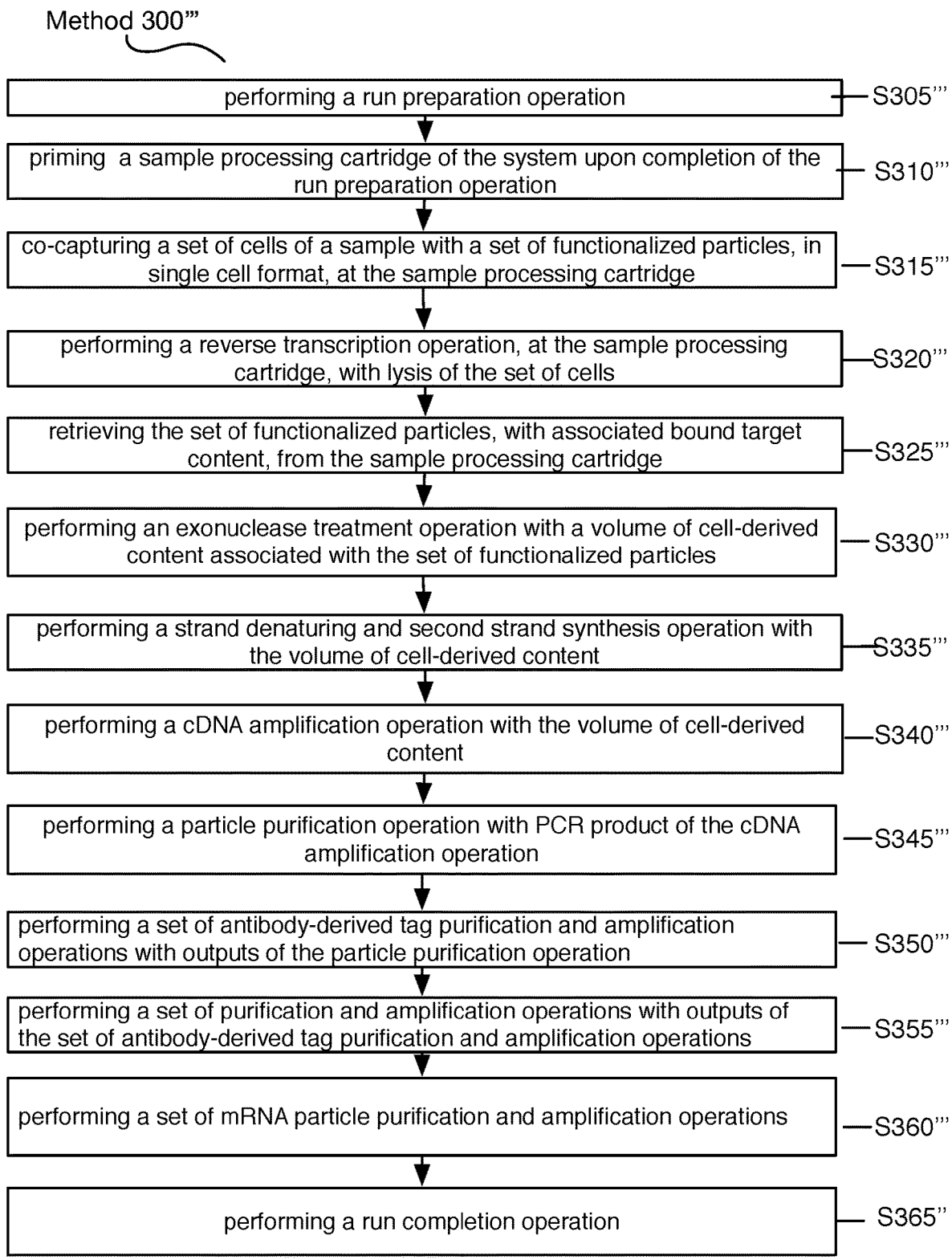
FIG. 18 depicts a third variation of a method for automated single cell sample processing.

As shown in FIG. 18, a variation of the method, configured for single cell multiomics 300'''' can include: performing a run preparation operation, wherein the run preparation operation configures a system for performing a single cell multiomics protocol S305''''; priming a sample processing cartridge of the system upon completion of the run preparation operation S310''''; co-capturing a set of cells of a sample with a set of functionalized particles, in single cell format, at the sample processing cartridge S315''''; at the sample processing cartridge, with lysis of the set of cells, binding mRNA and antibody tagged oligos from the lysed cells to the set of functionalized particles, with washing of unbound materials followed by performing a reverse transcription reaction S320''''; retrieving the set of functionalized particles, with associated bound target content, from the sample processing cartridge S325''''; performing an exonuclease treatment operation with a volume of cell-derived content associated with the set of functionalized particles S330''''; performing a strand denaturing and second strand synthesis operation with the volume of cell-derived content S335''''; performing a cDNA amplification operation with the volume of cell-derived content S340''''; performing a particle purification operation with PCR product of the cDNA amplification operation S345'; performing a set of antibody-derived tag purification and amplification operations with outputs of the particle purification operation S350''''; performing a set of purification and amplification operations with outputs of the set of antibody-derived tag purification and amplification operations S355''''; performing a set of mRNA particle purification and amplification operations S360''''; and performing a run completion operation upon completion of the set of mRNA purification and amplification operations S35'''.

In more detail, performing a run preparation operation, S305'''' can include sub-steps associated with one or more of: preparing a cell suspension; initializing and performing operational checks of system subsystems (e.g., associated with the deck, associated with the gantry, associated with the base, etc.); returning the gantry to a home position; removing one or more seals from the reagent cartridge and/or loading reagents onto the reagent cartridge; positioning a sample processing cartridge unit; removing one or more seals from the tool container positioned at the deck; dispensing the cell suspension into a storage container prior to use; verifying proper positioning and states (e.g., in relation to expiration dates) of disposables for the protocol, upon scanning tags of disposables with a camera (e.g., machine vision camera); receiving sample identification information (e.g., from an operator); and initiating run of the sample. Steps of S305'''' can be implemented by the system automatically and/or by an operator. Furthermore, various sub-steps can be performed once, or repeated as recommended.

In more detail, priming a sample processing cartridge of the system upon completion of the run preparation operation S310'''' and co-capturing a set of cells of a sample with a set of functionalized particles, in single cell format, at the sample processing cartridge S315'''' can include one or more of: dispensing a priming solution into the inlet reservoir of a sample processing cartridge; incubating the priming solution within the sample processing cartridge; dispensing one or more wash solutions into the inlet reservoir of the sample processing cartridge; transmitting solutions to a waste containment region of the sample processing cartridge; dispensing a cell suspension into the inlet reservoir of the sample processing cartridge and capturing cells, in single-cell format, within wells of the sample processing cartridge; dispensing a set of functionalized particles into the inlet reservoir of the sample processing cartridge and co-capturing the set of functionalized particles with the set of cells; incubating content of the wells of the sample processing cartridge; and picking up/releasing various tools involved with the substep(s). Steps S310'''' and S315'''' are preferably performed automatically by the system but can alternatively be performed in another suitable manner. Furthermore, various sub-steps can be performed once, or repeated as recommended.

In more detail, performing a reverse transcription operation, at the sample processing cartridge, with lysis of the set of cells S320'''' can include one or more of: dispensing one or more wash solutions into the inlet reservoir of the sample processing cartridge; transmitting solutions to a waste containment region of the sample processing cartridge; dispensing a particle-binding buffer into the inlet reservoir of the sample processing cartridge; dispensing a DTT solution into the inlet reservoir of the sample processing cartridge; dispensing a lysis solution into the inlet reservoir of the sample processing cartridge; displacing fluid above wells of the sample processing cartridge with an oil, thereby isolating contents of wells and preventing undesired material transfer across wells (e.g., as in U.S. application Ser. No. 16/564,375 filed 9 Sep. 2019, which is herein incorporated in its entirety by this reference); displacing the oil with air from the inlet reservoir; dispensing a particle-binding wash buffer into the inlet reservoir of the sample processing cartridge; dispensing a pre-RT reaction wash buffer into the inlet reservoir of the sample processing cartridge; dispensing a cDNA synthesis solution (e.g., SuperScript IV™) into the inlet reservoir of the sample processing cartridge; dispensing an RT cocktail into the inlet reservoir of the sample processing cartridge; incubating contents of the sample processing cartridge; performing incubation steps; and picking up/releasing various tools involved with the substep(s). Step S320'''' is preferably performed automatically by the system but can alternatively be performed in another suitable manner. Furthermore, various sub-steps can be performed once, or repeated as recommended.

In more detail, retrieving the set of functionalized particles, with associated bound target content, from the sample processing cartridge S325'''' can include performing magnetic separation operations (e.g., as described above), using manual or automatic operations. Furthermore, various sub-steps can be performed once, or repeated as recommended.

In more detail, performing an exonuclease treatment operation with a volume of cell-derived content associated with the set of functionalized particles S330'''' can include one or more of: mixing water and exonuclease buffer to produce an exonuclease solution having a desired concentration; dispensing the exonuclease solution, with functionalized particles into a first PCR container; dispensing an oil (e.g., mineral oil) into the first PCR container; thermocycling and incubating contents of the first PCR container; extracting a product of the first PCR container; performing a separation operation with the product of the first PCR container; discarding waste from the separation operation; performing incubation steps; and picking up/releasing various tools involved with the substep(s). Step S330'''' is preferably performed automatically by the system but can alternatively be performed in another suitable manner. Furthermore, various sub-steps can be performed once, or repeated as recommended.

In more detail, performing a strand denaturing and second strand synthesis operation S335'''' can include one or more of: transferring a hydroxide solution (e.g., sodium hydroxide solution) to a second magnetic separation container; mixing contents of the second magnetic separation container; activating a magnetic separation subsystem (e.g., set of magnets coupled to actuator, described above) in proximity to the second magnetic separation container, thereby separating functionalized magnetic particles toward the magnet(s); discarding waste material from the second magnetic separation container; dispensing a wash solution to the magnetic separation container; mixing a second strand synthesis primer enzyme within a process container in proximity to the second magnetic separation container; mixing the second strand synthesis primer enzyme with contents of the second magnetic separation container; dispensing product of the second magnetic separation container into a second PCR container; thermocycling contents of the second PCR container, with mixing; transferring product of the second PCR container to a third magnetic separation container; magnetically separating product of the third magnetic separation container from waste and discarding waste; transferring a wash solution to the third magnetic separation container; and picking up/releasing various tools involved with the substep(s). Step S335''' is preferably performed automatically by the system but can alternatively be performed in another suitable manner. Furthermore, various sub-steps can be performed once, or repeated as recommended.

In more detail, performing a cDNA synthesis operation S340'' can include one or more of: mixing a polymerase blend (e.g., Kapa Biosystems HiFi Hotstart Ready Mix™) within a cold storage volume; mixing the PCR master mix from the cold storage volume with contents of the third magnetic separation container; aliquoting contents of the third magnetic separation container into a third, fourth, fifth, and sixth PCR operation containers; aliquoting an oil (e.g., mineral oil) into the third, fourth, fifth, and sixth PCR operation containers; running a first PCR operation; and picking up/releasing various tools involved with the substep(s). Step S340''' is preferably performed automatically by the system but can alternatively be performed in another suitable manner. Furthermore, various sub-steps can be performed once, or repeated as recommended.

In more detail, performing a particle purification operation with PCR product of the cDNA amplification operation S345''' can include one or more of: dispensing product from the third, fourth, fifth, and sixth PCR operation containers into a fourth magnetic separation container; separating target content of the fourth magnetic separation container and transmitting target content into a fifth magnetic separation container; mixing and transferring PCR purification particles (e.g., AMPure beads XP™) into the fifth magnetic separation container; transferring product of the fifth magnetic separation container into a sixth separation container; and picking up/releasing various tools involved with the substep(s). Step S345''' is preferably performed automatically by the system but can alternatively be performed in another suitable manner. Furthermore, various sub-steps can be performed once, or repeated as recommended.

In more detail, performing a set of antibody-derived tag purification and amplification operations with outputs of the particle purification operation S350'' can include one or more of: mixing and transferring PCR purification particles (e.g., AMPure beads XP™) into the sixth magnetic separation container; discarding waste from the sixth magnetic separation container; diluting and mixing ethanol with nuclease-free water within a process container; transferring ethanol to the sixth magnetic separation container; discarding waste from the sixth magnetic separation container, upon performing magnetic separation; transferring target content of the sixth magnetic separation container into a seventh magnetic separation container; mixing PCR purification particles (e.g., AMPure beads XP™) into the seventh magnetic separation container; transferring ethanol to the seventh magnetic separation container; discarding waste from the seventh magnetic separation container, upon performing magnetic separation; dispensing water into the seventh magnetic separation container; transferring purified cDNA from the seventh magnetic separation container into a seventh PCR operation container; and picking up/releasing various tools involved with the substep(s). Step S350''' is preferably performed automatically by the system but can alternatively be performed in another suitable manner. Furthermore, various sub-steps can be performed once, or repeated as recommended.

In more detail, performing a set of purification and amplification operations with outputs of the set of antibody-derived tag purification and amplification operations S355'' can include one or more of: transferring PCR indexing primers into the seventh PCR operation container; transferring a polymerase blend into the seventh PCR operation container; mixing contents of the seventh PCR operation container; transferring an oil (e.g., mineral oil) into the seventh PCR operation container; initiating a second PCR operation; transferring PCR product from the seventh PCR operation container to an eighth magnetic separation container; transferring PCR purification particles (e.g., AMPure beads XP) into the eighth magnetic separation container; transferring ethanol to the eighth magnetic separation container; discarding waste from the eighth magnetic separation container, upon performing magnetic separation; dispensing water into the eighth magnetic separation container; transferring purified cDNA from the eighth magnetic separation container into a storage container; and picking up/releasing various tools involved with the substep(s). Step S355''' is preferably performed automatically by the system but can alternatively be performed in another suitable manner. Furthermore, various sub-steps can be performed once, or repeated as recommended.

In more detail, performing a set of mRNA particle purification and amplification operations S360''' can include one or more of: transferring nuclease-free water into the fifth magnetic separation container, with mixing and incubation; transferring product of the fifth magnetic separation container to a ninth magnetic separation container; mixing and transferring PCR purification particles (e.g., AMPure beads XP™) into the ninth magnetic separation container; transferring ethanol into the ninth magnetic separation container; removing waste from the ninth magnetic separation container, after incubation; mixing nuclease-free water with target content of the ninth magnetic separation container; mixing and incubating contents of the ninth magnetic separation container; transferring purified cDNA product from the ninth magnetic separation container to an eighth PCR operation container; transferring PCR master mix for mRNA amplification into the eighth PCR operation container; mixing contents of the eighth PCR operation container; transferring polymerase blend (e.g., Kapa Biosystems HiFi Hotstart Ready Mix) into the eighth PCR operation container; mixing contents of the eighth PCR operation container; transferring an oil (e.g., mineral oil) into the eighth PCR operation container; performing a third PCR operation within the eighth PCR operation container; transferring product of the third PCR operation from the eighth PCR operation container to a tenth magnetic separation container; transferring PCR purification particles into the tenth magnetic separation container; mixing contents of the tenth magnetic separation container; transferring ethanol to the tenth magnetic separation container; discarding waste from the tenth magnetic separation container; transferring nuclease free water into the tenth magnetic separation container; mixing contents of the tenth magnetic separation container, with incubation; magnetically separating target mRNA-cDNA product from tenth magnetic separation container; transferring target mRNA-cDNA product from tenth magnetic separation container to cold storage; and picking up/releasing various tools involved with the substep(s). Step S360''' is preferably performed automatically by the system but can alternatively be performed in another suitable manner. Furthermore, various sub-steps can be performed once, or repeated as recommended.

In more detail, performing a run completion operation upon completion of the set of mRNA purification and amplification operations S365''' can include one or more of: returning the gantry to a home configuration; providing a notification that sample processing is complete; releasing the reagent cartridge and/or sample processing cartridge from the system for off-boardstorage; discarding system waste; performing a system cleaning operation; and transitioning the system to a deactivated (e.g., idle, off) state. Steps of S365''' can be implemented by the system automatically and/or by an operator. Furthermore, various sub-steps can be performed once, or repeated as recommended.

Example details of steps of the method 300''' are further described in TABLE 1 of Appendix C. In relation to steps of the method 300''', descriptions of ambient temperature and chilled reagents, as well as positions associated with storage volumes of an embodiment of the reagent cartridge described above are described in TABLE 2 of Appendix C. In relation to TABLE 2 of Appendix C, volumes of reagents can be scaled according to sizes of sample processing chips used and/or number of reactions run. In relation to magnetic separation operations, descriptions of apparatus and associated reagents used, as well as positions associated with storage volumes of an embodiment of the reagent cartridge described above are described in TABLE 3 of Appendix C. In relation to amplification (e.g., PCR) operations, descriptions of apparatus and associated reagents used, as well as positions associated with storage volumes of an embodiment of the reagent cartridge described above are described in TABLE 4 of Appendix C. In relation to fluid aspiration and delivery operations, descriptions of apparatus, as well as positions associated with an embodiment of the tool container described above are described in TABLE 5 of Appendix C. In relation to actuation of components for automation of protocol aspects, gantry arm and pipettor operations (e.g., in relation to apparatus coupling with disposables, apparatus uncoupling from disposables, fluid mixing, waste discarding, aspiration, delivery, aliquoting, etc.) are described in TABLE 6 of Appendix C. In relation to transitioning between modes for automation of protocol aspects, sample processing cartridge operations are described in TABLE 7 of Appendix C. In relation to transitioning between modes for automation of protocol aspects, heating and cooling subsystem operation modes are described in TABLE 8 of Appendix C. In relation to transitioning between modes for automation of protocol aspects, magnetic separation subsystem operations are described in TABLE 9 of Appendix C. In relation to amplification operations, PCR program details associated with the method 300''' are described in TABLE 10 of Appendix C.

3.4 Method—Example Workflow for Library Preparation

Figure 19:
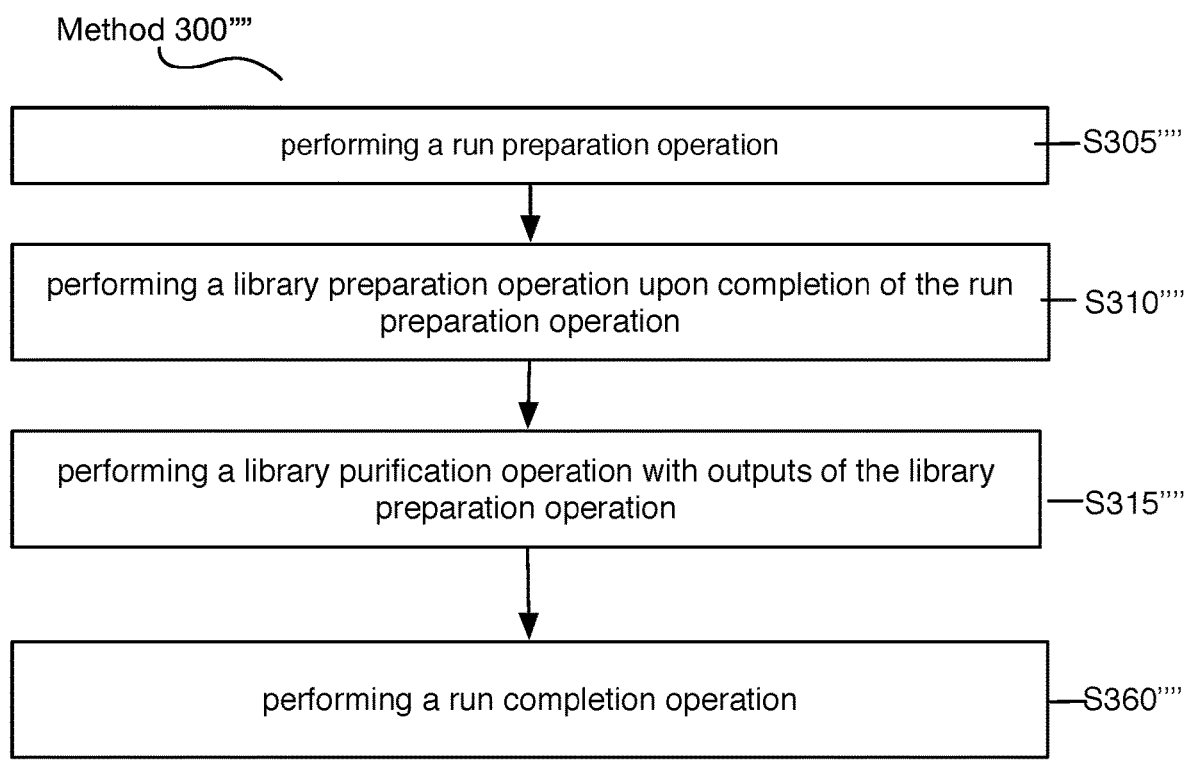
FIG. 19 depicts a third variation of a method for automated single cell sample processing.

As shown in FIG. 19, a variation of the method, configured for library preparation 300'''' can include: performing a run preparation operation, wherein the run preparation operation configures a system for performing a library preparation protocol S305''''; performing a library preparation operation upon completion of the run preparation operation S310''''; performing a library purification operation with outputs of the library preparation operation S315''''; and performing a run completion operation upon completion of the library purification operation S360''''.

In more detail, performing a run preparation operation S305'''' can include substeps associated with one or more of: quantifying concentration of product (e.g., DNA concentration of product produced from a prior protocol; thawing out a reagent cartridge for library preparation, in a frozen storage state; processing storage volumes of the reagent cartridge (e.g., by vortexing, by centrifugation etc.); diluting a sequencing adaptor (e.g., NEBNext Illumina™ adaptor) solution with a dilution buffer; returning the sequencing adaptor solution and previously removed storages to the reagent cartridge; performing operational checks of system subsystems (e.g., associated with the deck, associated with the gantry, associated with the base, etc.); returning the gantry to a home position; positioning the reagent cartridge at a deck of the system; removing one or more seals from the reagent cartridge and/or loading reagents onto the reagent cartridge; positioning a sample processing cartridge unit at a deck of the system; removing one or more seals from the tool container positioned at the deck; receiving an operator-loaded container (e.g., at a storage volume of the reagent cartridge) for performing the library preparation operation); initializing a heating and cooling subsystem (e.g., with an initial temperature set point); verifying proper positioning and states (e.g., in relation to expiration dates) of disposables for the protocol, upon scanning tags of disposables with a camera (e.g., machine vision camera); receiving sample identification information (e.g., from an operator); and initiating run of the sample. Steps of S305'''' can be implemented by the system automatically and/or by an operator. Furthermore, various sub-steps can be performed once, or repeated as recommended.

In more detail, performing a library preparation operation upon completion of the run preparation operation S310'''' can include sub-steps associated with one or more of: transferring diluted cDNA from the operator-loaded tube into a first cold storage container containing buffer; transferring contents of the first cold storage tube to a second cold storage container; incubating contents of the second cold storage container; transferring a cDNA mixture from a second ambient storage container into a first PCR operation container; fragmenting content of the first PCR operation container upon performing thermocycling operations at the first PCR operation container; transferring fragmented DNA from the first PCR operation container to a fourth cold storage container, with mixing; transferring contents of the fourth cold storage container to a fifth cold storage container with mixing; transferring diluted adaptor from a third cold storage container to the fifth cold storage container with mixing and incubation; transferring contents of the fifth cold storage container to a second PCR operation container with incubation; transferring contents of the second PCR operation container to a sixth cold storage container with mixing; transferring contents of the sixth cold storage container to the second PCR operation container with incubation; transferring contents of the second sixth cold storage container to a second magnetic separation container; transferring PCR purification particles (e.g., AMPure beads XP) to the second magnetic separation container with mixing; discarding waste from the second magnetic separation container; transferring ethanol to the second magnetic separation container; discarding waste from the second magnetic separation container; transferring TE buffer to the second magnetic separation container with incubation and magnetic separation; transferring purified cDNA from the second magnetic separation container to a third PCR operation container; transferring indexing PCR master mix to the third PCR operation container with mixing; performing a fourth PCR operation; performing mixing steps; performing incubation steps; and picking up/releasing various tools involved with the substep(s). Step S310"" is preferably performed automatically by the system but can alternatively be performed in another suitable manner. Furthermore, various sub-steps can be performed once, or repeated as recommended.

In more detail, performing a library purification operation with outputs of the library preparation operation S315"" can include sub-steps associated with one or more of: transferring product of the fourth PCR operation from the third PCR operation container to a third magnetic separation container with mixing; transferring PCR purification particles (e.g., AMPure Beads XP) to the third magnetic separation container with mixing, incubation, and magnetic separation; transferring ethanol to the third magnetic separation container with incubation; removing waste from the third magnetic separation container; transferring nuclease-free water to the third magnetic separation container with mixing, incubation, and magnetic separation; transferring contents of the third magnetic separation container to a fourth magnetic separation container with mixing; transferring PCR purification particles (e.g., AMPure Beads XP) to the fourth magnetic separation container with mixing, incubation, and magnetic separation; removing waste from the fourth magnetic separation container; transferring ethanol to the fourth magnetic separation container with incubation; discarding waste from the fourth magnetic separation container; repeating steps for further purification, with transfer of target material from the fourth magnetic separation container to a fifth magnetic separation container, to a sixth magnetic separation container; transferring nuclease-free water to the sixth magnetic separation container with incubation and magnetic separation; transferring purified cDNA for library construction to an eighth cold storage container; performing mixing steps; performing incubation steps; and picking up/releasing various tools involved with the sub-step(s). Step S315"" is preferably performed automatically by the system but can alternatively be performed in another suitable manner. Furthermore, various sub-steps can be performed once, or repeated as recommended.

In more detail, performing a run completion operation upon completion of the library purification operation S360"" can include one or more of: returning the gantry to a home configuration; providing a notification that sample processing is complete; releasing the reagent cartridge and/or sample processing cartridge from the system for off-boardstorage; discarding system waste; performing a system cleaning operation; and transitioning the system to a deactivated (e.g., idle, off) state. Steps of S360"" can be implemented by the system automatically and/or by an operator. Furthermore, various sub-steps can be performed once, or repeated as recommended.

Example details of steps of the method 300"" are further described in TABLE 1 of Appendix D. In relation to steps of the method 300"", descriptions of ambient temperature and chilled reagents, as well as positions associated with storage volumes of an embodiment of the reagent cartridge described above are described in TABLE 2 of Appendix D. In relation to TABLE 2 of Appendix D, volumes of reagents can be scaled according to sizes of sample processing chips used and/or number of reactions run. In relation to magnetic separation operations, descriptions of apparatus and associated reagents used, as well as positions associated with storage volumes of an embodiment of the reagent cartridge described above are described in TABLE 3 of Appendix D. In relation to amplification (e.g., PCR) operations, descriptions of apparatus and associated reagents used, as well as positions associated with storage volumes of an embodiment of the reagent cartridge described above are described in TABLE 4 of Appendix D. In relation to fluid aspiration and delivery operations, descriptions of apparatus, as well as positions associated with an embodiment of the tool container described above are described in TABLE 5 of Appendix D. In relation to actuation of components for automation of protocol aspects, gantry arm and pipettor operations (e.g., in relation to apparatus coupling with disposables, apparatus uncoupling from disposables, fluid mixing, waste discarding, aspiration, delivery, aliquoting, etc.) are described in TABLE 6 of Appendix D. In relation to transitioning between modes for automation of protocol aspects, sample processing cartridge operations are described in TABLE 7 of Appendix D. In relation to transitioning between modes for automation of protocol aspects, heating and cooling subsystem operation modes are described in TABLE 8 of Appendix D. In relation to transitioning between modes for automation of protocol aspects, magnetic separation subsystem operations are described in TABLE 9 of Appendix D. In relation to amplification operations, PCR program details associated with the method 300" are described in TABLE 10 of Appendix D.

The system embodiment(s) can, however, be configured to implement other workflows including variations of those described, and/or other workflows.

4. Conclusion

The FIGS. illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGS. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

What is claimed is:

1. A system for processing a sample, the system comprising:
   a reagent cartridge;
   a deck configured to support and position:
      a sample processing cartridge comprising a set of wells,
      a lid configured to cover an access region over the set of wells of the sample processing cartridge, the lid comprising an open mode in which the access region is uncovered and a closed mode in which the access region is covered, the lid further comprising a releasing element; and a gantry coupled to the deck and comprising:
      a set of tracks defining paths of movement along a set of axes, within a three dimensional volume bound by a first side of the deck, for a pipette interface;
   a heating and cooling subsystem comprising a thermal body configured to thermally interface with the sample processing cartridge; and
   a lid opening tool configured to transition the lid between the open mode and the closed mode,
   with retention of the sample processing cartridge thermally interfaced with the heating and cooling subsystem, wherein the lid-opening tool comprises a linking element configured to engage the releasing element on the lid.

2. The system of claim 1, wherein the sample comprises nucleic acids.

3. The system of claim 1, wherein the sample comprises a cell suspension.

4. The system of claim 1, wherein the reagent cartridge comprises materials for performing polymerase chain reaction (PCR) operations with the sample.

5. The system of claim 1, wherein the reagent cartridge comprises materials for performing library preparation operations with the sample.

6. The system of claim 1, wherein the reagent cartridge comprises materials for performing reverse transcription and cDNA synthesis.

7. The system of claim 1, wherein the lid comprises a gasket configured to seal the access region of the sample processing cartridge in the closed position.

8. The system of claim 1, wherein the lid comprises a latch configured to couple with the sample processing cartridge.

9. The system of claim 1, wherein further comprising a camera coupled with a pipettor coupled to the gantry, the camera having a field of view including objects that the pipettor is aligned with.

10. The system of claim 1, further comprising a separation subsystem comprising a set of magnets coupled to a magnet actuator configured to transition the set of magnets between a retracted state and an extended state, wherein in the extended state, the set of magnets passes into an opening of the deck.

11. A method comprising:
   retaining a sample processing cartridge at a deck;
      wherein the sample processing cartridge comprises:
      a set of wells, and
      a lid configured to cover an access region over the set of wells of the
      sample processing cartridge, the lid comprising an open position in which the access region is uncovered and a closed position in which the access region is covered, the lid further comprising a releasing element;
   transferring a sample to the set of wells of the sample processing cartridge;
   performing a set of operations in coordination with transferring a set of reagents from a reagent cartridge to the set of wells of the sample processing cartridge, wherein the set of operations comprises:
      priming the sample processing cartridge upon dispensing a priming solution into the sample processing cartridge;
   performing a reverse transcription operation, at the set of wells of the sample processing cartridge, on nucleic acids of the sample;
   performing a strand denaturing and second strand synthesis operation upon performance of the reverse transcription operation;
      transitioning, using a lid-opening tool the lid between the open position and the closed position, with
   retention of the sample processing cartridge at the deck, wherein the lid-opening tool comprises a linking element configured to engage the releasing element on the lid; and
   performing a cDNA amplification operation upon performance of the strand denaturing and second strand synthesis operation.

12. The method of claim 11, further comprising binding released mRNA content of the sample to barcoded functionalized particles within the set of wells.

13. The method of claim 11, wherein transitioning the lid between the open position and the closed position comprises applying a force to the lid, thereby isolating the access region of the sample processing cartridge.

14. The method of claim 11, wherein the deck is coupled to a gantry comprising a set of tracks defining paths of movement along a set of axes, the method further comprising:
   with a camera coupled with a pipettor coupled to the gantry, scanning a tag of the sample processing cartridge.

15. The method of claim 14, further comprising guiding movement of components of the gantry, to within 100 micron precision, with feedback using a camera image generated by the camera.

16. The method of claim 11, further comprising performing a set of antibody-derived tag purification and amplification operations with outputs of the cDNA amplification operation, for performance of a CITE-seq single cell multiomics protocol.

17. The method of claim 11, further comprising performing a library preparation operation with material of the sample, wherein the reagent cartridge contains a set of reagents for the library preparation operation, and wherein performing the library preparation operation comprises fragmenting and amplifying nucleic acid content of the sample.

18. The method of claim 17, wherein performing the library preparation operation comprises determining a concentration of a DNA component of the sample; based upon the concentration performing a dilution operation upon the sample; fragmenting cDNA material of the sample; and amplifying fragmented cDNA of the sample.

19. The method of claim 17, further comprising performing a library purification operation with outputs of the library preparation operation upon combining material from the library preparation operation with PCR purification particles, by way of a pipettor coupled to an actuator of a gantry coupled to the deck.

20. The method of claim 11, further comprising performing a separation operation upon the sample, wherein performing the separation operation comprises actuating a magnet toward magnetic separation reservoir at the deck.

* * * * *